(12) United States Patent
Adney et al.

(10) Patent No.: US 10,036,051 B2
(45) Date of Patent: Jul. 31, 2018

(54) ENHANCED PROCESSIVE CELLULASES

(71) Applicant: Alliance for Sustainable Energy, LLC, Golden, CO (US)

(72) Inventors: William S. Adney, Pittsboro, NC (US); Gregg T. Beckham, Golden, CO (US); Eric Jarvis, Boulder, CO (US); Michael E. Himmel, Littleton, CO (US); Stephen R. Decker, Berthoud, CO (US); Jeffrey G. Linger, Denver, CO (US); Kara Podkaminer, Boulder, CO (US); John O. Baker, Golden, CO (US); Larry Taylor, II, Berthoud, CO (US); Qi Xu, Lakewood, CO (US); Arjun Singh, Lakewood, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 15/594,031

(22) Filed: May 12, 2017

(65) Prior Publication Data

US 2017/0247731 A1    Aug. 31, 2017

Related U.S. Application Data

(62) Division of application No. 14/365,200, filed as application No. PCT/US2012/070165 on Dec. 17, 2012, now Pat. No. 9,683,248.

(60) Provisional application No. 61/576,585, filed on Dec. 16, 2011.

(51) Int. Cl.
| | |
|---|---|
| C12P 19/14 | (2006.01) |
| C12P 7/10 | (2006.01) |
| C10L 1/02 | (2006.01) |
| C12N 9/42 | (2006.01) |

(52) U.S. Cl.
CPC ............. *C12P 19/14* (2013.01); *C10L 1/02* (2013.01); *C12N 9/2437* (2013.01); *C12P 7/10* (2013.01); *C12Y 302/01004* (2013.01); *C12Y 302/01021* (2013.01); *C10L 2290/26* (2013.01)

(58) Field of Classification Search
None
See application file for complete search history.

(56) References Cited

U.S. PATENT DOCUMENTS

| | | | |
|---|---|---|---|
| 4,952,501 A | 8/1990 | Jasin et al. | |
| 7,449,550 B2 * | 11/2008 | Adney | C12Y 302/0109 530/350 |
| 8,044,264 B2 | 10/2011 | Lopez De Leon et al. | |
| 8,063,267 B2 | 11/2011 | Harris et al. | |
| 8,283,150 B2 | 10/2012 | Adney et al. | |
| 2014/0322765 A1 | 10/2014 | Adney et al. | |

OTHER PUBLICATIONS

Chica et al. Curr Opin Biotechnol. Aug. 2005;16(4):378-84.*
Singh et al. Curr Protein Pept Sci. 2017, 18, 1-11.*
Beckham et al. Structure-function relationships in the sub-domains of the Family 7 cellulase from Trichoderma reesei. Abstracts of Papers, 239th ACS National Meeting, San Francisco, CA, United States, Mar. 21-25, 2010 (2010), AGFD-240. American Chemical Society: Washington, D. C.*
Adney et al. Cellulose (Dordrecht, Netherlands) (2009), 16(4), 699-709.*
Chica et al., "Semi-rational Approaches to Engineering Enzyme Activity: Combining the Benefits of Directed Evolution and Rational Design", Current Opinion in Biotechnology, 2005, vol. 16, pp. 378-384.
Heinzelman et al., "A Family of Thermostable Fungal Cellulases Created by Structure-guided Recombination", Proceedings of the National Academy of Sciences, Apr. 7, 2009, vol. 106, No. 14, pp. 5610-5615.
Heinzelman et al., "SCHEMA Recombination of a Fungal Cellulase Uncovers a Single Mutation That Contributes Markedly to Stability", The Journal of Biological Chemistry, Sep. 25, 2009, vol. 284, No. 39, pp. 26229-26233.
Kim et al, "Binding Modules Alter the Activity of Chimeric Cellulases: Effects of Biomass Pretreatment and Enzyme Source", Biofuels and Environmental Biotechnology: Biotechnology and Bioengineering, Nov. 1, 2010, vol. 107, No. 4, pp. 601-611.
Penttila et al, "A Versatile Transformation System for the Cellulolytic Filamentous Fungus *Trichoderma reesei*", Gene, 1987, vol. 61, pp. 155-164.
Sen et al., "Developments in Directed Evolution for Improving Enzyme Functions", Applied Biochemistry Biotechnology, 2007, vol. 143, pp. 212-223.
Srisodsuk et al., "Role of the Interdomain Linker Peptide of *Trichoderma reesei* Cellubiohydrolase I in Its Interaction with Crystalline Cellulose", The Journal of Biological Chemistry, Oct. 5, 1993, vol. 268, No. 28, pp. 20756-20761.
Srisodsuk et al., "*Trichoderma reesei* cellobiohydrolase I with an endoglucanase cellulose-binding domain: action on bacterial microcrystalline cellulose", Journal of Biotechnology, 1997, vol. 57, pp. 49-57.
Wilson, "Cellulases and Biofuels", Current Opinion in Biotechnology, Jun. 2009, vol. 20, No. 3, pp. 295-299.
Accession AY690432, Dec. 14, 2009.
Accession Q68HC2, Oct. 11, 2004.
Accession P62694, Jul. 21, 1986.
Accession AY368686, Mar. 23, 2010.
Accession Q6UJY1, Jul. 5, 2004.
International Search Report issued for International (PCT) Application No. PCT/US12/70165, pp. 1-5, dated Mar. 1, 2013.

(Continued)

*Primary Examiner* — Christian L Fronda
(74) *Attorney, Agent, or Firm* — John C. Stolpa; Alexandra M. Hall

(57) ABSTRACT

Nucleic acid sequences encoding chimeric polypeptides that exhibit enhanced cellulase activities are disclosed herein. These nucleic acids may be expressed in hosts such as fungi, which in turn may be cultured to produce chimeric polypeptides. Also disclosed are chimeric polypeptides and their use in the degradation of cellulosic materials.

17 Claims, 16 Drawing Sheets

(56) References Cited

OTHER PUBLICATIONS

Written Opinion issued for International (PCT) Application No. PCT/US12/70165, pp. 1-6, dated Mar. 1, 2013.

* cited by examiner

Figure 2

SEQ ID NO:1

CAGCAAATTGGTACTTATACCGCTGAAACCCATCCCTCTCTGAGCTGGTCTACTTGCAAATC
GGGTGGTAGCTGCACCACAAACTCCGGTGCCATTACGTTAGATGCCAACTGGCGTTGGGTCC
ATGGTGTCAATACCAGCACCAACTGCTACACTGGCAACACTTGGAATAGCGCCATCTGCGAC
ACTGATGCATCCTGTGCCCAGGACTGTGCTCTCGATGGTGCTGACTACTCTGGCACGTACGG
TATCACTACCTCCGGCAACTCATTGCGCCTGAACTTCGTTACCGGTTCCAACGTCGGATCTC
GTACTTACCTGATGGCCGATAACACCCACTACCAAATCTTCGATCTGTTGAACCAGGAGTTC
ACCTTCACCGTCGATGTCTCCCACCTCCCTTGCGGTTTGAACGGTGCCCTCTACTTCGTGAC
CATGGATGCCGACGGTGGCGTCTCCAAGTACCCCAACAACAAGGCCGGTGCTCAGTACGGTG
TTGGATACTGTGACTCTCAATGCCCTCGTGACTTGAAGTTCATCGCTGGTCAGGCCAACGTT
GAGGGCTGGACGCCCTCCGCCAACAACGCCAACACTGGAATTGGCAATCACGGAGCTTGCTG
CGCGGAGCTTGATATCTGGGAGGCAAACAGCATCTCAGAGGCCTTGACTCCTCACCCTTGCG
ATACACCCGGTCTATCTGTTTGCACTACTGATGCCTGCGGTGGTACCTACAGCTCTGATCGT
TACGCCGGTACCTGCGACCCTGATGGATGTGACTTCAACCCTTACCGCCTTGGTGTCACTGA
CTTCTACGGCTCCGGCAAGACCGTTGACACCACCAAGCCCTTTACCGTTGTGACTCAATTCG
TCACTAACGACGGTACCTCCACCGGTTCCCTCTCCGAGATCAGACGTTACTACGTTCAGAAC
GGCGTTGTCATCCCCCAGCCTTCCTCCAAGATCTCCGGAATCAGCGGAAATGTCATCAACTC
CGACTACTGCGCTGCTGAAATTTCCACCTTTGGCGGGACTGCCTCCTTCAGCAAACACGGTG
GCTTGACAAACATGGCCGCTGGTATGGAAGCTGGTATGGTCTTGGTCATGAGTTTGTGGGAC
GACTACGCCGTCAACATGCTCTGGCTCGACAGCACCTACCCTACAAACGCGACTGGTACCCC
CGGTGCCGCTCGTGGTACCTGCGCTACCACTTCTGGGGACCCCAAGACCGTTGAATACAAT
CCGGCAGCTCCTATGTCACCTTCTCTGACATTCGGGTTGGTCCTTTCAATTCTACGTTCAGC
GGTGGTTCTAGCACCGGTGGCAGCACTACTACTACCGCCAGCCGCACCACCACCACCTCGGC
CTCTTCCACCTCTACTTCCAGCACCTCTACTGGCACTGGA**GTCGCTGGTCACTGGGGTCAGT
GTGGTGGCCAGGGCTGGACTGGCCCTACCACCTGTGTTAGTGGAACCACATGCACCGTCGTG
AACCCTTACTACTCTCAATGTTTG**

SEQ ID NO:2

QQIGTYTAETHPSLSWSTCKSGGSCTTNSGAITLDANWRWVHGVNTSTNCYTGNTWNSAICD
TDASCAQDCALDGADYSGTYGITTSGNSLRLNFVTGSNVGSRTYLMADNTHYQIFDLLNQEF
TFTVDVSHLPCGLNGALYFVTMDADGGVSKYPNNKAGAQYGVGYCDSQCPRDLKFIAGQANV
EGWTPSANNANTGIGNHGACCAELDIWEANSISEALTPHPCDTPGLSVCTTDACGGTYSSDR
YAGTCDPDGCDFNPYRLGVTDFYGSGKTVDTTKPFTVVTQFVTNDGTSTGSLSEIRRYYVQN
GVVIPQPSSKISGISGNVINSDYCAAEISTFGGTASFSKHGGLTNMAAGMEAGMVLVMSLWD
DYAVNMLWLDSTYPTNATGTPGAARGTCATTSGDPKTVESQSGSSYVTFSDIRVGPFNSTFS
GGSSTGGSTTTTASRTTTTSASSTSTSSTSTGTG**VAGHWGQCGGQGWTGPTTCVSGTTCTVV
NPYYSQCL**

Figure 3

SEQ ID NO:3

CAGTCGGCCTGCACTCTCCAATCGGAGACTCACCCGCCTCTGACATGGCAGAAATGCTCGTC
TGGTGGCACGTGCACTCAACAGACAGGCTCCGTGGTCATCGACGCCAACTGGCGCTGGACTC
ACGCTACGAACAGCAGCACGAACTGCTACGATGGCAACACTTGGAGCTCGACCCTATGTCCT
GACAACGAGACCTGCGCGAAGAACTGCTGTCTGGACGGTGCCGCCTACGCGTCCACGTACGG
AGTTACCACGAGCGGTAACAGCCTCTCCATTGGCTTTGTCACCCAGTCTGCGCAGAAGAACG
TTGGCGCTCGCCTTTACCTTATGGCGAGCGACACGACCTACCAGGAATTCACCCTGCTTGGC
AACGAGTTCTCTTTCGATGTTGATGTTTCGCAGCTGCCGTGCGGCTTGAACGGAGCTCTCTA
CTTCGTGTCCATGGACGCGGATGGTGGCGTGAGCAAGTATCCCACCAACACCGCTGGCGCCA
AGTACGGCACGGGGTACTGTGACAGCCAGTGTCCCCGCGATCTGAAGTTCATCAATGGCCAG
GCCAACGTTGAGGGCTGGGAGCCGTCATCCAACAACGCGAACACGGGCATTGGAGGACACGG
AAGCTGCTGCTCTGAGATGGATATCTGGGAGGCCAACTCCATCTCCGAGGCTCTTACCCCCC
ACCCTTGCACGACTGTCGGCCAGGAGATCTGCGAGGGTGATGGGTGCGGCGGAACTTACTCC
GATAACAGATATGGCGGCACTTGCGATCCCGATGGCTGCGACTGGAACCCATACCGCCTGGG
CAACACCAGCTTCTACGGCCCTGGCTCAAGCTTTACCCTCGATACCACCAAGAAATTGACCG
TTGTCACCCAGTTCGAGACGTCGGGTGCCATCAACCGATACTATGTCCAGAATGGCGTCACT
TTCCAGCAGCCCAACGCCGAGCTTGGTAGTTACTCTGGCAACGAGCTCAACGATGATTACTG
CACAGCTGAGGAGGCAGAATTCGGCGGATCCTCTTTCTCAGACAAGGGCGGCCTGACTCAGT
TCAAGAAGGCTACCTCTGGCGGCATGGTTCTGGTCATGAGTCTGTGGGATGATTACTACGCC
AACATGCTGTGGCTGGACTCCACCTACCCGACAAACGAGACCTCCTCCACACCCGGTGCCGT
GCGCGGAAGCTGCTCCACCAGCTCCGGTGTCCCTGCTCAGGTCGAATCTCAGTCTCCCAACG
CCAAGGTCACCTTCTCCAACATCAAGTTCGGACCCATTGGCAGCACCGGCAACCCTAGCGGC
GGCAACCCTCCCGGCGGAAACCCGCCTGGCACCACCACCACCCGCCGCCCAGCCACTACCAC
TGGAAGCTCTCCCGGACCT**ACCCAGTCTCACTACGGCCAGTGCGGCGGTATTGGCTACAGCG
GCCCCACGGTCTGCGCCAGCGGCACAACTTGCCAGGTCCTGAACCCTTACTACTCTCAGTGC
CTG**

SEQ ID NO:4

QSACTLQSETHPPLTWQKCSSGGTCTQQTGSVVIDANWRWTHATNSSTNCYDGNTWSSTLCP
DNETCAKNCCLDGAAYASTYGVTTSGNSLSIGFVTQSAQKNVGARLYLMASDTTYQEFTLLG
NEFSFDVDVSQLPCGLNGALYFVSMDADGGVSKYPTNTAGAKYGTGYCDSQCPRDLKFINGQ
ANVEGWEPSSNNANTGIGGHGSCCSEMDIWEANSISEALTPHPCTTVGQEICEGDGCGGTYS
DNRYGGTCDPDGCDWNPYRLGNTSFYGPGSSFTLDTTKKLTVVTQFETSGAINRYYVQNGVT
FQQPNAELGSYSGNELNDDYCTAEEAEFGGSSFSDKGGLTQFKKATSGGMVLVMSLWDDYYA
NMLWLDSTYPTNETSSTPGAVRGSCSTSSGVPAQVESQSPNAKVTFSNIKFGPIGSTGNPSG
GNPPGGNPPGTTTTRRPATTTGSSPGP**TQSHYGQCGGIGYSGPTVCASGTTCQVLNPYYSQC
L**

Figure 4

SEQ ID NO:5

CAGCAAATTGGTACTTATACCGCTGAAACCCATCCCTCTCTGAGCTGGTCTACTTGCAAATC
GGGTGGTAGCTGCACCACAAACTCCGGTGCCATTACGTTAGATGCCAACTGGCGTTGGGTCC
ATGGTGTCAATACCAGCACCAACTGCTACACTGGCAACACTTGGAATAGCGCCATCTGCGAC
ACTGATGCATCCTGTGCCCAGGACTGTGCTCTCGATGGTGCTGACTACTCTGGCACGTACGG
TATCACTACCTCCGGCAACTCATTGCGCCTGAACTTCGTTACCGGTTCCAACGTCGGATCTC
GTACTTACCTGATGGCCGATAACACCCACTACCAAATCTTCGATCTGTTGAACCAGGAGTTC
ACCTTCACCGTCGATGTCTCCCACCTCCCTTGCGGTTTGAACGGTGCCCTCTACTTCGTGAC
CATGGATGCCGACGGTGGCGTCTCCAAGTACCCCAACAACAAGGCCGGTGCTCAGTACGGTG
TTGGATACTGTGACTCTCAATGCCCTCGTGACTTGAAGTTCATCGCTGGTCAGGCCAACGTT
GAGGGCTGGACGCCCTCCGCCAACAACGCCAACACTGGAATTGGCAATCACGGAGCTTGCTG
CGCGGAGCTTGATATCTGGGAGGCAAACAGCATCTCAGAGGCCTTGACTCCTCACCCTTGCG
ATACACCCGGTCTATCTGTTTGCACTACTGATGCCTGCGGTGGTACCTACAGCTCTGATCGT
TACGCCGGTACCTGCGACCCTGATGGATGTGACTTCAACCCTTACCGCCTTGGTGTCACTGA
CTTCTACGGCTCCGGCAAGACCGTTGACACCACCAAGCCCTTTACCGTTGTGACTCAATTCG
TCACTAACGACGGTACCTCCACCGGTTCCCTCTCCGAGATCAGACGTTACTACGTTCAGAAC
GGCGTTGTCATCCCCCAGCCTTCCTCCAAGATCTCCGGAATCAGCGGAAATGTCATCAACTC
CGACTACTGCGCTGCTGAAATTTCCACCTTTGGCGGGACTGCCTCCTTCAGCAAACACGGTG
GCTTGACAAACATGGCCGCTGGTATGGAAGCTGGTATGGTCTTGGTCATGAGTTTGTGGGAC
GACTACGCCGTCAACATGCTCTGGCTCGACAGCACCTACCCTACAAACGCGACTGGTACCCC
CGGTGCCGCTCGTGGTACCTGCGCTACCACTTCTGGGGACCCCAAGACCGTTGAATCACAAT
CCGGCAGCTCCTATGTCACCTTCTCTGACATTCGGGTTGGTCCTTTCAATTCTACGTTCAGC
GGTGGTTCTAGCACCGGTGGCAGCACTACTACTACCGCCAGCCGCACCACCACCACCTCGGC
<u>CTCTTCCACCTCTACTTCCAGCACCTCTACTGGCACTGGA</u>**ACCCAGTCTCACTACGGCCAGT
GCGGCGGTATTGGCTACAGCGGCCCCACGGTCTGCGCCAGCGGCACAACTTGCCAGGTCCTG
AACCCTTACTACTCTCAGTGCCTG**

SEQ ID NO:6

QQIGTYTAETHPSLSWSTCKSGGSCTTNSGAITLDANWRWVHGVNTSTNCYTGNTWNSAICD
TDASCAQDCALDGADYSGTYGITTSGNSLRLNFVTGSNVGSRTYLMADNTHYQIFDLLNQEF
TFTVDVSHLPCGLNGALYFVTMDADGGVSKYPNNKAGAQYGVGYCDSQCPRDLKFIAGQANV
EGWTPSANNANTGIGNHGACCAELDIWEANSISEALTPHPCDTPGLSVCTTDACGGTYSSDR
YAGTCDPDGCDFNPYRLGVTDFYGSGKTVDTTKPFTVVTQFVTNDGTSTGSLSEIRRYYVQN
GVVIPQPSSKISGISGNVINSDYCAAEISTFGGTASFSKHGGLTNMAAGMEAGMVLVMSLWD
DYAVNMLWDSTYPTNATGTPGAARGTCATTSGDPKTVESQSGSSYVTFSDIRVGPFNSTFS
<u>GGSSTGGSTTTTASRTTTTSASSTSTSSTSTGTG</u>**TQSHYGQCGGIGYSGPTVCASGTTCQVL
NPYYSQCL**

Figure 5

SEQ ID NO:7

CAGCAAATTGGTACTTATACCGCTGAAACCCATCCCTCTCTGAGCTGGTCTACTTGCAAATC
GGGTGGTAGCTGCACCACAAACTCCGGTGCCATTACGTTAGATGCCAACTGGCGTTGGGTCC
ATGGTGTCAATACCAGCACCAACTGCTACACTGGCAACACTTGGAATAGCGCCATCTGCGAC
ACTGATGCATCCTGTGCCCAGGACTGTGCTCTCGATGGTGCTGACTACTCTGGCACGTACGG
TATCACTACCTCCGGCAACTCATTGCGCCTGAACTTCGTTACCGGTTCCAACGTCGGATCTC
GTACTTACCTGATGGCCGATAACACCCACTACCAAATCTTCGATCTGTTGAACCAGGAGTTC
ACCTTCACCGTCGATGTCTCCCACCTCCCTTGCGGTTTGAACGGTGCCCTCTACTTCGTGAC
CATGGATGCCGACGGTGGCGTCTCCAAGTACCCCAACAACAAGGCCGGTGCTCAGTACGGTG
TTGGATACTGTGACTCTCAATGCCCTCGTGACTTGAAGTTCATCGCTGGTCAGGCCAACGTT
GAGGGCTGGACGCCCTCCGCCAACAACGCCAACACTGGAATTGGCAATCACGGAGCTTGCTG
CGCGGAGCTTGATATCTGGGAGGCAAACAGCATCTCAGAGGCCTTGACTCCTCACCCTTGCG
ATACACCCGGTCTATCTGTTTGCACTACTGATGCCTGCGGTGGTACCTACAGCTCTGATCGT
TACGCCGGTACCTGCGACCCTGATGGATGTGACTTCAACCCTTACCGCCTTGGTGTCACTGA
CTTCTACGGCTCCGGCAAGACCGTTGACACCACCAAGCCCTTTACCGTTGTGACTCAATTCG
TCACTAACGACGGTACCTCCACCGGTTCCCTCTCCGAGATCAGACGTTACTACGTTCAGAAC
GGCGTTGTCATCCCCCAGCCTTCCTCCAAGATCTCCGGAATCAGCGGAAATGTCATCAACTC
CGACTACTGCGCTGCTGAAATTTCCACCTTTGGCGGGACTGCCTCCTTCAGCAAACACGGTG
GCTTGACAAACATGGCCGCTGGTATGGAAGCTGGTATGGTCTTGGTCATGAGTTTGTGGGAC
GACTACGCCGTCAACATGCTCTGGCTCGACAGCACCTACCCTACAAACGCGACTGGTACCCC
CGGTGCCGCTCGTGGTACCTGCGCTACCACTTCTGGGGACCCCAAGACCGTTGAATCACAAT
CCGGCAGCTCCTATGTCACCTTCTCTGACATTCGGGTTGGTCCTTTCAATTCTACGTTCAGC
GGCAACCCTCCCGGCGGAAACCCGCCTGGCACCACCACCACCCGCCGCCCAGCCACTACCAC
<u>TGGAAGCTCTCCCGGACCT</u>**ACCCAGTCTCACTACGGCCAGTGCGGCGGTATTGGCTACAGCG
GCCCCACGGTCTGCGCCAGCGGCACAACTTGCCAGGTCCTGAACCCTTACTACTCTCAGTGC
CTG**

SEQ ID NO:8

QQIGTYTAETHPSLSWSTCKSGGSCTTNSGAITLDANWRWVHGVNTSTNCYTGNTWNSAICD
TDASCAQDCALDGADYSGTYGITTSGNSLRLNFVTGSNVGSRTYLMADNTHYQIFDLLNQEF
TFTVDVSHLPCGLNGALYFVTMDADGGVSKYPNNKAGAQYGVGYCDSQCPRDLKFIAGQANV
EGWTPSANNANTGIGNHGACCAELDIWEANSISEALTPHPCDTPGLSVCTTDACGGTYSSDR
YAGTCDPDGCDFNPYRLGVTDFYGSGKTVDTTKPFTVVTQFVTNDGTSTGSLSEIRRYYVQN
GVVIPQPSSKISGISGNVINSDYCAAEISTFGGTASFSKHGGLTNMAAGMEAGMVLVMSLWD
DYAVNMLWLDSTYPTNATGTPGAARGTCATTSGDPKTVESQSGSSYVTFSDIRVGPFNSTFS
<u>GNPPGGNPPGTTTTRRPATTTGSSPGP</u>**TQSHYGQCGGIGYSGPTVCASGTTCQVLNPYYSQC
L**

Figure 6

SEQ ID NO:9

CAGTCGGCCTGCACTCTCCAATCGGAGACTCACCCGCCTCTGACATGGCAGAAATGCTCGTC
TGGTGGCACGTGCACTCAACAGACAGGCTCCGTGGTCATCGACGCCAACTGGCGCTGGACTC
ACGCTACGAACAGCAGCACGAACTGCTACGATGGCAACACTTGGAGCTCGACCCTATGTCCT
GACAACGAGACCTGCGCGAAGAACTGCTGTCTGGACGGTGCCGCCTACGCGTCCACGTACGG
AGTTACCACGAGCGGTAACAGCCTCTCCATTGGCTTTGTCACCCAGTCTGCGCAGAAGAACG
TTGGCGCTCGCCTTTACCTTATGGCGAGCGACACGACCTACCAGGAATTCACCCTGCTTGGC
AACGAGTTCTCTTTCGATGTTGATGTTTCGCAGCTGCCGTGCGGCTTGAACGGAGCTCTCTA
CTTCGTGTCCATGGACGCGGATGGTGGCGTGAGCAAGTATCCCACCAACACCGCTGGCGCCA
AGTACGGCACGGGGTACTGTGACAGCCAGTGTCCCGCGATCTGAAGTTCATCAATGGCCAG
GCCAACGTTGAGGGCTGGGAGCCGTCATCCAACAACGCGAACACGGGCATTGGAGGACACGG
AAGCTGCTGCTCTGAGATGGATATCTGGGAGGCCAACTCCATCTCCGAGGCTCTTACCCCCC
ACCCTTGCACGACTGTCGGCCAGGAGATCTGCGAGGGTGATGGGTGCGGCGGAACTTACTCC
GATAACAGATATGGCGGCACTTGCGATCCCGATGGCTGCGACTGGAACCCATACCGCCTGGG
CAACACCAGCTTCTACGGCCCTGGCTCAAGCTTTACCCTCGATACCACCAAGAAATTGACCG
TTGTCACCCAGTTCGAGACGTCGGGTGCCATCAACCGATACTATGTCCAGAATGGCGTCACT
TTCCAGCAGCCCAACGCCGAGCTTGGTAGTTACTCTGGCAACGAGCTCAACGATGATTACTG
CACAGCTGAGGAGGCAGAATTCGGCGGATCCTCTTTCTCAGACAAGGGCGGCCTGACTCAGT
TCAAGAAGGCTACCTCTGGCGGCATGGTTCTGGTCATGAGTCTGTGGGATGATTACTACGCC
AACATGCTGTGGCTGGACTCCACCTACCCGACAAACGAGACCTCCTCCACACCCGGTGCCGT
GCGCGGAAGCTGCTCCACCAGCTCCGGTGTCCCTGCTCAGGTCGAATCTCAGTCTCCCAACG
CCAAGGTCACCTTCTCCAACATCAAGTTCGGACCCATTGGCAGCACCGGCAACCCTAGCGGC
GGTGGTTCTAGCACCGGTGGCAGCACTACTACTACCGCCAGCCGCACCACCACCACCTCGGC
CTCTTCCACCTCTACTTCCAGCACCTCTACTGGCACTGGA**ACCAGTCTCACTACGGCCAGT
GCGGCGGTATTGGCTACAGCGGCCCCACGGTCTGCGCCAGCGGCACAACTTGCCAGGTCCTG
AACCCTTACTACTCTCAGTGCCTG**

SEQ ID NO:10

QSACTLQSETHPPLTWQKCSSGGTCTQQTGSVVIDANWRWTHATNSSTNCYDGNTWSSTLCP
DNETCAKNCCLDGAAYASTYGVTTSGNSLSIGFVTQSAQKNVGARLYLMASDTTYQEFTLLG
NEFSFDVDVSQLPCGLNGALYFVSMDADGGVSKYPTNTAGAKYGTGYCDSQCPRDLKFINGQ
ANVEGWEPSSNNANTGIGGHGSCCSEMDIWEANSISEALTPHPCTTVGQEICEGDGCGGTYS
DNRYGGTCDPDGCDWNPYRLGNTSFYGPGSSFTLDTTKKLTVVTQFETSGAINRYYVQNGVT
FQQPNAELGSYSGNELNDDYCTAEEAEFGGSSFSDKGGLTQFKKATSGGMVLVMSLWDDYYA
NMLWLDSTYPTNETSSTPGAVRGSCSTSSGVPAQVESQSPNAKVTFSNIKFGPIGSTGNPSG
GGSSTGGSTTTTASRTTTTSASSTSSTSTGTG**TQSHYGQCGGIGYSGPTVCASGTTCQVL
NPYYSQCL**

Figure 7

SEQ ID NO:11

CAGTCGGCCTGCACTCTCCAATCGGAGACTCACCCGCCTCTGACATGGCAGAAATGCTCGTC
TGGTGGCACGTGCACTCAACAGACAGGCTCCGTGGTCATCGACGCCAACTGGCGCTGGACTC
ACGCTACGAACAGCAGCACGAACTGCTACGATGGCAACACTTGGAGCTCGACCCTATGTCCT
GACAACGAGACCTGCGCGAAGAACTGCTGTCTGGACGGTGCCGCCTACGCGTCCACGTACGG
AGTTACCACGAGCGGTAACAGCCTCTCCATTGGCTTTGTCACCCAGTCTGCGCAGAAGAACG
TTGGCGCTCGCCTTTACCTTATGGCGAGCGACACGACCTACCAGGAATTCACCCTGCTTGGC
AACGAGTTCTCTTTCGATGTTGATGTTTCGCAGCTGCCGTGCGGCTTGAACGGAGCTCTCTA
CTTCGTGTCCATGGACGCGGATGGTGGCGTGAGCAAGTATCCCACCAACACCGCTGGCGCCA
AGTACGGCACGGGGTACTGTGACAGCCAGTGTCCCGCGATCTGAAGTTCATCAATGGCCAG
GCCAACGTTGAGGGCTGGGAGCCGTCATCCAACAACGCGAACACGGGCATTGGAGGACACGG
AAGCTGCTGCTCTGAGATGGATATCTGGAGGCCAACTCCATCTCCGAGGCTCTTACCCCCC
ACCCTTGCACGACTGTCGGCCAGGAGATCTGCGAGGGTGATGGGTGCGGCGGAACTTACTCC
GATAACAGATATGGCGGCACTTGCGATCCCGATGGCTGCGACTGGAACCCATACCGCCTGGG
CAACACCAGCTTCTACGGCCCTGGCTCAAGCTTTACCCTCGATACCACCAAGAAATTGACCG
TTGTCACCCAGTTCGAGACGTCGGGTGCCATCAACCGATACTATGTCCAGAATGGCGTCACT
TTCCAGCAGCCCAACGCCGAGCTTGGTAGTTACTCTGGCAACGAGCTCAACGATGATTACTG
CACAGCTGAGGAGGCAGAATTCGGCGGATCCTCTTTCTCAGACAAGGGCGGCCTGACTCAGT
TCAAGAAGGCTACCTCTGGCGGCATGGTTCTGGTCATGAGTCTGTGGGATGATTACTACGCC
AACATGCTGTGGCTGGACTCCACCTACCCGACAAACGAGACCTCCTCCACACCCGGTGCCGT
GCGCGGAAGCTGCTCCACCAGCTCCGGTGTCCCTGCTCAGGTCGAATCTCAGTCTCCCAACG
CCAAGGTCACCTTCTCCAACATCAAGTTCGGACCCATTGGCAGCACCGGCAACCCTAGCGGC
GGCAACCCTCCCGGCGGAAACCCGCCTGGCACCACCACCACCCGCCGCCCAGCCACTACCAC
TGGAAGCTCTCCCGGACCT**GTCGCTGGTCACTGGGGTCAGTGTGGTGGCCAGGGCTGGACTG
GCCCTACCACCTGTGTTAGTGGAACCACATGCACCGTCGTGAACCCTTACTACTCTCAATGT
TTG**

SEQ ID NO:12

QSACTLQSETHPPLTWQKCSSGGTCTQQTGSVVIDANWRWTHATNSSTNCYDGNTWSSTLCP
DNETCAKNCCLDGAAYASTYGVTTSGNSLSIGFVTQSAQKNVGARLYLMASDTTYQEFTLLG
NEFSFDVDVSQLPCGLNGALYFVSMDADGGVSKYPTNTAGAKYGTGYCDSQCPRDLKFINGQ
ANVEGWEPSSNNANTGIGGHGSCCSEMDIWEANSISEALTPHPCTTVGQEICEGDGCGGTYS
DNRYGGTCDPDGCDWNPYRLGNTSFYGPGSSFTLDTTKKLTVVTQFETSGAINRYYVQNGVT
FQQPNAELGSYSGNELNDDYCTAEEAEFGGSSFSDKGGLTQFKKATSGGMVLVMSLWDDYYA
NMLWLDSTYPTNETSSTPGAVRGSCSTSSGVPAQVESQSPNAKVTFSNIKFGPIGSTGNPSG
GNPPGGNPPGTTTTRRPATTTGSSPGP**VAGHWGQCGGQGWTGPTTCVSGTTCTVVNPYYSQC
L**

Figure 8

SEQ ID NO:13

CAGTCGGCCTGCACTCTCCAATCGGAGACTCACCCGCCTCTGACATGGCAGAAATGCTCGTC
TGGTGGCACGTGCACTCAACAGACAGGCTCCGTGGTCATCGACGCCAACTGGCGCTGGACTC
ACGCTACGAACAGCAGCACGAACTGCTACGATGGCAACACTTGGAGCTCGACCCTATGTCCT
GACAACGAGACCTGCGCGAAGAACTGCTGTCTGGACGGTGCCGCCTACGCGTCCACGTACGG
AGTTACCACGAGCGGTAACAGCCTCTCCATTGGCTTTGTCACCCAGTCTGCGCAGAAGAACG
TTGGCGCTCGCCTTTACCTTATGGCGAGCGACACGACCTACCAGGAATTCACCCTGCTTGGC
AACGAGTTCTCTTTCGATGTTGATGTTTCGCAGCTGCCGTGCGGCTTGAACGGAGCTCTCTA
CTTCGTGTCCATGGACGCGGATGGTGGCGTGAGCAAGTATCCCACCAACACCGCTGGCGCCA
AGTACGGCACGGGGTACTGTGACAGCCAGTGTCCCCGCGATCTGAAGTTCATCAATGGCCAG
GCCAACGTTGAGGGCTGGGAGCCGTCATCCAACAACGCGAACACGGGCATTGGAGGACACGG
AAGCTGCTGCTCTGAGATGGATATCTGGGAGGCCAACTCCATCTCCGAGGCTCTTACCCCCC
ACCCTTGCACGACTGTCGGCCAGGAGATCTGCGAGGGTGATGGGTGCGGCGGAACTTACTCC
GATAACAGATATGGCGGCACTTGCGATCCCGATGGCTGCGACTGGAACCCATACCGCCTGGG
CAACACCAGCTTCTACGGCCCTGGCTCAAGCTTTACCCTCGATACCACCAAGAAATTGACCG
TTGTCACCCAGTTCGAGACGTCGGGTGCCATCAACCGATACTATGTCCAGAATGGCGTCACT
TTCCAGCAGCCCAACGCCGAGCTTGGTAGTTACTCTGGCAACGAGCTCAACGATGATTACTG
CACAGCTGAGGAGGCAGAATTCGGCGGATCCTCTTTCTCAGACAAGGGCGGCCTGACTCAGT
TCAAGAAGGCTACCTCTGGCGGCATGGTTCTGGTCATGAGTCTGTGGGATGATTACTACGCC
AACATGCTGTGGCTGGACTCCACCTACCCGACAAACGAGACCTCCTCCACACCCGGTGCCGT
GCGCGGAAGCTGCTCCACCAGCTCCGGTGTCCCTGCTCAGGTCGAATCTCAGTCTCCCAACG
CCAAGGTCACCTTCTCCAACATCAAGTTCGGACCCATTGGCAGCACCGGCAACCCTAGCGGC
GGTGGTTCTAGCACCGGTGGCAGCACTACTACTACCGCCAGCCGCACCACCACCACCTCGGC
CTCTTCCACCTCTACTTCCAGCACCTCTACTGGCACTGGA**GTCGCTGGTCACTGGGGTCAGT
GTGGTGGCCAGGGCTGGACTGGCCCTACCACCTGTGTTAGTGGAACCACATGCACCGTCGTG
AACCCTTACTACTCTCAATGTTTG**

SEQ ID NO:14

QSACTLQSETHPPLTWQKCSSGGTCTQQTGSVVIDANWRWTHATNSSTNCYDGNTWSSTLCP
DNETCAKNCCLDGAAYASTYGVTTSGNSLSIGFVTQSAQKNVGARLYLMASDTTYQEFTLLG
NEFSFDVDVSQLPCGLNGALYFVSMDADGGVSKYPTNTAGAKYGTGYCDSQCPRDLKFINGQ
ANVEGWEPSSNNANTGIGGHGSCCSEMDIWEANSISEALTPHPCTTVGQEICEGDGCGGTYS
DNRYGGTCDPDGCDWNPYRLGNTSFYGPGSSFTLDTTKKLTVVTQFETSGAINRYYVQNGVT
FQQPNAELGSYSGNELNDDYCTAEEAEFGGSSFSDKGGLTQFKKATSGGMVLVMSLWDDYYA
NMLWLDSTYPTNETSSTPGAVRGSCSTSSGVPAQVESQSPNAKVTFSNIKFGPIGSTGNPSG
GGSSTGGSTTTTASRTTTTSASSTSTSSTSTGTG**VAGHWGQCGGQGWTGPTTCVSGTTCTVV
NPYYSQCL**

Figure 9

SEQ ID NO:15

CAGCAAATTGGTACTTATACCGCTGAAACCCATCCCTCTCTGAGCTGGTCTACTTGCAAATC
GGGTGGTAGCTGCACCACAAACTCCGGTGCCATTACGTTAGATGCCAACTGGCGTTGGGTCC
ATGGTGTCAATACCAGCACCAACTGCTACACTGGCAACACTTGGAATAGCGCCATCTGCGAC
ACTGATGCATCCTGTGCCCAGGACTGTGCTCTCGATGGTGCTGACTACTCTGGCACGTACGG
TATCACTACCTCCGGCAACTCATTGCGCCTGAACTTCGTTACCGGTTCCAACGTCGGATCTC
GTACTTACCTGATGGCCGATAACACCCACTACCAAATCTTCGATCTGTTGAACCAGGAGTTC
ACCTTCACCGTCGATGTCTCCCACCTCCCTTGCGGTTTGAACGGTGCCCTCTACTTCGTGAC
CATGGATGCCGACGGTGGCGTCTCCAAGTACCCCAACAACAAGGCCGGTGCTCAGTACGGTG
TTGGATACTGTGACTCTCAATGCCCTCGTGACTTGAAGTTCATCGCTGGTCAGGCCAACGTT
GAGGGCTGGACGCCCTCCGCCAACAACGCCAACACTGGAATTGGCAATCACGGAGCTTGCTG
CGCGGAGCTTGATATCTGGGAGGCAAACAGCATCTCAGAGGCCTTGACTCCTCACCCTTGCG
ATACACCCGGTCTATCTGTTTGCACTACTGATGCCTGCGGTGGTACCTACAGCTCTGATCGT
TACGCCGGTACCTGCGACCCTGATGGATGTGACTTCAACCCTTACCGCCTTGGTGTCACTGA
CTTCTACGGCTCCGGCAAGACCGTTGACACCACCAAGCCCTTTACCGTTGTGACTCAATTCG
TCACTAACGACGGTACCTCCACCGGTTCCCTCTCCGAGATCAGACGTTACTACGTTCAGAAC
GGCGTTGTCATCCCCCAGCCTTCCTCCAAGATCTCCGGAATCAGCGGAAATGTCATCAACTC
CGACTACTGCGCTGCTGAAATTTCCACCTTTGGCGGGACTGCCTCCTTCAGCAAACACGGTG
GCTTGACAAACATGGCCGCTGGTATGGAAGCTGGTATGGTCTTGGTCATGAGTTTGTGGGAC
GACTACGCCGTCAACATGCTCTGGCTCGACAGCACCTACCCTACAAACGCGACTGGTACCCC
CGGTGCCGCTCGTGGTACCTGCGCTACCACTTCTGGGGACCCCAAGACCGTTGAATCACAAT
CCGGCAGCTCCTATGTCACCTTCTCTGACATTCGGGTTGGTCCTTTCAATTCTACGTTCAGC
GGCAACCCTCCCGGCGGAAACCCGCCTGGCACCACCACCACCCGCCGCCCAGCCACTACCAC
TGGAAGCTCTCCCGGACCT**GTCGCTGGTCACTGGGGTCAGTGTGGTGGCCAGGGCTGGACTG
GCCCTACCACCTGTGTTAGTGGAACCACATGCACCGTCGTGAACCCTTACTACTCTCAATGT
TTG**

SEQ ID NO:16

QQIGTYTAETHPSLSWSTCKSGGSCTTNSGAITLDANWRWVHGVNTSTNCYTGNTWNSAICD
TDASCAQDCALDGADYSGTYGITTSGNSLRLNFVTGSNVGSRTYLMADNTHYQIFDLLNQEF
TFTVDVSHLPCGLNGALYFVTMDADGGVSKYPNNKAGAQYGVGYCDSQCPRDLKFIAGQANV
EGWTPSANNANTGIGNHGACCAELDIWEANSISEALTPHPCDTPGLSVCTTDACGGTYSSDR
YAGTCDPDGCDFNPYRLGVTDFYGSGKTVDTTKPFTVVTQFVTNDGTSTGSLSEIRRYYVQN
GVVIPQPSSKISGISGNVINSDYCAAEISTFGGTASFSKHGGLTNMAAGMEAGMVLVMSLWD
DYAVNMLWLDSTYPTNATGTPGAARGTCATTSGDPKTVESQSGSSYVTFSDIRVGPFNSTFS
GNPPGGNPPGTTTTRRPATTTGSSPGP**VAGHWGQCGGQGWTGPTTCVSGTTCTVVNPYYSQC
L**

SEQUENCE LISTING

```
<160> NUMBER OF SEQ ID NOS: 28

<210> SEQ ID NO 1
<211> LENGTH: 1512
<212> TYPE: DNA
<213> ORGANISM: Penicillium funiculosum
<220> FEATURE:
<221> NAME/KEY: CDS
<222> LOCATION: (1)..(1512)

<400> SEQUENCE: 1 cag caa att ggt act tat acc gct gaa acc cat ccc tct ctg agc tgg      48
Gln Gln Ile Gly Thr Tyr Thr Ala Glu Thr His Pro Ser Leu Ser Trp
1               5                   10                  15 tct act tgc aaa tcg ggt ggt agc tgc acc aca aac tcc ggt gcc att      96
Ser Thr Cys Lys Ser Gly Gly Ser Cys Thr Thr Asn Ser Gly Ala Ile
            20                  25                  30 acg tta gat gcc aac tgg cgt tgg gtc cat ggt gtc aat acc agc acc     144
Thr Leu Asp Ala Asn Trp Arg Trp Val His Gly Val Asn Thr Ser Thr
        35                  40                  45 aac tgc tac act ggc aac act tgg aat agc gcc atc tgc gac act gat     192
Asn Cys Tyr Thr Gly Asn Thr Trp Asn Ser Ala Ile Cys Asp Thr Asp
```

```
                50                  55                  60
gca tcc tgt gcc cag gac tgt gct ctc gat ggt gct gac tac tct ggc       240
Ala Ser Cys Ala Gln Asp Cys Ala Leu Asp Gly Ala Asp Tyr Ser Gly
 65                  70                  75                  80 acg tac ggt atc act acc tcc ggc aac tca ttg cgc ctg aac ttc gtt       288
Thr Tyr Gly Ile Thr Thr Ser Gly Asn Ser Leu Arg Leu Asn Phe Val
                     85                  90                  95 acc ggt tcc aac gtc gga tct cgt act tac ctg atg gcc gat aac acc       336
Thr Gly Ser Asn Val Gly Ser Arg Thr Tyr Leu Met Ala Asp Asn Thr
                100                 105                 110 cac tac caa atc ttc gat ctg ttg aac cag gag ttc acc ttc acc gtc       384
His Tyr Gln Ile Phe Asp Leu Leu Asn Gln Glu Phe Thr Phe Thr Val
                115                 120                 125 gat gtc tcc cac ctc cct tgc ggt ttg aac ggt gcc ctc tac ttc gtg       432
Asp Val Ser His Leu Pro Cys Gly Leu Asn Gly Ala Leu Tyr Phe Val
130                 135                 140 acc atg gat gcc gac ggt ggc gtc tcc aag tac ccc aac aac aag gcc       480
Thr Met Asp Ala Asp Gly Gly Val Ser Lys Tyr Pro Asn Asn Lys Ala
145                 150                 155                 160 ggt gct cag tac ggt gtt gga tac tgt gac tct caa tgc cct cgt gac       528
Gly Ala Gln Tyr Gly Val Gly Tyr Cys Asp Ser Gln Cys Pro Arg Asp
                165                 170                 175 ttg aag ttc atc gct ggt cag gcc aac gtt gag ggc tgg acg ccc tcc       576
Leu Lys Phe Ile Ala Gly Gln Ala Asn Val Glu Gly Trp Thr Pro Ser
                180                 185                 190 gcc aac aac gcc aac act gga att ggc aat cac gga gct tgc tgc gcg       624
Ala Asn Asn Ala Asn Thr Gly Ile Gly Asn His Gly Ala Cys Cys Ala
                195                 200                 205 gag ctt gat atc tgg gag gca aac agc atc tca gag gcc ttg act cct       672
Glu Leu Asp Ile Trp Glu Ala Asn Ser Ile Ser Glu Ala Leu Thr Pro
210                 215                 220 cac cct tgc gat aca ccc ggt cta tct gtt tgc act act gat gcc tgc       720
His Pro Cys Asp Thr Pro Gly Leu Ser Val Cys Thr Thr Asp Ala Cys
225                 230                 235                 240 ggt ggt acc tac agc tct gat cgt tac gcc ggt acc tgc gac cct gat       768
Gly Gly Thr Tyr Ser Ser Asp Arg Tyr Ala Gly Thr Cys Asp Pro Asp
                245                 250                 255 gga tgt gac ttc aac cct tac cgc ctt ggt gtc act gac ttc tac ggc       816
Gly Cys Asp Phe Asn Pro Tyr Arg Leu Gly Val Thr Asp Phe Tyr Gly
                260                 265                 270 tcc ggc aag acc gtt gac acc acc aag ccc ttt acc gtt gtg act caa       864
Ser Gly Lys Thr Val Asp Thr Thr Lys Pro Phe Thr Val Val Thr Gln
                275                 280                 285 ttc gtc act aac gac ggt acc tcc acc ggt tcc ctc tcc gag atc aga       912
Phe Val Thr Asn Asp Gly Thr Ser Thr Gly Ser Leu Ser Glu Ile Arg
                290                 295                 300 cgt tac tac gtt cag aac ggt gtt gtc atc ccc cag cct tcc tcc aag       960
Arg Tyr Tyr Val Gln Asn Gly Val Val Ile Pro Gln Pro Ser Ser Lys
305                 310                 315                 320 atc tcc gga atc agc gga aat gtc atc aac tcc gac tac tgc gct gct      1008
Ile Ser Gly Ile Ser Gly Asn Val Ile Asn Ser Asp Tyr Cys Ala Ala
                325                 330                 335 gaa att tcc acc ttt ggc ggg act gcc tcc ttc agc aaa cac ggt ggc      1056
Glu Ile Ser Thr Phe Gly Gly Thr Ala Ser Phe Ser Lys His Gly Gly
                340                 345                 350 ttg aca aac atg gcc gct ggt atg gaa gct ggt atg gtc ttg gtc atg      1104
Leu Thr Asn Met Ala Ala Gly Met Glu Ala Gly Met Val Leu Val Met
                355                 360                 365 agt ttg tgg gac gac tac gcc gtc aac atg ctc tgg ctc gac agc acc      1152
```

```
Ser Leu Trp Asp Asp Tyr Ala Val Asn Met Leu Trp Leu Asp Ser Thr
    370                 375                 380 tac cct aca aac gcg act ggt acc ccc ggt gcc gct cgt ggt acc tgc      1200
Tyr Pro Thr Asn Ala Thr Gly Thr Pro Gly Ala Ala Arg Gly Thr Cys
385                 390                 395                 400 gct acc act tct ggg gac ccc aag acc gtt gaa tca caa tcc ggc agc      1248
Ala Thr Thr Ser Gly Asp Pro Lys Thr Val Glu Ser Gln Ser Gly Ser
                    405                 410                 415 tcc tat gtc acc ttc tct gac att cgg gtt ggt cct ttc aat tct acg      1296
Ser Tyr Val Thr Phe Ser Asp Ile Arg Val Gly Pro Phe Asn Ser Thr
                420                 425                 430 ttc agc ggt ggt tct agc acc ggt ggc agc act act act acc gcc agc      1344
Phe Ser Gly Gly Ser Ser Thr Gly Gly Ser Thr Thr Thr Thr Ala Ser
            435                 440                 445 cgc acc acc acc acc tcg gcc tct tcc acc tct act tcc agc acc tct      1392
Arg Thr Thr Thr Thr Ser Ala Ser Ser Thr Ser Thr Ser Ser Thr Ser
        450                 455                 460 act ggc act gga gtc gct ggt cac tgg ggt cag tgt ggt ggc cag ggc      1440
Thr Gly Thr Gly Val Ala Gly His Trp Gly Gln Cys Gly Gly Gln Gly
465                 470                 475                 480 tgg act ggc cct acc acc tgt gtt agt gga acc aca tgc acc gtc gtg      1488
Trp Thr Gly Pro Thr Thr Cys Val Ser Gly Thr Thr Cys Thr Val Val
                    485                 490                 495 aac cct tac tac tct caa tgt ttg                                      1512
Asn Pro Tyr Tyr Ser Gln Cys Leu
                500

<210> SEQ ID NO 2
<211> LENGTH: 504
<212> TYPE: PRT
<213> ORGANISM: Penicillium funiculosum

<400> SEQUENCE: 2

Gln Gln Ile Gly Thr Tyr Thr Ala Glu Thr His Pro Ser Leu Ser Trp
1               5                   10                  15

Ser Thr Cys Lys Ser Gly Gly Ser Cys Thr Thr Asn Ser Gly Ala Ile
                20                  25                  30

Thr Leu Asp Ala Asn Trp Arg Trp Val His Gly Val Asn Thr Ser Thr
            35                  40                  45

Asn Cys Tyr Thr Gly Asn Thr Trp Asn Ser Ala Ile Cys Asp Thr Asp
 50                 55                  60

Ala Ser Cys Ala Gln Asp Cys Ala Leu Asp Gly Ala Asp Tyr Ser Gly
65                  70                  75                  80

Thr Tyr Gly Ile Thr Thr Ser Gly Asn Ser Leu Arg Leu Asn Phe Val
                85                  90                  95

Thr Gly Ser Asn Val Gly Ser Arg Thr Tyr Leu Met Ala Asp Asn Thr
            100                 105                 110

His Tyr Gln Ile Phe Asp Leu Leu Asn Gln Glu Phe Thr Phe Thr Val
        115                 120                 125

Asp Val Ser His Leu Pro Cys Gly Leu Asn Gly Ala Leu Tyr Phe Val
    130                 135                 140

Thr Met Asp Ala Asp Gly Gly Val Ser Lys Tyr Pro Asn Asn Lys Ala
145                 150                 155                 160

Gly Ala Gln Tyr Gly Val Gly Tyr Cys Asp Ser Gln Cys Pro Arg Asp
                165                 170                 175

Leu Lys Phe Ile Ala Gly Gln Ala Asn Val Glu Gly Trp Thr Pro Ser
            180                 185                 190
```

```
Ala Asn Asn Ala Asn Thr Gly Ile Gly Asn His Gly Ala Cys Cys Ala
        195                 200                 205

Glu Leu Asp Ile Trp Glu Ala Asn Ser Ile Ser Glu Ala Leu Thr Pro
    210                 215                 220

His Pro Cys Asp Thr Pro Gly Leu Ser Val Cys Thr Asp Ala Cys
225                 230                 235                 240

Gly Gly Thr Tyr Ser Ser Asp Arg Tyr Ala Gly Thr Cys Asp Pro Asp
                245                 250                 255

Gly Cys Asp Phe Asn Pro Tyr Arg Leu Gly Val Thr Asp Phe Tyr Gly
            260                 265                 270

Ser Gly Lys Thr Val Asp Thr Thr Lys Pro Phe Thr Val Val Thr Gln
        275                 280                 285

Phe Val Thr Asn Asp Gly Thr Ser Thr Gly Ser Leu Ser Glu Ile Arg
    290                 295                 300

Arg Tyr Tyr Val Gln Asn Gly Val Val Ile Pro Gln Pro Ser Ser Lys
305                 310                 315                 320

Ile Ser Gly Ile Ser Gly Asn Val Ile Asn Ser Asp Tyr Cys Ala Ala
                325                 330                 335

Glu Ile Ser Thr Phe Gly Gly Thr Ala Ser Phe Ser Lys His Gly Gly
            340                 345                 350

Leu Thr Asn Met Ala Ala Gly Met Glu Ala Gly Met Val Leu Val Met
        355                 360                 365

Ser Leu Trp Asp Asp Tyr Ala Val Asn Met Leu Trp Leu Asp Ser Thr
    370                 375                 380

Tyr Pro Thr Asn Ala Thr Gly Thr Pro Gly Ala Ala Arg Gly Thr Cys
385                 390                 395                 400

Ala Thr Thr Ser Gly Asp Pro Lys Thr Val Glu Ser Gln Ser Gly Ser
                405                 410                 415

Ser Tyr Val Thr Phe Ser Asp Ile Arg Val Gly Pro Phe Asn Ser Thr
            420                 425                 430

Phe Ser Gly Gly Ser Ser Thr Gly Gly Ser Thr Thr Thr Ala Ser
        435                 440                 445

Arg Thr Thr Thr Ser Ala Ser Ser Thr Ser Thr Ser Ser Thr Ser
450                 455                 460

Thr Gly Thr Gly Val Ala Gly His Trp Gly Gln Cys Gly Gly Gln Gly
465                 470                 475                 480

Trp Thr Gly Pro Thr Thr Cys Val Ser Gly Thr Thr Cys Thr Val Val
                485                 490                 495

Asn Pro Tyr Tyr Ser Gln Cys Leu
            500

<210> SEQ ID NO 3
<211> LENGTH: 1491
<212> TYPE: DNA
<213> ORGANISM: Trichoderma reesei
<220> FEATURE:
<221> NAME/KEY: CDS
<222> LOCATION: (1)..(1491)

<400> SEQUENCE: 3 cag tcg gcc tgc act ctc caa tcg gag act cac ccg cct ctg aca tgg      48
Gln Ser Ala Cys Thr Leu Gln Ser Glu Thr His Pro Pro Leu Thr Trp
1               5                   10                  15 cag aaa tgc tcg tct ggt ggc acg tgc act caa cag aca ggc tcc gtg      96
Gln Lys Cys Ser Ser Gly Gly Thr Cys Thr Gln Gln Thr Gly Ser Val
            20                  25                  30
```

```
gtc atc gac gcc aac tgg cgc tgg act cac gct acg aac agc agc acg      144
Val Ile Asp Ala Asn Trp Arg Trp Thr His Ala Thr Asn Ser Ser Thr
        35                  40                  45 aac tgc tac gat ggc aac act tgg agc tcg acc cta tgt cct gac aac      192
Asn Cys Tyr Asp Gly Asn Thr Trp Ser Ser Thr Leu Cys Pro Asp Asn
 50                  55                  60 gag acc tgc gcg aag aac tgc tgt ctg gac ggt gcc gcc tac gcg tcc      240
Glu Thr Cys Ala Lys Asn Cys Cys Leu Asp Gly Ala Ala Tyr Ala Ser
 65                  70                  75                  80 acg tac gga gtt acc acg agc ggt aac agc ctc tcc att ggc ttt gtc      288
Thr Tyr Gly Val Thr Thr Ser Gly Asn Ser Leu Ser Ile Gly Phe Val
                 85                  90                  95 acc cag tct gcg cag aag aac gtt ggc gct cgc ctt tac ctt atg gcg      336
Thr Gln Ser Ala Gln Lys Asn Val Gly Ala Arg Leu Tyr Leu Met Ala
            100                 105                 110 agc gac acg acc tac cag gaa ttc acc ctg ctt ggc aac gag ttc tct      384
Ser Asp Thr Thr Tyr Gln Glu Phe Thr Leu Leu Gly Asn Glu Phe Ser
        115                 120                 125 ttc gat gtt gat gtt tcg cag ctg ccg tgc ggc ttg aac gga gct ctc      432
Phe Asp Val Asp Val Ser Gln Leu Pro Cys Gly Leu Asn Gly Ala Leu
130                 135                 140 tac ttc gtg tcc atg gac gcg gat ggt ggc gtg agc aag tat ccc acc      480
Tyr Phe Val Ser Met Asp Ala Asp Gly Gly Val Ser Lys Tyr Pro Thr
145                 150                 155                 160 aac acc gct ggc gcc aag tac ggc acg ggg tac tgt gac agc cag tgt      528
Asn Thr Ala Gly Ala Lys Tyr Gly Thr Gly Tyr Cys Asp Ser Gln Cys
                165                 170                 175 ccc cgc gat ctg aag ttc atc aat ggc cag gcc aac gtt gag ggc tgg      576
Pro Arg Asp Leu Lys Phe Ile Asn Gly Gln Ala Asn Val Glu Gly Trp
            180                 185                 190 gag ccg tca tcc aac aac gcg aac acg ggc att gga gga cac gga agc      624
Glu Pro Ser Ser Asn Asn Ala Asn Thr Gly Ile Gly Gly His Gly Ser
        195                 200                 205 tgc tgc tct gag atg gat atc tgg gag gcc aac tcc atc tcc gag gct      672
Cys Cys Ser Glu Met Asp Ile Trp Glu Ala Asn Ser Ile Ser Glu Ala
210                 215                 220 ctt acc ccc cac cct tgc acg act gtc ggc cag gag atc tgc gag ggt      720
Leu Thr Pro His Pro Cys Thr Thr Val Gly Gln Glu Ile Cys Glu Gly
225                 230                 235                 240 gat ggg tgc ggc gga act tac tcc gat aac aga tat ggc ggc act tgc      768
Asp Gly Cys Gly Gly Thr Tyr Ser Asp Asn Arg Tyr Gly Gly Thr Cys
                245                 250                 255 gat ccc gat ggc tgc gac tgg aac cca tac cgc ctg ggc aac acc agc      816
Asp Pro Asp Gly Cys Asp Trp Asn Pro Tyr Arg Leu Gly Asn Thr Ser
            260                 265                 270 ttc tac ggc cct ggc tca agc ttt acc ctc gat acc acc aag aaa ttg      864
Phe Tyr Gly Pro Gly Ser Ser Phe Thr Leu Asp Thr Thr Lys Lys Leu
        275                 280                 285 acc gtt gtc acc cag ttc gag acg tcg ggt gcc atc aac cga tac tat      912
Thr Val Val Thr Gln Phe Glu Thr Ser Gly Ala Ile Asn Arg Tyr Tyr
290                 295                 300 gtc cag aat ggc gtc act ttc cag cag ccc aac gcc gag ctt ggt agt      960
Val Gln Asn Gly Val Thr Phe Gln Gln Pro Asn Ala Glu Leu Gly Ser
305                 310                 315                 320 tac tct ggc aac gag ctc aac gat gat tac tgc aca gct gag gag gca     1008
Tyr Ser Gly Asn Glu Leu Asn Asp Asp Tyr Cys Thr Ala Glu Glu Ala
                325                 330                 335 gaa ttc ggc gga tcc tct ttc tca gac aag ggc ggc ctg act cag ttc     1056
Glu Phe Gly Gly Ser Ser Phe Ser Asp Lys Gly Gly Leu Thr Gln Phe
            340                 345                 350
```

```
aag aag gct acc tct ggc ggc atg gtt ctg gtc atg agt ctg tgg gat    1104
Lys Lys Ala Thr Ser Gly Gly Met Val Leu Val Met Ser Leu Trp Asp
        355                 360                 365 gat tac tac gcc aac atg ctg tgg ctg gac tcc acc tac ccg aca aac    1152
Asp Tyr Tyr Ala Asn Met Leu Trp Leu Asp Ser Thr Tyr Pro Thr Asn
370                 375                 380 gag acc tcc tcc aca ccc ggt gcc gtg cgc gga agc tgc tcc acc agc    1200
Glu Thr Ser Ser Thr Pro Gly Ala Val Arg Gly Ser Cys Ser Thr Ser
385                 390                 395                 400 tcc ggt gtc cct gct cag gtc gaa tct cag tct ccc aac gcc aag gtc    1248
Ser Gly Val Pro Ala Gln Val Glu Ser Gln Ser Pro Asn Ala Lys Val
                405                 410                 415 acc ttc tcc aac atc aag ttc gga ccc att ggc agc acc ggc aac cct    1296
Thr Phe Ser Asn Ile Lys Phe Gly Pro Ile Gly Ser Thr Gly Asn Pro
            420                 425                 430 agc ggc ggc aac cct ccc ggc gga aac ccg cct ggc acc acc acc acc    1344
Ser Gly Gly Asn Pro Pro Gly Gly Asn Pro Pro Gly Thr Thr Thr Thr
        435                 440                 445 cgc cgc cca gcc act acc act gga agc tct ccc gga cct acc cag tct    1392
Arg Arg Pro Ala Thr Thr Thr Gly Ser Ser Pro Gly Pro Thr Gln Ser
    450                 455                 460 cac tac ggc cag tgc ggt ggt att ggc tac agc ggc ccc acg gtc tgc    1440
His Tyr Gly Gln Cys Gly Gly Ile Gly Tyr Ser Gly Pro Thr Val Cys
465                 470                 475                 480 gcc agc ggc aca act tgc cag gtc ctg aac cct tac tac tct cag tgc    1488
Ala Ser Gly Thr Thr Cys Gln Val Leu Asn Pro Tyr Tyr Ser Gln Cys
                485                 490                 495 ctg                                                                1491
Leu

<210> SEQ ID NO 4
<211> LENGTH: 497
<212> TYPE: PRT
<213> ORGANISM: Trichoderma reesei

<400> SEQUENCE: 4

Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Gln Thr Gly Ser Val
            20                  25                  30

Val Ile Asp Ala Asn Trp Arg Trp Thr His Ala Thr Asn Ser Ser Thr
        35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Gly Asn Ser Leu Ser Ile Gly Phe Val
                85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
    130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
```

165                 170                 175
Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
            195                 200                 205

Cys Cys Ser Glu Met Asp Ile Trp Glu Ala Asn Ser Ile Ser Glu Ala
210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                245                 250                 255

Asp Pro Asp Gly Cys Asp Trp Asn Pro Tyr Arg Leu Gly Asn Thr Ser
                260                 265                 270

Phe Tyr Gly Pro Gly Ser Ser Phe Thr Leu Asp Thr Thr Lys Lys Leu
                275                 280                 285

Thr Val Val Thr Gln Phe Glu Thr Ser Gly Ala Ile Asn Arg Tyr Tyr
            290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335

Glu Phe Gly Gly Ser Ser Phe Ser Asp Lys Gly Gly Leu Thr Gln Phe
                340                 345                 350

Lys Lys Ala Thr Ser Gly Gly Met Val Leu Val Met Ser Leu Trp Asp
                355                 360                 365

Asp Tyr Tyr Ala Asn Met Leu Trp Leu Asp Ser Thr Tyr Pro Thr Asn
            370                 375                 380

Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
                405                 410                 415

Thr Phe Ser Asn Ile Lys Phe Gly Pro Ile Gly Ser Thr Gly Asn Pro
                420                 425                 430

Ser Gly Gly Asn Pro Pro Gly Gly Asn Pro Pro Gly Thr Thr Thr Thr
                435                 440                 445

Arg Arg Pro Ala Thr Thr Thr Gly Ser Ser Pro Gly Pro Thr Gln Ser
            450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
                485                 490                 495

Leu

<210> SEQ ID NO 5
<211> LENGTH: 1512
<212> TYPE: DNA
<213> ORGANISM: Artificial Sequence
<220> FEATURE:
<223> OTHER INFORMATION: Chimera of Penicillium funiculosum and
      Trichoderma reesei DNA sequences
<220> FEATURE:
<221> NAME/KEY: CDS
<222> LOCATION: (1)..(1512)

<400> SEQUENCE: 5 cag caa att ggt act tat acc gct gaa acc cat ccc tct ctg agc tgg         48

```
                Gln Gln Ile Gly Thr Tyr Thr Ala Glu Thr His Pro Ser Leu Ser Trp
                1               5                   10                  15 tct act tgc aaa tcg ggt ggt agc tgc acc aca aac tcc ggt gcc att              96
Ser Thr Cys Lys Ser Gly Gly Ser Cys Thr Thr Asn Ser Gly Ala Ile
                20                  25                  30 acg tta gat gcc aac tgg cgt tgg gtc cat ggt gtc aat acc agc acc            144
Thr Leu Asp Ala Asn Trp Arg Trp Val His Gly Val Asn Thr Ser Thr
            35                  40                  45 aac tgc tac act ggc aac act tgg aat agc gcc atc tgc gac act gat            192
Asn Cys Tyr Thr Gly Asn Thr Trp Asn Ser Ala Ile Cys Asp Thr Asp
        50                  55                  60 gca tcc tgt gcc cag gac tgt gct ctc gat ggt gct gac tac tct ggc            240
Ala Ser Cys Ala Gln Asp Cys Ala Leu Asp Gly Ala Asp Tyr Ser Gly
65                  70                  75                  80 acg tac ggt atc act acc tcc ggc aac tca ttg cgc ctg aac ttc gtt            288
Thr Tyr Gly Ile Thr Thr Ser Gly Asn Ser Leu Arg Leu Asn Phe Val
                85                  90                  95 acc ggt tcc aac gtc gga tct cgt act tac ctg atg gcc gat aac acc            336
Thr Gly Ser Asn Val Gly Ser Arg Thr Tyr Leu Met Ala Asp Asn Thr
                100                 105                 110 cac tac caa atc ttc gat ctg ttg aac cag gag ttc acc ttc acc gtc            384
His Tyr Gln Ile Phe Asp Leu Leu Asn Gln Glu Phe Thr Phe Thr Val
            115                 120                 125 gat gtc tcc cac ctc cct tgc ggt ttg aac ggt gcc ctc tac ttc gtg            432
Asp Val Ser His Leu Pro Cys Gly Leu Asn Gly Ala Leu Tyr Phe Val
130                 135                 140 acc atg gat gcc gac ggt ggc gtc tcc aag tac ccc aac aac aag gcc            480
Thr Met Asp Ala Asp Gly Gly Val Ser Lys Tyr Pro Asn Asn Lys Ala
145                 150                 155                 160 ggt gct cag tac ggt gtt gga tac tgt gac tct caa tgc cct cgt gac            528
Gly Ala Gln Tyr Gly Val Gly Tyr Cys Asp Ser Gln Cys Pro Arg Asp
                165                 170                 175 ttg aag ttc atc gct ggt cag gcc aac gtt gag ggc tgg acg ccc tcc            576
Leu Lys Phe Ile Ala Gly Gln Ala Asn Val Glu Gly Trp Thr Pro Ser
            180                 185                 190 gcc aac aac gcc aac act gga att ggc aat cac gga gct tgc tgc gcg            624
Ala Asn Asn Ala Asn Thr Gly Ile Gly Asn His Gly Ala Cys Cys Ala
            195                 200                 205 gag ctt gat atc tgg gag gca aac agc atc tca gag gcc ttg act cct            672
Glu Leu Asp Ile Trp Glu Ala Asn Ser Ile Ser Glu Ala Leu Thr Pro
        210                 215                 220 cac cct tgc gat aca ccc ggt cta tct gtt tgc act act gat gcc tgc            720
His Pro Cys Asp Thr Pro Gly Leu Ser Val Cys Thr Thr Asp Ala Cys
225                 230                 235                 240 ggt ggt acc tac agc tct gat cgt tac gcc ggt acc tgc gac cct gat            768
Gly Gly Thr Tyr Ser Ser Asp Arg Tyr Ala Gly Thr Cys Asp Pro Asp
                245                 250                 255 gga tgt gac ttc aac cct tac cgc ctt ggt gtc act gac ttc tac ggc            816
Gly Cys Asp Phe Asn Pro Tyr Arg Leu Gly Val Thr Asp Phe Tyr Gly
            260                 265                 270 tcc ggc aag acc gtt gac acc acc aag ccc ttt acc gtt gtg act caa            864
Ser Gly Lys Thr Val Asp Thr Thr Lys Pro Phe Thr Val Val Thr Gln
            275                 280                 285 ttc gtc act aac gac ggt acc tcc acc ggt tcc ctc tcc gag atc aga            912
Phe Val Thr Asn Asp Gly Thr Ser Thr Gly Ser Leu Ser Glu Ile Arg
        290                 295                 300 cgt tac tac gtt cag aac ggc gtt gtc atc ccc cag cct tcc tcc aag            960
Arg Tyr Tyr Val Gln Asn Gly Val Val Ile Pro Gln Pro Ser Ser Lys
305                 310                 315                 320
```

```
atc tcc gga atc agc gga aat gtc atc aac tcc gac tac tgc gct gct      1008
Ile Ser Gly Ile Ser Gly Asn Val Ile Asn Ser Asp Tyr Cys Ala Ala
                325                 330                 335 gaa att tcc acc ttt ggc ggg act gcc tcc ttc agc aaa cac ggt ggc      1056
Glu Ile Ser Thr Phe Gly Gly Thr Ala Ser Phe Ser Lys His Gly Gly
            340                 345                 350 ttg aca aac atg gcc gct ggt atg gaa gct ggt atg gtc ttg gtc atg      1104
Leu Thr Asn Met Ala Ala Gly Met Glu Ala Gly Met Val Leu Val Met
                355                 360                 365 agt ttg tgg gac gac tac gcc gtc aac atg ctc tgg ctc gac agc acc      1152
Ser Leu Trp Asp Asp Tyr Ala Val Asn Met Leu Trp Leu Asp Ser Thr
    370                 375                 380 tac cct aca aac gcg act ggt acc ccc ggt gcc gct cgt ggt acc tgc      1200
Tyr Pro Thr Asn Ala Thr Gly Thr Pro Gly Ala Ala Arg Gly Thr Cys
385                 390                 395                 400 gct acc act tct ggg gac ccc aag acc gtt gaa tca caa tcc ggc agc      1248
Ala Thr Thr Ser Gly Asp Pro Lys Thr Val Glu Ser Gln Ser Gly Ser
                405                 410                 415 tcc tat gtc acc ttc tct gac att cgg gtt ggt cct ttc aat tct acg      1296
Ser Tyr Val Thr Phe Ser Asp Ile Arg Val Gly Pro Phe Asn Ser Thr
            420                 425                 430 ttc agc ggt ggt tct agc acc ggt ggc agc act act act acc gcc agc      1344
Phe Ser Gly Gly Ser Ser Thr Gly Gly Ser Thr Thr Thr Thr Ala Ser
                435                 440                 445 cgc acc acc acc acc tcg gcc tct tcc acc tct act tcc agc acc tct      1392
Arg Thr Thr Thr Thr Ser Ala Ser Ser Thr Ser Thr Ser Ser Thr Ser
        450                 455                 460 act ggc act gga acc cag tct cac tac ggc cag tgc ggc ggt att ggc      1440
Thr Gly Thr Gly Thr Gln Ser His Tyr Gly Gln Cys Gly Gly Ile Gly
465                 470                 475                 480 tac agc ggc ccc acg gtc tgc gcc agc ggc aca act tgc cag gtc ctg      1488
Tyr Ser Gly Pro Thr Val Cys Ala Ser Gly Thr Thr Cys Gln Val Leu
                485                 490                 495 aac cct tac tac tct cag tgc ctg                                       1512
Asn Pro Tyr Tyr Ser Gln Cys Leu
            500

<210> SEQ ID NO 6
<211> LENGTH: 504
<212> TYPE: PRT
<213> ORGANISM: Artificial Sequence
<220> FEATURE:
<223> OTHER INFORMATION: Synthetic Construct

<400> SEQUENCE: 6

Gln Gln Ile Gly Thr Tyr Thr Ala Glu Thr His Pro Ser Leu Ser Trp
1               5                   10                  15

Ser Thr Cys Lys Ser Gly Gly Cys Thr Thr Asn Ser Gly Ala Ile
            20                  25                  30

Thr Leu Asp Ala Asn Trp Arg Trp Val His Gly Val Asn Thr Ser Thr
        35                  40                  45

Asn Cys Tyr Thr Gly Asn Thr Trp Asn Ser Ala Ile Cys Asp Thr Asp
    50                  55                  60

Ala Ser Cys Ala Gln Asp Cys Ala Leu Asp Gly Ala Asp Tyr Ser Gly
65                  70                  75                  80

Thr Tyr Gly Ile Thr Thr Ser Gly Asn Ser Leu Arg Leu Asn Phe Val
                85                  90                  95

Thr Gly Ser Asn Val Gly Ser Arg Thr Tyr Leu Met Ala Asp Asn Thr
            100                 105                 110
```

-continued

His Tyr Gln Ile Phe Asp Leu Leu Asn Gln Glu Phe Thr Phe Thr Val
            115                 120                 125

Asp Val Ser His Leu Pro Cys Gly Leu Asn Gly Ala Leu Tyr Phe Val
        130                 135                 140

Thr Met Asp Ala Asp Gly Gly Val Ser Lys Tyr Pro Asn Asn Lys Ala
145                 150                 155                 160

Gly Ala Gln Tyr Gly Val Gly Tyr Cys Asp Ser Gln Cys Pro Arg Asp
                165                 170                 175

Leu Lys Phe Ile Ala Gly Gln Ala Asn Val Glu Gly Trp Thr Pro Ser
            180                 185                 190

Ala Asn Asn Ala Asn Thr Gly Ile Gly Asn His Gly Ala Cys Cys Ala
        195                 200                 205

Glu Leu Asp Ile Trp Glu Ala Asn Ser Ile Ser Glu Ala Leu Thr Pro
210                 215                 220

His Pro Cys Asp Thr Pro Gly Leu Ser Val Cys Thr Thr Asp Ala Cys
225                 230                 235                 240

Gly Gly Thr Tyr Ser Ser Asp Arg Tyr Ala Gly Thr Cys Asp Pro Asp
                245                 250                 255

Gly Cys Asp Phe Asn Pro Tyr Arg Leu Gly Val Thr Asp Phe Tyr Gly
            260                 265                 270

Ser Gly Lys Thr Val Asp Thr Lys Pro Phe Thr Val Val Thr Gln
        275                 280                 285

Phe Val Thr Asn Asp Gly Thr Ser Thr Gly Ser Leu Ser Glu Ile Arg
290                 295                 300

Arg Tyr Tyr Val Gln Asn Gly Val Val Ile Pro Gln Pro Ser Ser Lys
305                 310                 315                 320

Ile Ser Gly Ile Ser Gly Asn Val Ile Asn Ser Asp Tyr Cys Ala Ala
                325                 330                 335

Glu Ile Ser Thr Phe Gly Gly Thr Ala Ser Phe Ser Lys His Gly Gly
            340                 345                 350

Leu Thr Asn Met Ala Ala Gly Met Glu Ala Gly Met Val Leu Val Met
        355                 360                 365

Ser Leu Trp Asp Asp Tyr Ala Val Asn Met Leu Trp Leu Asp Ser Thr
370                 375                 380

Tyr Pro Thr Asn Ala Thr Gly Thr Pro Gly Ala Ala Arg Gly Thr Cys
385                 390                 395                 400

Ala Thr Thr Ser Gly Asp Pro Lys Thr Val Glu Ser Gln Ser Gly Ser
                405                 410                 415

Ser Tyr Val Thr Phe Ser Asp Ile Arg Val Gly Pro Phe Asn Ser Thr
            420                 425                 430

Phe Ser Gly Gly Ser Ser Thr Gly Gly Ser Thr Thr Thr Ala Ser
        435                 440                 445

Arg Thr Thr Thr Thr Ser Ala Ser Ser Thr Thr Thr Ser Ser Thr Ser
450                 455                 460

Thr Gly Thr Gly Thr Gln Ser His Tyr Gly Gln Cys Gly Gly Ile Gly
465                 470                 475                 480

Tyr Ser Gly Pro Thr Val Cys Ala Ser Gly Thr Thr Cys Gln Val Leu
                485                 490                 495

Asn Pro Tyr Tyr Ser Gln Cys Leu
            500

<210> SEQ ID NO 7
<211> LENGTH: 1491
<212> TYPE: DNA

<213> ORGANISM: Artificial Sequence
<220> FEATURE:
<223> OTHER INFORMATION: Chimera of Penicillium funiculosum and
    Trichoderma reesei DNA sequences
<220> FEATURE:
<221> NAME/KEY: CDS
<222> LOCATION: (1)..(1491)

<400> SEQUENCE: 7

```
cag caa att ggt act tat acc gct gaa acc cat ccc tct ctg agc tgg      48
Gln Gln Ile Gly Thr Tyr Thr Ala Glu Thr His Pro Ser Leu Ser Trp
 1               5                  10                  15 tct act tgc aaa tcg ggt ggc agc tgc acc aca aac tcc ggt gcc att      96
Ser Thr Cys Lys Ser Gly Gly Ser Cys Thr Thr Asn Ser Gly Ala Ile
             20                  25                  30 acg tta gat gcc aac tgg cgt tgg gtc cat ggt gtc aat acc agc acc     144
Thr Leu Asp Ala Asn Trp Arg Trp Val His Gly Val Asn Thr Ser Thr
         35                  40                  45 aac tgc tac act ggc aac act tgg aat agc gcc atc tgc gac act gat     192
Asn Cys Tyr Thr Gly Asn Thr Trp Asn Ser Ala Ile Cys Asp Thr Asp
     50                  55                  60 gca tcc tgt gcc cag gac tgt gct ctc gat ggt gct gac tac tct ggc     240
Ala Ser Cys Ala Gln Asp Cys Ala Leu Asp Gly Ala Asp Tyr Ser Gly
 65                  70                  75                  80 acg tac ggt atc act acc tcc ggc aac tca ttg cgc ctg aac ttc gtt     288
Thr Tyr Gly Ile Thr Thr Ser Gly Asn Ser Leu Arg Leu Asn Phe Val
                 85                  90                  95 acc ggt tcc aac gtc gga tct cgt act tac ctg atg gcc gat aac acc     336
Thr Gly Ser Asn Val Gly Ser Arg Thr Tyr Leu Met Ala Asp Asn Thr
            100                 105                 110 cac tac caa atc ttc gat ctg ttg aac cag gag ttc acc ttc acc gtc     384
His Tyr Gln Ile Phe Asp Leu Leu Asn Gln Glu Phe Thr Phe Thr Val
        115                 120                 125 gat gtc tcc cac ctc cct tgc ggt ttg aac ggt gcc ctc tac ttc gtg     432
Asp Val Ser His Leu Pro Cys Gly Leu Asn Gly Ala Leu Tyr Phe Val
    130                 135                 140 acc atg gat gcc gac ggt ggc gtc tcc aag tac ccc aac aac aag gcc     480
Thr Met Asp Ala Asp Gly Gly Val Ser Lys Tyr Pro Asn Asn Lys Ala
145                 150                 155                 160 ggt gct cag tac ggt gtt gga tac tgt gac tct caa tgc cct cgt gac     528
Gly Ala Gln Tyr Gly Val Gly Tyr Cys Asp Ser Gln Cys Pro Arg Asp
                165                 170                 175 ttg aag ttc atc gct ggt cag gcc aac gtt gag ggc tgg acg ccc tcc     576
Leu Lys Phe Ile Ala Gly Gln Ala Asn Val Glu Gly Trp Thr Pro Ser
            180                 185                 190 gcc aac aac gcc aac act gga att ggc aat cac gga gct tgc tgc gcg     624
Ala Asn Asn Ala Asn Thr Gly Ile Gly Asn His Gly Ala Cys Cys Ala
        195                 200                 205 gag ctt gat atc tgg gag gca aac agc atc tca gag gcc ttg act cct     672
Glu Leu Asp Ile Trp Glu Ala Asn Ser Ile Ser Glu Ala Leu Thr Pro
    210                 215                 220 cac cct tgc gat aca ccc ggt cta tct gtt tgc act act gat gcc tgc     720
His Pro Cys Asp Thr Pro Gly Leu Ser Val Cys Thr Thr Asp Ala Cys
225                 230                 235                 240 ggt ggt acc tac agc tct gat cgt tac gcc ggt acc tgc gac cct gat     768
Gly Gly Thr Tyr Ser Ser Asp Arg Tyr Ala Gly Thr Cys Asp Pro Asp
                245                 250                 255 gga tgt gac ttc aac cct tac cgc ctt ggt gtc act gac ttc tac ggc     816
Gly Cys Asp Phe Asn Pro Tyr Arg Leu Gly Val Thr Asp Phe Tyr Gly
            260                 265                 270 tcc ggc aag acc gtt gac acc acc aag ccc ttt acc gtt gtg act caa     864
```

| | | | | | | | | | | | | | |
|---|---|---|---|---|---|---|---|---|---|---|---|---|---|
| Ser | Gly | Lys | Thr | Val | Asp | Thr | Thr | Lys | Pro | Phe | Thr | Val | Thr Gln |
| | | 275 | | | | 280 | | | | 285 | | | |

```
ttc gtc act aac gac ggt acc tcc acc ggt tcc ctc tcc gag atc aga      912
Phe Val Thr Asn Asp Gly Thr Ser Thr Gly Ser Leu Ser Glu Ile Arg
        290                 295                 300 cgt tac tac gtt cag aac ggc gtt gtc atc ccc cag cct tcc tcc aag      960
Arg Tyr Tyr Val Gln Asn Gly Val Val Ile Pro Gln Pro Ser Ser Lys
305                 310                 315                 320 atc tcc gga atc agc gga aat gtc atc aac tcc gac tac tgc gct gct     1008
Ile Ser Gly Ile Ser Gly Asn Val Ile Asn Ser Asp Tyr Cys Ala Ala
                325                 330                 335 gaa att tcc acc ttt ggc ggg act gcc tcc ttc agc aaa cac ggt ggc     1056
Glu Ile Ser Thr Phe Gly Gly Thr Ala Ser Phe Ser Lys His Gly Gly
                340                 345                 350 ttg aca aac atg gcc gct ggt atg gaa gct ggt atg gtc ttg gtc atg     1104
Leu Thr Asn Met Ala Ala Gly Met Glu Ala Gly Met Val Leu Val Met
                355                 360                 365 agt ttg tgg gac gac tac gcc gtc aac atg ctc tgg ctc gac agc acc     1152
Ser Leu Trp Asp Asp Tyr Ala Val Asn Met Leu Trp Leu Asp Ser Thr
370                 375                 380 tac cct aca aac gcg act ggt acc ccc ggt gcc gct cgt ggt acc tgc     1200
Tyr Pro Thr Asn Ala Thr Gly Thr Pro Gly Ala Ala Arg Gly Thr Cys
385                 390                 395                 400 gct acc act tct ggg gac ccc aag acc gtt gaa tca caa tcc ggc agc     1248
Ala Thr Thr Ser Gly Asp Pro Lys Thr Val Glu Ser Gln Ser Gly Ser
                405                 410                 415 tcc tat gtc acc ttc tct gac att cgg gtt ggt cct ttc aat tct acg     1296
Ser Tyr Val Thr Phe Ser Asp Ile Arg Val Gly Pro Phe Asn Ser Thr
                420                 425                 430 ttc agc ggc aac cct ccc ggc gga aac ccg cct ggc acc acc acc acc     1344
Phe Ser Gly Asn Pro Pro Gly Gly Asn Pro Pro Gly Thr Thr Thr Thr
                435                 440                 445 cgc cgc cca gcc act acc act gga agc tct ccc gga cct acc cag tct     1392
Arg Arg Pro Ala Thr Thr Thr Gly Ser Ser Pro Gly Pro Thr Gln Ser
450                 455                 460 cac tac ggc cag tgc ggc ggt att ggc tac agc ggc ccc acg gtc tgc     1440
His Tyr Gly Gln Cys Gly Gly Ile Gly Tyr Ser Gly Pro Thr Val Cys
465                 470                 475                 480 gcc agc ggc aca act tgc cag gtc ctg aac cct tac tac tct cag tgc     1488
Ala Ser Gly Thr Thr Cys Gln Val Leu Asn Pro Tyr Tyr Ser Gln Cys
                485                 490                 495 ctg                                                                  1491
Leu

<210> SEQ ID NO 8
<211> LENGTH: 497
<212> TYPE: PRT
<213> ORGANISM: Artificial Sequence
<220> FEATURE:
<223> OTHER INFORMATION: Synthetic Construct

<400> SEQUENCE: 8

Gln Gln Ile Gly Thr Tyr Thr Ala Glu Thr His Pro Ser Leu Ser Trp
1               5                   10                  15

Ser Thr Cys Lys Ser Gly Gly Ser Cys Thr Thr Asn Ser Gly Ala Ile
                20                  25                  30

Thr Leu Asp Ala Asn Trp Arg Trp Val His Gly Val Asn Thr Ser Thr
                35                  40                  45

Asn Cys Tyr Thr Gly Asn Thr Trp Asn Ser Ala Ile Cys Asp Thr Asp
50                  55                  60
```

```
Ala Ser Cys Ala Gln Asp Cys Ala Leu Asp Gly Ala Asp Tyr Ser Gly
65                  70                  75                  80

Thr Tyr Gly Ile Thr Thr Ser Gly Asn Ser Leu Arg Leu Asn Phe Val
                85                  90                  95

Thr Gly Ser Asn Val Gly Ser Arg Thr Tyr Leu Met Ala Asp Asn Thr
            100                 105                 110

His Tyr Gln Ile Phe Asp Leu Leu Asn Gln Glu Phe Thr Phe Thr Val
        115                 120                 125

Asp Val Ser His Leu Pro Cys Gly Leu Asn Gly Ala Leu Tyr Phe Val
    130                 135                 140

Thr Met Asp Ala Asp Gly Gly Val Ser Lys Tyr Pro Asn Asn Lys Ala
145                 150                 155                 160

Gly Ala Gln Tyr Gly Val Gly Tyr Cys Asp Ser Gln Cys Pro Arg Asp
                165                 170                 175

Leu Lys Phe Ile Ala Gly Gln Ala Asn Val Glu Gly Trp Thr Pro Ser
            180                 185                 190

Ala Asn Asn Ala Asn Thr Gly Ile Gly Asn His Gly Ala Cys Cys Ala
        195                 200                 205

Glu Leu Asp Ile Trp Glu Ala Asn Ser Ile Ser Glu Ala Leu Thr Pro
    210                 215                 220

His Pro Cys Asp Thr Pro Gly Leu Ser Val Cys Thr Thr Asp Ala Cys
225                 230                 235                 240

Gly Gly Thr Tyr Ser Ser Asp Arg Tyr Ala Gly Thr Cys Asp Pro Asp
                245                 250                 255

Gly Cys Asp Phe Asn Pro Tyr Arg Leu Gly Val Thr Asp Phe Tyr Gly
            260                 265                 270

Ser Gly Lys Thr Val Asp Thr Thr Lys Pro Phe Thr Val Val Thr Gln
        275                 280                 285

Phe Val Thr Asn Asp Gly Thr Ser Thr Gly Ser Leu Ser Glu Ile Arg
    290                 295                 300

Arg Tyr Tyr Val Gln Asn Gly Val Val Ile Pro Gln Pro Ser Ser Lys
305                 310                 315                 320

Ile Ser Gly Ile Ser Gly Asn Val Ile Asn Ser Asp Tyr Cys Ala Ala
                325                 330                 335

Glu Ile Ser Thr Phe Gly Gly Thr Ala Ser Phe Ser Lys His Gly Gly
            340                 345                 350

Leu Thr Asn Met Ala Ala Gly Met Glu Ala Gly Met Val Leu Val Met
        355                 360                 365

Ser Leu Trp Asp Asp Tyr Ala Val Asn Met Leu Trp Leu Asp Ser Thr
    370                 375                 380

Tyr Pro Thr Asn Ala Thr Gly Thr Pro Gly Ala Ala Arg Gly Thr Cys
385                 390                 395                 400

Ala Thr Thr Ser Gly Asp Pro Lys Thr Val Glu Ser Gln Ser Gly Ser
                405                 410                 415

Ser Tyr Val Thr Phe Ser Asp Ile Arg Val Gly Pro Phe Asn Ser Thr
            420                 425                 430

Phe Ser Gly Asn Pro Pro Gly Gly Asn Pro Gly Thr Thr Thr
        435                 440                 445

Arg Arg Pro Ala Thr Thr Thr Gly Ser Ser Pro Gly Pro Thr Gln Ser
    450                 455                 460

His Tyr Gly Gln Cys Gly Gly Ile Gly Tyr Ser Gly Pro Thr Val Cys
465                 470                 475                 480
```

```
Ala Ser Gly Thr Thr Cys Gln Val Leu Asn Pro Tyr Tyr Ser Gln Cys
            485                 490                 495

Leu

<210> SEQ ID NO 9
<211> LENGTH: 1512
<212> TYPE: DNA
<213> ORGANISM: Artificial Sequence
<220> FEATURE:
<223> OTHER INFORMATION: Chimera of Penicillium funiculosum and
      Trichoderma reesei DNA sequences
<220> FEATURE:
<221> NAME/KEY: CDS
<222> LOCATION: (1)..(1512)

<400> SEQUENCE: 9 cag tcg gcc tgc act ctc caa tcg gag act cac ccg cct ctg aca tgg      48
Gln Ser Ala Cys Thr Leu Gln Ser Glu Thr His Pro Pro Leu Thr Trp
1               5                   10                  15 cag aaa tgc tcg tct ggt ggc acg tgc act caa cag aca ggc tcc gtg      96
Gln Lys Cys Ser Ser Gly Gly Thr Cys Thr Gln Gln Thr Gly Ser Val
            20                  25                  30 gtc atc gac gcc aac tgg cgc tgg act cac gct acg aac agc agc acg     144
Val Ile Asp Ala Asn Trp Arg Trp Thr His Ala Thr Asn Ser Ser Thr
        35                  40                  45 aac tgc tac gat ggc aac act tgg agc tcg acc cta tgt cct gac aac     192
Asn Cys Tyr Asp Gly Asn Thr Trp Ser Ser Thr Leu Cys Pro Asp Asn
    50                  55                  60 gag acc tgc gcg aag aac tgc tgt ctg gac ggt gcc gcc tac gcg tcc     240
Glu Thr Cys Ala Lys Asn Cys Cys Leu Asp Gly Ala Ala Tyr Ala Ser
65                  70                  75                  80 acg tac gga gtt acc acg agc ggt aac agc ctc tcc att ggc ttt gtc     288
Thr Tyr Gly Val Thr Thr Ser Gly Asn Ser Leu Ser Ile Gly Phe Val
                85                  90                  95 acc cag tct gcg cag aag aac gtt ggc gct cgc ctt tac ctt atg gcg     336
Thr Gln Ser Ala Gln Lys Asn Val Gly Ala Arg Leu Tyr Leu Met Ala
            100                 105                 110 agc gac acg acc tac cag gaa ttc acc ctg ctt ggc aac gag ttc tct     384
Ser Asp Thr Thr Tyr Gln Glu Phe Thr Leu Leu Gly Asn Glu Phe Ser
        115                 120                 125 ttc gat gtt gat gtt tcg cag ctg ccg tgc ggc ttg aac gga gct ctc     432
Phe Asp Val Asp Val Ser Gln Leu Pro Cys Gly Leu Asn Gly Ala Leu
    130                 135                 140 tac ttc gtg tcc atg gac gcg gat ggt ggc gtg agc aag tat ccc acc     480
Tyr Phe Val Ser Met Asp Ala Asp Gly Gly Val Ser Lys Tyr Pro Thr
145                 150                 155                 160 aac acc gct ggc gcc aag tac ggc acg ggg tac tgt gac agc cag tgt     528
Asn Thr Ala Gly Ala Lys Tyr Gly Thr Gly Tyr Cys Asp Ser Gln Cys
                165                 170                 175 ccc cgc gat ctg aag ttc atc aat ggc cag gcc aac gtt gag ggc tgg     576
Pro Arg Asp Leu Lys Phe Ile Asn Gly Gln Ala Asn Val Glu Gly Trp
            180                 185                 190 gag ccg tca tcc aac aac gcg aac acg ggc att gga gga cac gga agc     624
Glu Pro Ser Ser Asn Asn Ala Asn Thr Gly Ile Gly Gly His Gly Ser
        195                 200                 205 tgc tgc tct gag atg gat atc tgg gag gcc aac tcc atc tcc gag gct     672
Cys Cys Ser Glu Met Asp Ile Trp Glu Ala Asn Ser Ile Ser Glu Ala
    210                 215                 220 ctt acc ccc cac cct tgc acg act gtc ggc cag gag atc tgc gag ggt     720
Leu Thr Pro His Pro Cys Thr Thr Val Gly Gln Glu Ile Cys Glu Gly
225                 230                 235                 240
```

| | |
|---|---|
| gat ggg tgc ggc gga act tac tcc gat aac aga tat ggc ggc act tgc<br>Asp Gly Cys Gly Gly Thr Tyr Ser Asp Asn Arg Tyr Gly Gly Thr Cys<br>            245                 250                 255 | 768 |
| gat ccc gat ggc tgc gac tgg aac cca tac cgc ctg ggc aac acc agc<br>Asp Pro Asp Gly Cys Asp Trp Asn Pro Tyr Arg Leu Gly Asn Thr Ser<br>        260                 265                 270 | 816 |
| ttc tac ggc cct ggc tca agc ttt acc ctc gat acc acc aag aaa ttg<br>Phe Tyr Gly Pro Gly Ser Ser Phe Thr Leu Asp Thr Thr Lys Lys Leu<br>    275                 280                 285 | 864 |
| acc gtt gtc acc cag ttc gag acg tcg ggt gcc atc aac cga tac tat<br>Thr Val Val Thr Gln Phe Glu Thr Ser Gly Ala Ile Asn Arg Tyr Tyr<br>290                 295                 300 | 912 |
| gtc cag aat ggc gtc act ttc cag cag ccc aac gcc gag ctt ggt agt<br>Val Gln Asn Gly Val Thr Phe Gln Gln Pro Asn Ala Glu Leu Gly Ser<br>305                 310                 315                 320 | 960 |
| tac tct ggc aac gag ctc aac gat gat tac tgc aca gct gag gag gca<br>Tyr Ser Gly Asn Glu Leu Asn Asp Asp Tyr Cys Thr Ala Glu Glu Ala<br>                325                 330                 335 | 1008 |
| gaa ttc ggc gga tcc tct ttc tca gac aag ggc ggc ctg act cag ttc<br>Glu Phe Gly Gly Ser Ser Phe Ser Asp Lys Gly Gly Leu Thr Gln Phe<br>            340                 345                 350 | 1056 |
| aag aag gct acc tct ggc ggc atg gtt ctg gtc atg agt ctg tgg gat<br>Lys Lys Ala Thr Ser Gly Gly Met Val Leu Val Met Ser Leu Trp Asp<br>        355                 360                 365 | 1104 |
| gat tac tac gcc aac atg ctg tgg ctg gac tcc acc tac ccg aca aac<br>Asp Tyr Tyr Ala Asn Met Leu Trp Leu Asp Ser Thr Tyr Pro Thr Asn<br>    370                 375                 380 | 1152 |
| gag acc tcc tcc aca ccc ggt gcc gtg cgc gga agc tgc tcc acc agc<br>Glu Thr Ser Ser Thr Pro Gly Ala Val Arg Gly Ser Cys Ser Thr Ser<br>385                 390                 395                 400 | 1200 |
| tcc ggt gtc cct gct cag gtc gaa tct cag tct ccc aac gcc aag gtc<br>Ser Gly Val Pro Ala Gln Val Glu Ser Gln Ser Pro Asn Ala Lys Val<br>                405                 410                 415 | 1248 |
| acc ttc tcc aac atc aag ttc gga ccc att ggc agc acc ggc aac cct<br>Thr Phe Ser Asn Ile Lys Phe Gly Pro Ile Gly Ser Thr Gly Asn Pro<br>            420                 425                 430 | 1296 |
| agc ggc ggt ggt tct agc acc ggt ggc agc act act act acc gcc agc<br>Ser Gly Gly Gly Ser Ser Thr Gly Gly Ser Thr Thr Thr Thr Ala Ser<br>        435                 440                 445 | 1344 |
| cgc acc acc acc acc tcg gcc tct tcc acc tct act tcc agc acc tct<br>Arg Thr Thr Thr Thr Ser Ala Ser Ser Thr Ser Thr Ser Ser Thr Ser<br>    450                 455                 460 | 1392 |
| act ggc act gga acc cag tct cac tac ggc cag tgc ggc ggt att ggc<br>Thr Gly Thr Gly Thr Gln Ser His Tyr Gly Gln Cys Gly Gly Ile Gly<br>465                 470                 475                 480 | 1440 |
| tac agc ggc ccc acg gtc tgc gcc agc ggc aca act tgc cag gtc ctg<br>Tyr Ser Gly Pro Thr Val Cys Ala Ser Gly Thr Thr Cys Gln Val Leu<br>                485                 490                 495 | 1488 |
| aac cct tac tac tct cag tgc ctg<br>Asn Pro Tyr Tyr Ser Gln Cys Leu<br>            500 | 1512 |

<210> SEQ ID NO 10
<211> LENGTH: 504
<212> TYPE: PRT
<213> ORGANISM: Artificial Sequence
<220> FEATURE:
<223> OTHER INFORMATION: Synthetic Construct

<400> SEQUENCE: 10

Gln Ser Ala Cys Thr Leu Gln Ser Glu Thr His Pro Pro Leu Thr Trp

```
1               5                   10                  15
Gln Lys Cys Ser Ser Gly Gly Thr Cys Thr Gln Gln Thr Gly Ser Val
                20                  25                  30

Val Ile Asp Ala Asn Trp Arg Trp Thr His Ala Thr Asn Ser Ser Thr
                35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Gly Asn Ser Leu Ser Ile Gly Phe Val
                85                  90                  95

Thr Gln Ser Ala Gln Lys Asn Val Gly Ala Arg Leu Tyr Leu Met Ala
                100                 105                 110

Ser Asp Thr Thr Tyr Gln Glu Phe Thr Leu Leu Gly Asn Glu Phe Ser
                115                 120                 125

Phe Asp Val Asp Val Ser Gln Leu Pro Cys Gly Leu Asn Gly Ala Leu
130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
                180                 185                 190

Glu Pro Ser Ser Asn Asn Ala Asn Thr Gly Ile Gly Gly His Gly Ser
                195                 200                 205

Cys Cys Ser Glu Met Asp Ile Trp Glu Ala Asn Ser Ile Ser Glu Ala
210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                245                 250                 255

Asp Pro Asp Gly Cys Asp Trp Asn Pro Tyr Arg Leu Gly Asn Thr Ser
                260                 265                 270

Phe Tyr Gly Pro Gly Ser Ser Phe Thr Leu Asp Thr Thr Lys Lys Leu
                275                 280                 285

Thr Val Val Thr Gln Phe Glu Thr Ser Gly Ala Ile Asn Arg Tyr Tyr
                290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335

Glu Phe Gly Gly Ser Ser Phe Ser Asp Lys Gly Gly Leu Thr Gln Phe
                340                 345                 350

Lys Lys Ala Thr Ser Gly Gly Met Val Leu Val Met Ser Leu Trp Asp
                355                 360                 365

Asp Tyr Tyr Ala Asn Met Leu Trp Leu Asp Ser Thr Tyr Pro Thr Asn
                370                 375                 380

Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
                405                 410                 415

Thr Phe Ser Asn Ile Lys Phe Gly Pro Ile Gly Ser Thr Gly Asn Pro
                420                 425                 430
```

```
Ser Gly Gly Gly Ser Ser Thr Gly Gly Ser Thr Thr Thr Ala Ser
            435                 440                 445

Arg Thr Thr Thr Thr Ser Ala Ser Ser Thr Ser Thr Ser Ser Thr Ser
450                 455                 460

Thr Gly Thr Gly Thr Gln Ser His Tyr Gly Gln Cys Gly Gly Ile Gly
465                 470                 475                 480

Tyr Ser Gly Pro Thr Val Cys Ala Ser Gly Thr Thr Cys Gln Val Leu
            485                 490                 495

Asn Pro Tyr Tyr Ser Gln Cys Leu
            500

<210> SEQ ID NO 11
<211> LENGTH: 1491
<212> TYPE: DNA
<213> ORGANISM: Artificial Sequence
<220> FEATURE:
<223> OTHER INFORMATION: Chimera of Penicillium funiculosum and
      Trichoderma reesei DNA sequences
<220> FEATURE:
<221> NAME/KEY: CDS
<222> LOCATION: (1)..(1491)

<400> SEQUENCE: 11 cag tcg gcc tgc act ctc caa tcg gag act cac ccg cct ctg aca tgg      48
Gln Ser Ala Cys Thr Leu Gln Ser Glu Thr His Pro Pro Leu Thr Trp
1               5                   10                  15 cag aaa tgc tcg tct ggt ggc acg tgc act caa cag aca ggc tcc gtg      96
Gln Lys Cys Ser Ser Gly Gly Thr Cys Thr Gln Gln Thr Gly Ser Val
            20                  25                  30 gtc atc gac gcc aac tgg cgc tgg act cac gct acg aac agc agc acg     144
Val Ile Asp Ala Asn Trp Arg Trp Thr His Ala Thr Asn Ser Ser Thr
        35                  40                  45 aac tgc tac gat ggc aac act tgg agc tcg acc cta tgt cct gac aac     192
Asn Cys Tyr Asp Gly Asn Thr Trp Ser Ser Thr Leu Cys Pro Asp Asn
    50                  55                  60 gag acc tgc gcg aag aac tgc tgt ctg gac ggt gcc gcc tac gcg tcc     240
Glu Thr Cys Ala Lys Asn Cys Cys Leu Asp Gly Ala Ala Tyr Ala Ser
65                  70                  75                  80 acg tac gga gtt acc acg agc ggt aac agc ctc tcc att ggc ttt gtc     288
Thr Tyr Gly Val Thr Thr Ser Gly Asn Ser Leu Ser Ile Gly Phe Val
                85                  90                  95 acc cag tct gcg cag aag aac gtt ggc gct cgc ctt tac ctt atg gcg     336
Thr Gln Ser Ala Gln Lys Asn Val Gly Ala Arg Leu Tyr Leu Met Ala
            100                 105                 110 agc gac acg acc tac cag gaa ttc acc ctg ctt ggc aac gag ttc tct     384
Ser Asp Thr Thr Tyr Gln Glu Phe Thr Leu Leu Gly Asn Glu Phe Ser
        115                 120                 125 ttc gat gtt gat gtt tcg cag ctg ccg tgc ggc ttg aac gga gct ctc     432
Phe Asp Val Asp Val Ser Gln Leu Pro Cys Gly Leu Asn Gly Ala Leu
    130                 135                 140 tac ttc gtg tcc atg gac gcg gat ggt ggc gtg agc aag tat ccc acc     480
Tyr Phe Val Ser Met Asp Ala Asp Gly Gly Val Ser Lys Tyr Pro Thr
145                 150                 155                 160 aac acc gct ggc gcc aag tac ggc acg ggg tac tgt gac agc cag tgt     528
Asn Thr Ala Gly Ala Lys Tyr Gly Thr Gly Tyr Cys Asp Ser Gln Cys
                165                 170                 175 ccc cgc gat ctg aag ttc atc aat ggc cag gcc aac gtt gag ggc tgg     576
Pro Arg Asp Leu Lys Phe Ile Asn Gly Gln Ala Asn Val Glu Gly Trp
            180                 185                 190 gag ccg tca tcc aac aac gcg aac acg ggc att gga gga cac gga agc     624
Glu Pro Ser Ser Asn Asn Ala Asn Thr Gly Ile Gly Gly His Gly Ser
```

-continued

|  |  |
|---|---|
| Glu Pro Ser Ser Asn Asn Ala Asn Thr Gly Ile Gly His Gly Ser<br>195      200      205 |  |
| tgc tgc tct gag atg gat atc tgg gag gcc aac tcc atc tcc gag gct<br>Cys Cys Ser Glu Met Asp Ile Trp Glu Ala Asn Ser Ile Ser Glu Ala<br>210      215      220 | 672 |
| ctt acc ccc cac cct tgc acg act gtc ggc cag gag atc tgc gag ggt<br>Leu Thr Pro His Pro Cys Thr Thr Val Gly Gln Glu Ile Cys Glu Gly<br>225      230      235      240 | 720 |
| gat ggg tgc ggc gga act tac tcc gat aac aga tat ggc ggc act tgc<br>Asp Gly Cys Gly Gly Thr Tyr Ser Asp Asn Arg Tyr Gly Gly Thr Cys<br>      245      250      255 | 768 |
| gat ccc gat ggc tgc gac tgg aac cca tac cgc ctg ggc aac acc agc<br>Asp Pro Asp Gly Cys Asp Trp Asn Pro Tyr Arg Leu Gly Asn Thr Ser<br>  260      265      270 | 816 |
| ttc tac ggc cct ggc tca agc ttt acc ctc gat acc acc aag aaa ttg<br>Phe Tyr Gly Pro Gly Ser Ser Phe Thr Leu Asp Thr Thr Lys Lys Leu<br>      275      280      285 | 864 |
| acc gtt gtc acc cag ttc gag acg tcg ggt gcc atc aac cga tac tat<br>Thr Val Val Thr Gln Phe Glu Thr Ser Gly Ala Ile Asn Arg Tyr Tyr<br>290      295      300 | 912 |
| gtc cag aat ggc gtc act ttc cag cag ccc aac gcc gag ctt ggt agt<br>Val Gln Asn Gly Val Thr Phe Gln Gln Pro Asn Ala Glu Leu Gly Ser<br>305      310      315      320 | 960 |
| tac tct ggc aac gag ctc aac gat gat tac tgc aca gct gag gag gca<br>Tyr Ser Gly Asn Glu Leu Asn Asp Asp Tyr Cys Thr Ala Glu Glu Ala<br>      325      330      335 | 1008 |
| gaa ttc ggc gga tcc tct ttc tca gac aag ggc ggc ctg act cag ttc<br>Glu Phe Gly Gly Ser Ser Phe Ser Asp Lys Gly Gly Leu Thr Gln Phe<br>      340      345      350 | 1056 |
| aag aag gct acc tct ggc ggc atg gtt ctg gtc atg agt ctg tgg gat<br>Lys Lys Ala Thr Ser Gly Gly Met Val Leu Val Met Ser Leu Trp Asp<br>355      360      365 | 1104 |
| gat tac tac gcc aac atg ctg tgg ctg gac tcc acc tac ccg aca aac<br>Asp Tyr Tyr Ala Asn Met Leu Trp Leu Asp Ser Thr Tyr Pro Thr Asn<br>370      375      380 | 1152 |
| gag acc tcc tcc aca ccc ggt gcc gtg cgc gga agc tgc tcc acc agc<br>Glu Thr Ser Ser Thr Pro Gly Ala Val Arg Gly Ser Cys Ser Thr Ser<br>385      390      395      400 | 1200 |
| tcc ggt gtc cct gct cag gtc gaa tct cag tct ccc aac gcc aag gtc<br>Ser Gly Val Pro Ala Gln Val Glu Ser Gln Ser Pro Asn Ala Lys Val<br>      405      410      415 | 1248 |
| acc ttc tcc aac atc aag ttc gga ccc att ggc agc acc ggc aac cct<br>Thr Phe Ser Asn Ile Lys Phe Gly Pro Ile Gly Ser Thr Gly Asn Pro<br>      420      425      430 | 1296 |
| agc ggc ggc aac cct ccc ggc gga aac ccg cct ggc acc acc acc acc<br>Ser Gly Gly Asn Pro Pro Gly Gly Asn Pro Pro Gly Thr Thr Thr Thr<br>435      440      445 | 1344 |
| cgc cgc cca gcc act acc act gga agc tct ccc gga cct gtc gct ggt<br>Arg Arg Pro Ala Thr Thr Thr Gly Ser Ser Pro Gly Pro Val Ala Gly<br>450      455      460 | 1392 |
| cac tgg ggt cag tgt ggt ggc cag ggc tgg act ggc cct acc acc tgt<br>His Trp Gly Gln Cys Gly Gly Gln Gly Trp Thr Gly Pro Thr Thr Cys<br>465      470      475      480 | 1440 |
| gtt agt gga acc aca tgc acc gtc gtg aac cct tac tac tct caa tgt<br>Val Ser Gly Thr Thr Cys Thr Val Val Asn Pro Tyr Tyr Ser Gln Cys<br>      485      490      495 | 1488 |
| ttg<br>Leu | 1491 |

<210> SEQ ID NO 12
<211> LENGTH: 497
<212> TYPE: PRT
<213> ORGANISM: Artificial Sequence
<220> FEATURE:
<223> OTHER INFORMATION: Synthetic Construct

<400> SEQUENCE: 12

```
Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Gln Thr Gly Ser Val
            20                  25                  30

Val Ile Asp Ala Asn Trp Arg Trp Thr His Ala Thr Asn Ser Ser Thr
        35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Gly Asn Ser Leu Ser Ile Gly Phe Val
                85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
    130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
    210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Thr Leu Asp Thr Thr Lys Lys Leu
        275                 280                 285

Thr Val Val Thr Gln Phe Glu Thr Ser Gly Ala Ile Asn Arg Tyr Tyr
    290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335

Glu Phe Gly Gly Ser Ser Phe Ser Asp Lys Gly Gly Leu Thr Gln Phe
            340                 345                 350

Lys Lys Ala Thr Ser Gly Gly Met Val Leu Val Met Ser Leu Trp Asp
        355                 360                 365

Asp Tyr Tyr Ala Asn Met Leu Trp Leu Asp Ser Thr Tyr Pro Thr Asn
```

```
              370               375               380
Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
                405                 410                 415

Thr Phe Ser Asn Ile Lys Phe Gly Pro Ile Gly Ser Thr Gly Asn Pro
                420                 425                 430

Ser Gly Gly Asn Pro Pro Gly Gly Asn Pro Pro Gly Thr Thr Thr Thr
            435                 440                 445

Arg Arg Pro Ala Thr Thr Thr Gly Ser Ser Pro Gly Pro Val Ala Gly
        450                 455                 460

His Trp Gly Gln Cys Gly Gly Gln Gly Trp Thr Gly Pro Thr Thr Cys
465                 470                 475                 480

Val Ser Gly Thr Thr Cys Thr Val Val Asn Pro Tyr Tyr Ser Gln Cys
                485                 490                 495

Leu

<210> SEQ ID NO 13
<211> LENGTH: 1512
<212> TYPE: DNA
<213> ORGANISM: Artificial Sequence
<220> FEATURE:
<223> OTHER INFORMATION: Chimera of Penicillium funiculosum and
      Trichoderma reesei DNA sequences
<220> FEATURE:
<221> NAME/KEY: CDS
<222> LOCATION: (1)..(1512)

<400> SEQUENCE: 13 cag tcg gcc tgc act ctc caa tcg gag act cac ccg cct ctg aca tgg       48
Gln Ser Ala Cys Thr Leu Gln Ser Glu Thr His Pro Pro Leu Thr Trp
1               5                   10                  15 cag aaa tgc tcg tct ggt ggc acg tgc act caa cag aca ggc tcc gtg       96
Gln Lys Cys Ser Ser Gly Gly Thr Cys Thr Gln Gln Thr Gly Ser Val
            20                  25                  30 gtc atc gac gcc aac tgg cgc tgg act cac gct acg aac agc agc acg      144
Val Ile Asp Ala Asn Trp Arg Trp Thr His Ala Thr Asn Ser Ser Thr
        35                  40                  45 aac tgc tac gat ggc aac act tgg agc tcg acc cta tgt cct gac aac      192
Asn Cys Tyr Asp Gly Asn Thr Trp Ser Ser Thr Leu Cys Pro Asp Asn
    50                  55                  60 gag acc tgc gcg aag aac tgc tgt ctg gac ggt gcc gcc tac gcg tcc      240
Glu Thr Cys Ala Lys Asn Cys Cys Leu Asp Gly Ala Ala Tyr Ala Ser
65                  70                  75                  80 acg tac gga gtt acc acg agc ggt aac agc ctc tcc att ggc ttt gtc      288
Thr Tyr Gly Val Thr Thr Ser Gly Asn Ser Leu Ser Ile Gly Phe Val
                85                  90                  95 acc cag tct gcg cag aag aac gtt ggc gct cgc ctt tac ctt atg gcg      336
Thr Gln Ser Ala Gln Lys Asn Val Gly Ala Arg Leu Tyr Leu Met Ala
            100                 105                 110 agc gac acg acc tac cag gaa ttc acc ctg ctt ggc aac gag ttc tct      384
Ser Asp Thr Thr Tyr Gln Glu Phe Thr Leu Leu Gly Asn Glu Phe Ser
        115                 120                 125 ttc gat gtt gat gtt tcg cag ctg ccg tgc ggc ttg aac gga gct ctc      432
Phe Asp Val Asp Val Ser Gln Leu Pro Cys Gly Leu Asn Gly Ala Leu
    130                 135                 140 tac ttc gtg tcc atg gac gcg gat ggt ggc gtg agc aag tat ccc acc      480
Tyr Phe Val Ser Met Asp Ala Asp Gly Gly Val Ser Lys Tyr Pro Thr
145                 150                 155                 160
```

```
aac acc gct ggc gcc aag tac ggc acg ggg tac tgt gac agc cag tgt      528
Asn Thr Ala Gly Ala Lys Tyr Gly Thr Gly Tyr Cys Asp Ser Gln Cys
            165                 170                 175 ccc cgc gat ctg aag ttc atc aat ggc cag gcc aac gtt gag ggc tgg      576
Pro Arg Asp Leu Lys Phe Ile Asn Gly Gln Ala Asn Val Glu Gly Trp
        180                 185                 190 gag ccg tca tcc aac aac gcg aac acg ggc att gga gga cac gga agc      624
Glu Pro Ser Ser Asn Asn Ala Asn Thr Gly Ile Gly Gly His Gly Ser
            195                 200                 205 tgc tgc tct gag atg gat atc tgg gag gcc aac tcc atc tcc gag gct      672
Cys Cys Ser Glu Met Asp Ile Trp Glu Ala Asn Ser Ile Ser Glu Ala
        210                 215                 220 ctt acc ccc cac cct tgc acg act gtc ggc cag gag atc tgc gag ggt      720
Leu Thr Pro His Pro Cys Thr Thr Val Gly Gln Glu Ile Cys Glu Gly
225                 230                 235                 240 gat ggg tgc ggc gga act tac tcc gat aac aga tat ggc ggc act tgc      768
Asp Gly Cys Gly Gly Thr Tyr Ser Asp Asn Arg Tyr Gly Gly Thr Cys
                    245                 250                 255 gat ccc gat ggc tgc gac tgg aac cca tac cgc ctg ggc aac acc agc      816
Asp Pro Asp Gly Cys Asp Trp Asn Pro Tyr Arg Leu Gly Asn Thr Ser
            260                 265                 270 ttc tac ggc cct ggc tca agc ttt acc ctc gat acc acc aag aaa ttg      864
Phe Tyr Gly Pro Gly Ser Ser Phe Thr Leu Asp Thr Thr Lys Lys Leu
        275                 280                 285 acc gtt gtc acc cag ttc gag acg tcg ggt gcc atc aac cga tac tat      912
Thr Val Val Thr Gln Phe Glu Thr Ser Gly Ala Ile Asn Arg Tyr Tyr
            290                 295                 300 gtc cag aat ggc gtc act ttc cag cag ccc aac gcc gag ctt ggt agt      960
Val Gln Asn Gly Val Thr Phe Gln Gln Pro Asn Ala Glu Leu Gly Ser
305                 310                 315                 320 tac tct ggc aac gag ctc aac gat gat tac tgc aca gct gag gag gca     1008
Tyr Ser Gly Asn Glu Leu Asn Asp Asp Tyr Cys Thr Ala Glu Glu Ala
                    325                 330                 335 gaa ttc ggc gga tcc tct ttc tca gac aag ggc ggc ctg act cag ttc     1056
Glu Phe Gly Gly Ser Ser Phe Ser Asp Lys Gly Gly Leu Thr Gln Phe
            340                 345                 350 aag aag gct acc tct ggc ggc atg gtt ctg gtc atg agt ctg tgg gat     1104
Lys Lys Ala Thr Ser Gly Gly Met Val Leu Val Met Ser Leu Trp Asp
        355                 360                 365 gat tac tac gcc aac atg ctg tgg ctg gac tcc acc tac ccg aca aac     1152
Asp Tyr Tyr Ala Asn Met Leu Trp Leu Asp Ser Thr Tyr Pro Thr Asn
            370                 375                 380 gag acc tcc tcc aca ccc ggt gcc gtg cgc gga agc tgc tcc acc agc     1200
Glu Thr Ser Ser Thr Pro Gly Ala Val Arg Gly Ser Cys Ser Thr Ser
385                 390                 395                 400 tcc ggt gtc cct gct cag gtc gaa tct cag tct ccc aac gcc aag gtc     1248
Ser Gly Val Pro Ala Gln Val Glu Ser Gln Ser Pro Asn Ala Lys Val
                    405                 410                 415 acc ttc tcc aac atc aag ttc gga ccc att ggc agc acc ggc aac cct     1296
Thr Phe Ser Asn Ile Lys Phe Gly Pro Ile Gly Ser Thr Gly Asn Pro
            420                 425                 430 agc ggt ggt tct agc acc ggt ggc agc act act act acc gcc agc         1344
Ser Gly Gly Ser Ser Thr Gly Gly Ser Thr Thr Thr Thr Ala Ser
        435                 440                 445 cgc acc acc acc acc tcg gcc tct tcc acc tct act tcc agc acc tct     1392
Arg Thr Thr Thr Thr Ser Ala Ser Ser Thr Ser Thr Ser Ser Thr Ser
450                 455                 460 act ggc act gga gtc gct ggt cac tgg ggt cag tgt ggt ggc cag ggc     1440
Thr Gly Thr Gly Val Ala Gly His Trp Gly Gln Cys Gly Gly Gln Gly
465                 470                 475                 480
```

```
tgg act ggc cct acc acc tgt gtt agt gga acc aca tgc acc gtc gtg      1488
Trp Thr Gly Pro Thr Thr Cys Val Ser Gly Thr Thr Cys Thr Val Val
                485                 490                 495 aac cct tac tac tct caa tgt ttg                                      1512
Asn Pro Tyr Tyr Ser Gln Cys Leu
            500
```

<210> SEQ ID NO 14
<211> LENGTH: 504
<212> TYPE: PRT
<213> ORGANISM: Artificial Sequence
<220> FEATURE:
<223> OTHER INFORMATION: Synthetic Construct

<400> SEQUENCE: 14

```
Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Gln Thr Gly Ser Val
            20                  25                  30

Val Ile Asp Ala Asn Trp Arg Trp Thr His Ala Thr Asn Ser Ser Thr
        35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Gly Asn Ser Leu Ser Ile Gly Phe Val
                85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
    130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
    210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Thr Leu Asp Thr Thr Lys Lys Leu
        275                 280                 285

Thr Val Val Thr Gln Phe Glu Thr Ser Gly Ala Ile Asn Arg Tyr Tyr
    290                 295                 300

Val Gln Asn Gly Val Thr Phe Gln Gln Pro Asn Ala Glu Leu Gly Ser
305                 310                 315                 320
```

```
Tyr Ser Gly Asn Glu Leu Asn Asp Asp Tyr Cys Thr Ala Glu Glu Ala
            325                 330                 335

Glu Phe Gly Gly Ser Ser Phe Ser Asp Lys Gly Gly Leu Thr Gln Phe
        340                 345                 350

Lys Lys Ala Thr Ser Gly Gly Met Val Leu Val Met Ser Leu Trp Asp
            355                 360                 365

Asp Tyr Tyr Ala Asn Met Leu Trp Leu Asp Ser Thr Tyr Pro Thr Asn
        370                 375                 380

Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
            405                 410                 415

Thr Phe Ser Asn Ile Lys Phe Gly Pro Ile Gly Ser Thr Gly Asn Pro
            420                 425                 430

Ser Gly Gly Gly Ser Ser Thr Gly Gly Ser Thr Thr Thr Ala Ser
            435                 440                 445

Arg Thr Thr Thr Thr Ser Ala Ser Ser Thr Thr Ser Ser Thr Ser
        450                 455                 460

Thr Gly Thr Gly Val Ala Gly His Trp Gly Gln Cys Gly Gly Gln Gly
465                 470                 475                 480

Trp Thr Gly Pro Thr Thr Cys Val Ser Gly Thr Thr Cys Val Val
            485                 490                 495

Asn Pro Tyr Tyr Ser Gln Cys Leu
            500

<210> SEQ ID NO 15
<211> LENGTH: 1491
<212> TYPE: DNA
<213> ORGANISM: Artificial Sequence
<220> FEATURE:
<223> OTHER INFORMATION: Chimera of Penicillium funiculosum and
      Trichoderma reesei DNA sequences
<220> FEATURE:
<221> NAME/KEY: CDS
<222> LOCATION: (1)..(1491)

<400> SEQUENCE: 15 cag caa att ggt act tat acc gct gaa acc cat ccc tct ctg agc tgg    48
Gln Gln Ile Gly Thr Tyr Thr Ala Glu Thr His Pro Ser Leu Ser Trp
1               5                   10                  15 tct act tgc aaa tcg ggt ggt agc tgc acc aca aac tcc ggt gcc att    96
Ser Thr Cys Lys Ser Gly Gly Ser Cys Thr Thr Asn Ser Gly Ala Ile
            20                  25                  30 acg tta gat gcc aac tgg cgt tgg gtc cat ggt gtc aat acc agc acc   144
Thr Leu Asp Ala Asn Trp Arg Trp Val His Gly Val Asn Thr Ser Thr
        35                  40                  45 aac tgc tac act ggc aac act tgg aat agc gcc atc tgc gac act gat   192
Asn Cys Tyr Thr Gly Asn Thr Trp Asn Ser Ala Ile Cys Asp Thr Asp
    50                  55                  60 gca tcc tgt gcc cag gac tgt gct ctc gat ggt gct gac tac tct ggc   240
Ala Ser Cys Ala Gln Asp Cys Ala Leu Asp Gly Ala Asp Tyr Ser Gly
65                  70                  75                  80 acg tac ggt atc act acc tcc ggc aac tca ttg cgc ctg aac ttc gtt   288
Thr Tyr Gly Ile Thr Thr Ser Gly Asn Ser Leu Arg Leu Asn Phe Val
                85                  90                  95 acc ggt tcc aac gtc gga tct cgt act tac ctg atg gcc gat aac acc   336
Thr Gly Ser Asn Val Gly Ser Arg Thr Tyr Leu Met Ala Asp Asn Thr
            100                 105                 110 cac tac caa atc ttc gat ctg ttg aac cag gag ttc acc ttc acc gtc   384
```

```
                His Tyr Gln Ile Phe Asp Leu Leu Asn Gln Glu Phe Thr Phe Thr Val
                            115                 120                 125 gat gtc tcc cac ctc cct tgc ggt ttg aac ggt gcc ctc tac ttc gtg        432
Asp Val Ser His Leu Pro Cys Gly Leu Asn Gly Ala Leu Tyr Phe Val
130                 135                 140 acc atg gat gcc gac ggt ggc gtc tcc aag tac ccc aac aac aag gcc        480
Thr Met Asp Ala Asp Gly Gly Val Ser Lys Tyr Pro Asn Asn Lys Ala
145                 150                 155                 160 ggt gct cag tac ggt gtt gga tac tgt gac tct caa tgc cct cgt gac        528
Gly Ala Gln Tyr Gly Val Gly Tyr Cys Asp Ser Gln Cys Pro Arg Asp
                165                 170                 175 ttg aag ttc atc gct ggt cag gcc aac gtt gag ggc tgg acg ccc tcc        576
Leu Lys Phe Ile Ala Gly Gln Ala Asn Val Glu Gly Trp Thr Pro Ser
            180                 185                 190 gcc aac aac gcc aac act gga att ggc aat cac gga gct tgc tgc gcg        624
Ala Asn Asn Ala Asn Thr Gly Ile Gly Asn His Gly Ala Cys Cys Ala
        195                 200                 205 gag ctt gat atc tgg gag gca aac agc atc tca gag gcc ttg act cct        672
Glu Leu Asp Ile Trp Glu Ala Asn Ser Ile Ser Glu Ala Leu Thr Pro
210                 215                 220 cac cct tgc gat aca ccc ggt cta tct gtt tgc act act gat gcc tgc        720
His Pro Cys Asp Thr Pro Gly Leu Ser Val Cys Thr Thr Asp Ala Cys
225                 230                 235                 240 ggt ggt acc tac agc tct gat cgt tac gcc ggt acc tgc gac cct gat        768
Gly Gly Thr Tyr Ser Ser Asp Arg Tyr Ala Gly Thr Cys Asp Pro Asp
                245                 250                 255 gga tgt gac ttc aac cct tac cgc ctt ggt gtc act gac ttc tac ggc        816
Gly Cys Asp Phe Asn Pro Tyr Arg Leu Gly Val Thr Asp Phe Tyr Gly
            260                 265                 270 tcc ggc aag acc gtt gac acc acc aag ccc ttt acc gtt gtg act caa        864
Ser Gly Lys Thr Val Asp Thr Thr Lys Pro Phe Thr Val Val Thr Gln
        275                 280                 285 ttc gtc act aac gac ggt acc tcc acc ggt tcc ctc tcc gag atc aga        912
Phe Val Thr Asn Asp Gly Thr Ser Thr Gly Ser Leu Ser Glu Ile Arg
290                 295                 300 cgt tac tac gtt cag aac ggc gtt gtc atc ccc cag cct tcc tcc aag        960
Arg Tyr Tyr Val Gln Asn Gly Val Val Ile Pro Gln Pro Ser Ser Lys
305                 310                 315                 320 atc tcc gga atc agc gga aat gtc atc aac tcc gac tac tgc gct gct       1008
Ile Ser Gly Ile Ser Gly Asn Val Ile Asn Ser Asp Tyr Cys Ala Ala
                325                 330                 335 gaa att tcc acc ttt ggc ggg act gcc tcc ttc agc aaa cac ggt ggc       1056
Glu Ile Ser Thr Phe Gly Gly Thr Ala Ser Phe Ser Lys His Gly Gly
            340                 345                 350 ttg aca aac atg gcc gct ggt atg gaa gct ggt atg gtc ttg gtc atg       1104
Leu Thr Asn Met Ala Ala Gly Met Glu Ala Gly Met Val Leu Val Met
        355                 360                 365 agt ttg tgg gac gac tac gcc gtc aac atg ctc tgg ctc gac agc acc       1152
Ser Leu Trp Asp Asp Tyr Ala Val Asn Met Leu Trp Leu Asp Ser Thr
370                 375                 380 tac cct aca aac gcg act ggt acc ccc ggt gcc gct cgt ggt acc tgc       1200
Tyr Pro Thr Asn Ala Thr Gly Thr Pro Gly Ala Ala Arg Gly Thr Cys
385                 390                 395                 400 gct acc act tct ggg gac ccc aag acc gtt gaa tca caa tcc ggc agc       1248
Ala Thr Thr Ser Gly Asp Pro Lys Thr Val Glu Ser Gln Ser Gly Ser
                405                 410                 415 tcc tat gtc acc ttc tct gac att cgg gtt ggt cct ttc aat tct acg       1296
Ser Tyr Val Thr Phe Ser Asp Ile Arg Val Gly Pro Phe Asn Ser Thr
            420                 425                 430
```

```
ttc agc ggc aac cct ccc ggc gga aac ccg cct ggc acc acc acc acc    1344
Phe Ser Gly Asn Pro Pro Gly Gly Asn Pro Pro Gly Thr Thr Thr Thr
            435                 440                 445 cgc cgc cca gcc act acc act gga agc tct ccc gga cct gtc gct ggt    1392
Arg Arg Pro Ala Thr Thr Thr Gly Ser Ser Pro Gly Pro Val Ala Gly
    450                 455                 460 cac tgg ggt cag tgt ggt ggc cag ggc tgg act ggc cct acc acc tgt    1440
His Trp Gly Gln Cys Gly Gly Gln Gly Trp Thr Gly Pro Thr Thr Cys
465                 470                 475                 480 gtt agt gga acc aca tgc acc gtc gtg aac cct tac tac tct caa tgt    1488
Val Ser Gly Thr Thr Cys Thr Val Val Asn Pro Tyr Tyr Ser Gln Cys
                485                 490                 495 ttg                                                                1491
Leu

<210> SEQ ID NO 16
<211> LENGTH: 497
<212> TYPE: PRT
<213> ORGANISM: Artificial Sequence
<220> FEATURE:
<223> OTHER INFORMATION: Synthetic Construct

<400> SEQUENCE: 16

Gln Gln Ile Gly Thr Tyr Thr Ala Glu Thr His Pro Ser Leu Ser Trp
1               5                   10                  15

Ser Thr Cys Lys Ser Gly Gly Ser Cys Thr Thr Asn Ser Gly Ala Ile
            20                  25                  30

Thr Leu Asp Ala Asn Trp Arg Trp Val His Gly Val Asn Thr Ser Thr
        35                  40                  45

Asn Cys Tyr Thr Gly Asn Thr Trp Asn Ser Ala Ile Cys Asp Thr Asp
    50                  55                  60

Ala Ser Cys Ala Gln Asp Cys Ala Leu Asp Gly Ala Asp Tyr Ser Gly
65                  70                  75                  80

Thr Tyr Gly Ile Thr Thr Ser Gly Asn Ser Leu Arg Leu Asn Phe Val
                85                  90                  95

Thr Gly Ser Asn Val Gly Ser Arg Thr Tyr Leu Met Ala Asp Asn Thr
            100                 105                 110

His Tyr Gln Ile Phe Asp Leu Leu Asn Gln Glu Phe Thr Phe Thr Val
        115                 120                 125

Asp Val Ser His Leu Pro Cys Gly Leu Asn Gly Ala Leu Tyr Phe Val
    130                 135                 140

Thr Met Asp Ala Asp Gly Gly Val Ser Lys Tyr Pro Asn Asn Lys Ala
145                 150                 155                 160

Gly Ala Gln Tyr Gly Val Gly Tyr Cys Asp Ser Gln Cys Pro Arg Asp
                165                 170                 175

Leu Lys Phe Ile Ala Gly Gln Ala Asn Val Glu Gly Trp Thr Pro Ser
            180                 185                 190

Ala Asn Asn Ala Asn Thr Gly Ile Gly Asn His Gly Ala Cys Cys Ala
        195                 200                 205

Glu Leu Asp Ile Trp Glu Ala Asn Ser Ile Ser Glu Ala Leu Thr Pro
    210                 215                 220

His Pro Cys Asp Thr Pro Gly Leu Ser Val Cys Thr Thr Asp Ala Cys
225                 230                 235                 240

Gly Gly Thr Tyr Ser Ser Asp Arg Tyr Ala Gly Thr Cys Asp Pro Asp
                245                 250                 255

Gly Cys Asp Phe Asn Pro Tyr Arg Leu Gly Val Thr Asp Phe Tyr Gly
            260                 265                 270
```

Ser Gly Lys Thr Val Asp Thr Lys Pro Phe Thr Val Thr Gln
    275                 280                 285

Phe Val Thr Asn Asp Gly Thr Ser Thr Gly Ser Leu Ser Glu Ile Arg
    290                 295                 300

Arg Tyr Tyr Val Gln Asn Gly Val Val Ile Pro Gln Pro Ser Ser Lys
305                 310                 315                 320

Ile Ser Gly Ile Ser Gly Asn Val Ile Asn Ser Asp Tyr Cys Ala Ala
                325                 330                 335

Glu Ile Ser Thr Phe Gly Gly Thr Ala Ser Phe Ser Lys His Gly Gly
                340                 345                 350

Leu Thr Asn Met Ala Ala Gly Met Glu Ala Gly Met Val Leu Val Met
                355                 360                 365

Ser Leu Trp Asp Asp Tyr Ala Val Asn Met Leu Trp Leu Asp Ser Thr
    370                 375                 380

Tyr Pro Thr Asn Ala Thr Gly Thr Pro Gly Ala Ala Arg Gly Thr Cys
385                 390                 395                 400

Ala Thr Thr Ser Gly Asp Pro Lys Thr Val Glu Ser Gln Ser Gly Ser
                405                 410                 415

Ser Tyr Val Thr Phe Ser Asp Ile Arg Val Gly Pro Phe Asn Ser Thr
                420                 425                 430

Phe Ser Gly Asn Pro Pro Gly Gly Asn Pro Gly Thr Thr Thr Thr
    435                 440                 445

Arg Arg Pro Ala Thr Thr Thr Gly Ser Ser Pro Gly Pro Val Ala Gly
    450                 455                 460

His Trp Gly Gln Cys Gly Gly Gln Gly Trp Thr Gly Pro Thr Thr Cys
465                 470                 475                 480

Val Ser Gly Thr Thr Cys Thr Val Val Asn Pro Tyr Tyr Ser Gln Cys
                485                 490                 495

Leu

```
<210> SEQ ID NO 17
<211> LENGTH: 28
<212> TYPE: DNA
<213> ORGANISM: Artificial Sequence
<220> FEATURE:
<223> OTHER INFORMATION: PCR Primer

<400> SEQUENCE: 17
tgctcttttg agctacaaga acctgtgg                                          28

<210> SEQ ID NO 18
<211> LENGTH: 30
<212> TYPE: DNA
<213> ORGANISM: Artificial Sequence
<220> FEATURE:
<223> OTHER INFORMATION: PCR Primer

<400> SEQUENCE: 18
gaacaagctt tttggcatcg tggatccatt                                        30

<210> SEQ ID NO 19
<211> LENGTH: 35
<212> TYPE: DNA
<213> ORGANISM: Artificial Sequence
<220> FEATURE:
<223> OTHER INFORMATION: PCR Primer

<400> SEQUENCE: 19
```

```
acttactagt atgcctcaat cctgggaaga actgg                                35

<210> SEQ ID NO 20
<211> LENGTH: 34
<212> TYPE: DNA
<213> ORGANISM: Artificial Sequence
<220> FEATURE:
<223> OTHER INFORMATION: PCR Primer

<400> SEQUENCE: 20
attgactagt ctatggagtc accacatttc ccag                                 34

<210> SEQ ID NO 21
<211> LENGTH: 26
<212> TYPE: DNA
<213> ORGANISM: Artificial Sequence
<220> FEATURE:
<223> OTHER INFORMATION: PCR Primer

<400> SEQUENCE: 21
ctggaaagtg acgccattct ggacat                                          26

<210> SEQ ID NO 22
<211> LENGTH: 26
<212> TYPE: DNA
<213> ORGANISM: Artificial Sequence
<220> FEATURE:
<223> OTHER INFORMATION: PCR Primer

<400> SEQUENCE: 22
atgaagaagc cggagttgac tgcaac                                          26

<210> SEQ ID NO 23
<211> LENGTH: 22
<212> TYPE: DNA
<213> ORGANISM: Artificial Sequence
<220> FEATURE:
<223> OTHER INFORMATION: PCR Primer

<400> SEQUENCE: 23
ctcccagctg actggccaat tc                                              22

<210> SEQ ID NO 24
<211> LENGTH: 28
<212> TYPE: DNA
<213> ORGANISM: Artificial Sequence
<220> FEATURE:
<223> OTHER INFORMATION: PCR Primer

<400> SEQUENCE: 24
cggcttcttc atactagtgg caggaaat                                        28

<210> SEQ ID NO 25
<211> LENGTH: 24
<212> TYPE: DNA
<213> ORGANISM: Artificial Sequence
<220> FEATURE:
<223> OTHER INFORMATION: PCR Primer

<400> SEQUENCE: 25
agcactctct cgcccaatga tgtc                                            24

<210> SEQ ID NO 26
<211> LENGTH: 29
<212> TYPE: DNA
<213> ORGANISM: Artificial Sequence
```

```
<220> FEATURE:
<223> OTHER INFORMATION: PCR Primer

<400> SEQUENCE: 26
tccgactctt ttaatcatcg cgtatatcc                                              29

<210> SEQ ID NO 27
<211> LENGTH: 25
<212> TYPE: DNA
<213> ORGANISM: Artificial Sequence
<220> FEATURE:
<223> OTHER INFORMATION: PCR Primer

<400> SEQUENCE: 27
aagagtatga tccggaggcg tacca                                                  25

<210> SEQ ID NO 28
<211> LENGTH: 32
<212> TYPE: DNA
<213> ORGANISM: Artificial Sequence
<220> FEATURE:
<223> OTHER INFORMATION: PCR Primer

<400> SEQUENCE: 28
ccaataatac attaacaaca cagtttcagc cc                                          32
```

ENHANCED PROCESSIVE CELLULASES

CROSS-REFERENCE TO RELATED APPLICATIONS

This application is a divisional filing of U.S. application Ser. No. 14/365,200, filed Jun. 13, 2014, which is a national stage entry of International Application No. PCT/US12/70165, filed Dec. 17, 2012, which claims priority to U.S. Provisional Application No. 61/576,585, filed Dec. 16, 2011. The contents of each listed application are incorporated by reference in their entirety.

CONTRACTUAL ORIGIN

The United States Government has rights in this invention under Contract No. DE-AC36-08GO28308 between the United States Department of Energy and Alliance for Sustainable Energy, LLC, the Manager and Operator of the National Renewable Energy Laboratory.

REFERENCE TO SEQUENCE LISTING

This application contains a Sequence Listing submitted as an electronic text file entitled "11-07_Seq_ST25.txt," having a size in bytes of 96 kb and created on Dec. 14, 2012. Pursuant to 37 CFR § 1.52(e)(5), the information contained in the above electronic file is hereby incorporated by reference in its entirety.

BACKGROUND

The production of sustainable transportation fuels and commodity chemicals from lignocellulosic biomass is a major component of the international renewable energy technology portfolio, which will ultimately provide significant energy, economic, and climate security for the world. However, plant cell walls are highly evolved heterogeneous composite structures, which represent a significant challenge to deconstruct selectively. The majority of the sugars locked in plant cell walls are from cellulose and hemicellulose, with the former being more recalcitrant to deconstruction.

To date, many processes have been developed to produce fuels from biomass-derived sugars, ranging from ethanol via fermentation to higher alcohols from genetically-modified organisms to hydrocarbons produced biologically or catalytically. Thus, over a wide range of fuel production options, there is significant impetus to develop cost-effective methods to produce sugars for upgrading to fuels and commodity chemicals. The current leading industrial option to produce sugars from lignocellulosic biomass utilizes a thermochemical pretreatment step that renders the plant cell wall more amenable to the effective application of enzyme cocktails that deconstruct cellulose and hemicellulose to soluble sugars. The enzymatic hydrolysis step alone represents a significant fraction of the operating and capital cost of lignocellulosic biofuel production.

Most enzyme cocktails under development today are based on fungal or bacterial cellulase secretomes. The industrial emphasis on fungal cocktails originated from the United States Army's isolation of the fungus *Trichoderma reesei* (anamorph of *Hypocrea jecorina*) in the South Pacific in the late 1940s, which has grown into an important platform for the production of cellulases at extremely high protein titers. The use of bacterial cellulase cocktails has focused effort on both free cellulase systems and complexed enzyme (i.e., cellulosomal) systems, as well as engineering of cellulase-producing bacteria and fungi to produce fuels and chemicals directly in a process known as Consolidated Bioprocessing. In the fungal enzyme cocktails, the processive cellulases are the primary components, and provide the majority of the hydrolytic activity for cellulose conversion to glucose. The processive cellulases have thus been the focus of many structural and biochemical studies and the primary targets for cellulase engineering.

The foregoing examples of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods that are meant to be exemplary and illustrative, not limiting in scope. In various embodiments, one or more of the above-described problems have been reduced or eliminated, while other embodiments are directed to other improvements.

Exemplary embodiments provide isolated nucleic acid molecules that encode chimeric Cel7A polypeptides that have cellulase activities at least 1.5-fold greater than wild-type Cel7A polypeptides. In certain embodiments, the chimeric Cel7A polypeptides comprise domains from *Penicillium funiculosum* and *Trichoderma reesei* Cel7A polypeptides, such as the catalytic domain (CD) from the *Penicillium funiculosum* Cel7A polypeptide and the carbohydrate-binding module (CBM) and linker domain from the *Trichoderma reesei* Cel7A polypeptide.

Additional embodiments provide chimeric Cel7A polypeptides that have cellulase activities at least 1.5-fold greater than wild-type Cel7A polypeptides and methods for degrading cellulose or lignocellulosic biomass by contacting a cellulose containing material with the isolated chimeric Cel7A polypeptides.

In addition to the exemplary aspects and embodiments described above, further aspects and embodiments will become apparent by reference to the drawings and by study of the following descriptions.

BRIEF DESCRIPTION OF THE DRAWINGS

Exemplary embodiments are illustrated in referenced figures of the drawings. It is intended that the embodiments and figures disclosed herein are to be considered illustrative rather than limiting.

FIG. 2 shows the nucleic acid (SEQ ID NO:1) and amino acid (SEQ ID NO:2) sequences for wild-type Cel7A from *Penicillium funiculosum*. The linker domain is underlined and the CBM is in bold.

FIG. 3 shows the nucleic acid (SEQ ID NO:3) and amino acid (SEQ ID NO:4) sequences for wild-type Cel7A from *Trichoderma reesei*. The linker domain is underlined and the CBM is in bold.

FIG. 4 shows the nucleic acid (SEQ ID NO:5) and amino acid (SEQ ID NO:6) sequences for a chimeric Cel7A containing the CBM from *Trichoderma reesei* and the linker domain and catalytic domain from *Penicillium funiculosum*. The linker domain is underlined and the CBM is in bold.

FIG. 5 shows the nucleic acid (SEQ ID NO:7) and amino acid (SEQ ID NO:8) sequences for a chimeric Cel7A containing the CBM and linker domain from *Trichoderma reesei* and the catalytic domain from *Penicillium funiculosum*. The linker domain is underlined and the CBM is in bold.

FIG. 6 shows the nucleic acid (SEQ ID NO:9) and amino acid (SEQ ID NO:10) sequences for a chimeric Cel7A containing the CBM and catalytic domain from *Trichoderma reesei* and the linker domain from *Penicillium funiculosum*. The linker domain is underlined and the CBM is in bold.

FIG. 7 shows the nucleic acid (SEQ ID NO:11) and amino acid (SEQ ID NO:12) sequences for a chimeric Cel7A containing the CBM from *Penicillium funiculosum* and the catalytic domain and linker domain from *Trichoderma reesei*. The linker domain is underlined and the CBM is in bold.

FIG. 8 shows the nucleic acid (SEQ ID NO:13) and amino acid (SEQ ID NO:14) sequences for a chimeric Cel7A containing the CBM and linker domain from *Penicillium funiculosum* and the catalytic domain from *Trichoderma reesei*. The linker domain is underlined and the CBM is in bold.

FIG. 9 shows the nucleic acid (SEQ ID NO:15) and amino acid (SEQ ID NO:16) sequences for a chimeric Cel7A containing the CBM and catalytic domain from *Penicillium funiculosum* and the linker domain from *Trichoderma reesei*. The linker domain is underlined and the CBM is in bold.

DETAILED DESCRIPTION

Nucleic acid molecules encoding chimeric Cel7A polypeptides that function as improved cellulases are disclosed herein. These nucleic acids may be expressed in hosts such as fungi, which in turn may be cultured to produce cellulases. Also disclosed are methods of using chimeric Cel7A polypeptides for the conversion of cellulose to sugars such as glucose.

Despite efforts to engineer processive cellulases with significantly improved activities, few successes have been demonstrated. The results of past efforts have been summarized, for example, in a review article by Wilson (*Curr. Opin. Biotechnol.* 20:295-299 (2009) (noting that "[a]t this time there are no published reports of engineered cellulases with major (greater than 1.5-fold) increases in activity on crystalline cellulose."). Prior cellulase engineering has focused upon screening small sets of rationally guided mutations for higher thermal stability and subsequent modest gains in activity at higher conversion temperatures. Significant activity improvement in processive cellulase enzymes on realistic substrates at industrially relevant enzyme loadings and substrate conversion levels remains to be demonstrated.

Disclosed herein are methods for dramatically improving the activity of processive cellulases (e.g., the Glycoside Hydrolase Family 7 cellobiohydrolase (Cel7A)) by exchanging domains from Family 7 cellulases. The resulting chimeric Cel7A polypeptides surprisingly exhibit up to, or in excess of, 3-fold cellulase activity improvement when compared with the wild-type Cel7A polypeptides from which they were derived.

Figure 1:
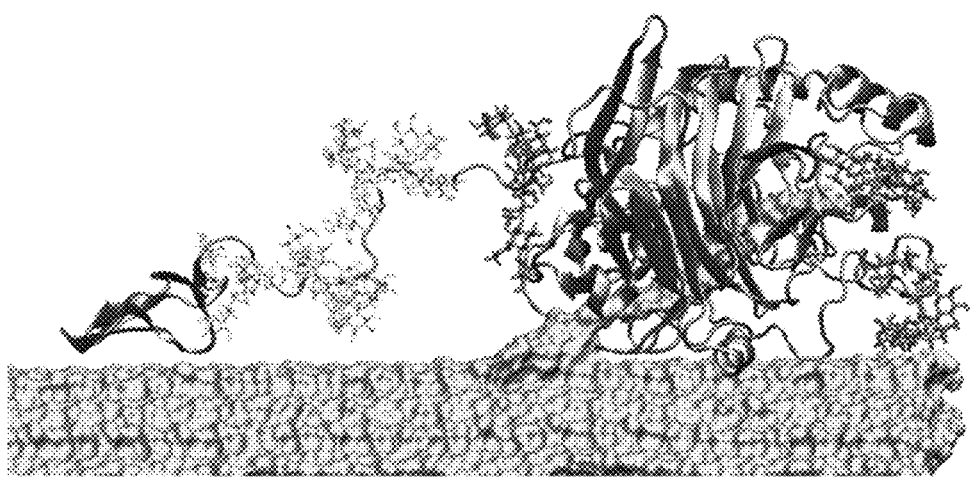
FIG. 1 illustrates the Family 7 cellobiohydrolase (Cel7A) from *T. reesei* in the catalytically-active complex on a cellulose microfibril.

Family 7 cellobiohydrolases are expressed by fungi and are typically comprised of three sub-domains: a small Family 1 carbohydrate-binding module (CBM) connected to a large catalytic domain (CD) by a flexible linker peptide. FIG. 1 shows the catalytically-active complex of Cel7A from *T. reesei*. One or more processive Glycoside Hydrolase Family 7 cellobiohydrolases (e.g., Cel7A) typically comprise up to 70% by mass of fungal enzyme cocktails used to convert cellulosic materials to component sugars for subsequent fermentation to, for example, biofuels such as ethanol.

Rational engineering of cellobiohydrolases requires insight into the structure and function of the individual sub-domains, as well as the entire enzyme complexed with cellulose. Such insights are becoming possible with the advent of advanced experimental and computational techniques. Hypotheses as to the role of the individual sub-domains have remained relatively unchanged since the first structural studies of multi-domain cellulases.

The CBM is thought to be primarily responsible for increasing the binding affinity of a given cellulase CD to a cellulose substrate, thus ensuring a high catalyst concentration at the solid surface. The linker peptide/domain is thought to act as a flexible tether between the CBM and CD, but has no verified function beyond connecting these two domains. It is still unknown if the linker interacts with cellulose or aids in CBM binding. The CD in processive Family 7 cellulases exhibits a long tunnel for threading a single polymer chain of cellulose for complexation and hydrolysis to the disaccharide cellobiose. The putative catalytic cycle of Cel7A includes surface binding, locating a free cellulose chain end, chain complexation, hydrolysis, product expulsion, and processivity until the cellulase consumes an entire chain or becomes stuck due to obstacles in its path.

As used herein, the terms "chimeric polypeptide" or "chimera" refer to a polypeptide composed of parts of different wild-type polypeptides and typically composed of discrete functional domains from different polypeptides. For example, a chimeric Cel7A polypeptide may comprise a CD, linker domain, or CBM from two or more distinct Cel7A polypeptides. For exemplary purposes, the present disclosure is directed to chimeric polypeptides comprising domains from the Cel7A polypeptides of *Penicillium funicu-*

*losum* and *Trichoderma reesei*. However, the concepts disclosed herein encompass chimeras of Cel7A polypeptides from other filamentous fungi that exhibit enhanced enzymatic activities. The amino acid sequences for the wild-type *Penicillium funiculosum* (SEQ ID NO:2) and *Trichoderma reesei* (SEQ ID NO:4) Cel7A polypeptides and the CD, linker and CBM of each are illustrated in FIGS. 2 and 3, respectively.

Examples of chimeric Cel7A polypeptides include those set forth in Table 1 below, wherein T represents the indicated Cel7A polypeptide domain from *T. reesei* and P represents the indicated Cel7A polypeptide domain from *P. funiculosum*.

TABLE 1

| CBM | Linker | CD | FIG. | Nucleic Acid | Amino Acid |
|---|---|---|---|---|---|
| T | P | P | 4 | SEQ ID NO: 5 | SEQ ID NO: 6 |
| T | T | P | 5 | SEQ ID NO: 7 | SEQ ID NO: 8 |
| T | P | T | 6 | SEQ ID NO: 9 | SEQ ID NO: 10 |
| P | T | T | 7 | SEQ ID NO: 11 | SEQ ID NO: 12 |
| P | P | T | 8 | SEQ ID NO: 13 | SEQ ID NO: 14 |
| P | T | P | 9 | SEQ ID NO: 15 | SEQ ID NO: 16 |

Chimeras may also include CBMs, linker domains, and CDs from other Cel7A polypeptides, including Cel7A polypeptides from *Humicola insolens, Aspergillus niger, Chrysosporium lucknowense, Fusarium oxysporum, Hypocrea koningii, Melanocarpus albomyces, Neurospora crassa, Phanerochaete chrysosporium*, and *Thielavia terristris*.

The chimeric Cel7A polypeptides exhibit surprisingly improved cellulase activities when compared to the wild-type Cel7A polypeptides from which they were derived. In some embodiments, the reference wild-type Cel7A polypeptide may be the source of the CD, the source of the linker domain, or the source of the CBM. For example, activity of the TTP chimera (CBM-linker-CD) may be relative to the activity of the wild-type Cel7A polypeptide from *Trichoderma reesei* or *Penicillium funiculosum*.

The term "improved cellulase activity" refers to an increased rate of hydrolysis of a cellulosic substrate. Relative activities for chimeric and wild-type Cel7A polypeptides can be determined using conventional assays, including those discussed in the Examples below. Additional assays suitable for determining cellulase activity include hydrolysis assays on industrially relevant cellulose-containing substrates such as pretreated corn stover. Hydrolysis assays on crystalline cellulose or amorphous cellulose or on small molecule fluorescent reporters may also be used to determine cellulase activity. In certain embodiments, cellulase activity is expressed as the amount of time or enzyme concentration needed to reach a certain percentage (e.g., 80%) of cellulose conversion to sugars.

In contrast to the results of previous attempts to engineer processive cellulases, the chimeric Cel7A polypeptides herein exhibit cellulase activities that are at least 1.5-fold greater than the wild-type Cel7A polypeptide and that can reach at least 3-fold greater activity. In certain embodiments, the chimeric Cel7A polypeptides exhibit cellulase activities that are at least 1.1-, 1.2-, 1.3-, 1.4-, 1.5-, 1.6-, 1.7-, 1.8-, 1.9-, 2-, 2.1-, 2.2-, 2.3-, 2.4-, 2.5-, 2.6-, 2.7-, 2.8-, 2.9-, 3-, 3.1-, 3.2-, 3.3-, 3.4-, 3.5, 3.6-, 3.7-, 3.8-, 3.9-, 4-, 4.1-, 4.2-, 4.3-, 4.4-, 4.5, 4.6-, 4.7-, 4.8-, 4.9-, or 5-fold greater than the wild-type Cel7A polypeptide.

"Nucleic acid" or "polynucleotide" as used herein refers to purine- and pyrimidine-containing polymers of any length, either polyribonucleotides or polydeoxyribonucleotide or mixed polyribo-polydeoxyribonucleotides. This includes single- and double-stranded molecules (i.e., DNA-DNA, DNA-RNA and RNA-RNA hybrids) as well as "protein nucleic acids" (PNA) formed by conjugating bases to an amino acid backbone. This also includes nucleic acids containing modified bases.

Nucleic acids referred to herein as "isolated" are nucleic acids that have been removed from their natural milieu or separated away from the nucleic acids of the genomic DNA or cellular RNA of their source of origin (e.g., as it exists in cells or in a mixture of nucleic acids such as a library), and may have undergone further processing. Isolated nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids that are isolated.

Nucleic acids referred to herein as "recombinant" are nucleic acids which have been produced by recombinant DNA methodology, including those nucleic acids that are generated by procedures that rely upon a method of artificial replication, such as the polymerase chain reaction (PCR) and/or cloning into a vector using restriction enzymes. Recombinant nucleic acids also include those that result from recombination events that occur through the natural mechanisms of cells, but are selected for after the introduction to the cells of nucleic acids designed to allow or make probable a desired recombination event. Portions of isolated nucleic acids that code for polypeptides having a certain function can be identified and isolated by, for example, the method disclosed in U.S. Pat. No. 4,952,501.

An isolated nucleic acid molecule can be isolated from its natural source or produced using recombinant DNA technology (e.g., polymerase chain reaction (PCR) amplification, cloning) or chemical synthesis. Isolated nucleic acid molecules can include, for example, genes, natural allelic variants of genes, coding regions or portions thereof, and coding and/or regulatory regions modified by nucleotide insertions, deletions, substitutions, and/or inversions in a manner such that the modifications do not substantially interfere with the nucleic acid molecule's ability to encode a polypeptide or to form stable hybrids under stringent conditions with natural gene isolates. An isolated nucleic acid molecule can include degeneracies. As used herein, nucleotide degeneracy refers to the phenomenon that one amino acid can be encoded by different nucleotide codons. Thus, the nucleic acid sequence of a nucleic acid molecule that encodes a protein or polypeptide can vary due to degeneracies.

Unless so specified, a nucleic acid molecule is not required to encode a protein having protein activity. A nucleic acid molecule can encode a truncated, mutated or inactive protein, for example. In addition, nucleic acid molecules may also be useful as probes and primers for the identification, isolation and/or purification of other nucleic acid molecules, independent of a protein-encoding function.

Suitable nucleic acids include fragments or variants (e.g., of SEQ ID NO: 5, 7, 9, 11, 13 or 15) that encode a functional cellulase. For example, a fragment can comprise the minimum nucleotides required to encode a functional cellulase. Nucleic acid variants include nucleic acids with one or more nucleotide additions, deletions, substitutions, including transitions and transversions, insertion, or modifications (e.g., via RNA or DNA analogs). Alterations may occur at the 5' or 3' terminal positions of the reference nucleotide sequence or anywhere between those terminal positions, interspersed either individually among the nucleotides in the reference sequence or in one or more contiguous groups within the reference sequence.

In certain embodiments, a nucleic acid may be identical to the sequence represented as SEQ ID NO: 5, 7, 9, 11, 13 or 15. In other embodiments, the nucleic acids may be least about 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 5, 7, 9, 11, 13 or 15, or 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 5, 7, 9, 11, 13 or 15. Sequence identity calculations can be performed using computer programs, hybridization methods, or calculations. Exemplary computer program methods to determine identity and similarity between two sequences include, but are not limited to, the GCG program package, BLASTN, BLASTX, TBLASTX, and FASTA. The BLAST programs are publicly available from NCBI and other sources. For example, nucleotide sequence identity can be determined by comparing query sequences to sequences in publicly available sequence databases (NCBI) using the BLASTN2 algorithm.

Embodiments of the nucleic acids include those that encode a chimeric Cel7A polypeptide that functions as a cellulase or functional equivalents thereof. The amino acid sequences of exemplary chimeric Cel7A polypeptides are depicted in FIGS. 4-9 and represented by SEQ ID NOS:6, 8, 10, 12, 14 and 16. A functional equivalent includes fragments or variants of these that exhibit the ability to function as a cellulase. As a result of the degeneracy of the genetic code, many nucleic acid sequences can encode a polypeptide having, for example, the amino acid sequence of SEQ ID NO:6, 8, 10, 12, 14 or 16. Such functionally equivalent variants are contemplated herein.

Altered or variant nucleic acids can be produced by one of skill in the art using the sequence data illustrated herein and standard techniques known in the art. Variant nucleic acids may be detected and isolated by hybridization under high stringency conditions or moderate stringency conditions, for example, which are chosen to prevent hybridization of nucleic acids having non-complementary sequences. "Stringency conditions" for hybridizations is a term of art that refers to the conditions of temperature and buffer concentration that permit hybridization of a particular nucleic acid to another nucleic acid in which the first nucleic acid may be perfectly complementary to the second, or the first and second may share some degree of complementarity that is less than perfect.

Nucleic acids may be derived from a variety of sources including DNA, cDNA, synthetic DNA, synthetic RNA, or combinations thereof. Such sequences may comprise genomic DNA, which may or may not include naturally occurring introns. Moreover, such genomic DNA may be obtained in association with promoter regions or poly (A) sequences. The sequences, genomic DNA, or cDNA may be obtained in any of several ways. Genomic DNA can be extracted and purified from suitable cells by means well known in the art. Alternatively, mRNA can be isolated from a cell and used to produce cDNA by reverse transcription or other means.

Oligonucleotides that are fragments of SEQ ID NO: 5, 7, 9, 11, 13 or 15 and antisense nucleic acids that are complementary, in whole or in part, to SEQ ID NO: 5, 7, 9, 11, 13 or 15 are contemplated herein. Oligonucleotides may be used as primers or probes or for any other use known in the art. Antisense nucleic acids may be used, for example, to inhibit gene expression when introduced into a cell or for any other use known in the art. Oligonucleotides and antisense nucleic acids can be produced by standard techniques known in the art.

Also disclosed herein are recombinant vectors, including expression vectors, containing nucleic acids encoding chimeric Cel7A polypeptides. A "recombinant vector" is a nucleic acid molecule that is used as a tool for manipulating a nucleic acid sequence of choice or for introducing such a nucleic acid sequence into a host cell. A recombinant vector may be suitable for use in cloning, sequencing, or otherwise manipulating the nucleic acid sequence of choice, such as by expressing or delivering the nucleic acid sequence of choice into a host cell to form a recombinant cell. Such a vector typically contains heterologous nucleic acid sequences not naturally found adjacent to a nucleic acid sequence of choice, although the vector can also contain regulatory nucleic acid sequences (e.g., promoters, untranslated regions) that are naturally found adjacent to the nucleic acid sequences of choice or that are useful for expression of the nucleic acid molecules.

A recombinant vector can be either RNA or DNA, either prokaryotic or eukaryotic, and typically is a plasmid. The vector can be maintained as an extrachromosomal element (e.g., a plasmid) or it can be integrated into the chromosome of a recombinant host cell. The entire vector can remain in place within a host cell, or under certain conditions, the plasmid DNA can be deleted, leaving behind the nucleic acid molecule of choice. An integrated nucleic acid molecule can be under chromosomal promoter control, under native or plasmid promoter control, or under a combination of several promoter controls. Single or multiple copies of the nucleic acid molecule can be integrated into the chromosome. A recombinant vector can contain at least one selectable marker.

The term "expression vector" refers to a recombinant vector that is capable of directing the expression of a nucleic acid sequence that has been cloned into it after insertion into a host cell or other (e.g., cell-free) expression system. A nucleic acid sequence is "expressed" when it is transcribed to yield an mRNA sequence. In most cases, this transcript will be translated to yield an amino acid sequence. The cloned gene is usually placed under the control of (i.e., operably linked to) an expression control sequence. The phrase "operatively linked" refers to linking a nucleic acid molecule to an expression control sequence in a manner such that the molecule can be expressed when introduced (i.e., transformed, transduced, transfected, conjugated or conduced) into a host cell.

Recombinant vectors and expression vectors may contain one or more regulatory sequences or expression control sequences. Regulatory sequences broadly encompass expression control sequences (e.g., transcription control sequences or translation control sequences), as well as sequences that allow for vector replication in a host cell. Transcription control sequences are sequences that control the initiation, elongation, or termination of transcription. Suitable regulatory sequences include any sequence that can function in a host cell or organism into which the recombinant nucleic acid molecule is to be introduced, including those that control transcription initiation, such as promoter, enhancer, terminator, operator and repressor sequences. Additional regulatory sequences include translation regulatory sequences, origins of replication, and other regulatory sequences that are compatible with the recombinant cell. The expression vectors may contain elements that allow for constitutive expression or inducible expression of the protein or proteins of interest. Numerous inducible and constitutive expression systems are known in the art.

Typically, an expression vector includes at least one nucleic acid molecule encoding a chimeric Cel7A polypeptide operatively linked to one or more expression control sequences (e.g., transcription control sequences or translation control sequences). In one aspect, an expression vector may comprise a nucleic acid encoding a chimeric Cel7A polypeptide, as described herein, operably linked to at least one regulatory sequence. It should be understood that the design of the expression vector may depend on such factors as the choice of the host cell to be transformed and/or the type of polypeptide to be expressed.

Expression and recombinant vectors may contain a selectable marker, a gene encoding a protein necessary for survival or growth of a host cell transformed with the vector. The presence of this gene allows growth of only those host cells that express the vector when grown in the appropriate selective media. Typical selection genes encode proteins that confer resistance to antibiotics or other toxic substances, complement auxotrophic deficiencies, or supply critical nutrients not available from a particular media. Markers may be an inducible or non-inducible gene and will generally allow for positive selection. Non-limiting examples of selectable markers include the ampicillin resistance marker (i.e., beta-lactamase), tetracycline resistance marker, neomycin/kanamycin resistance marker (i.e., neomycin phosphotransferase), dihydrofolate reductase, glutamine synthetase, and the like. The choice of the proper selectable marker will depend on the host cell, and appropriate markers for different hosts as understood by those of skill in the art.

Suitable expression vectors may include (or may be derived from) plasmid vectors that are well known in the art, such as those commonly available from commercial sources. The Examples below illustrate the construction of exemplary expression vectors containing chimeric Cel7A polypeptides. Vectors can contain one or more replication and inheritance systems for cloning or expression, one or more markers for selection in the host, and one or more expression cassettes. The inserted coding sequences can be synthesized by standard methods, isolated from natural sources, or prepared as hybrids. Ligation of the coding sequences to transcriptional regulatory elements or to other amino acid encoding sequences can be carried out using established methods. A large number of vectors, including bacterial, fungal, yeast, and mammalian vectors, have been described for replication and/or expression in various host cells or cell-free systems, and may be used with the secretion sequences described herein for simple cloning or protein expression.

Certain embodiments may employ fungal promoters or regulatory elements. For example, a promoter or regulatory element may comprise the CBH1 promoter from *T. reesei* and the trpC terminator from *A. nidulans*. The efficiency of expression may be enhanced by the inclusion of enhancers that are appropriate for the particular fungal cell system which is used, such as those described in the literature.

It will be appreciated by one skilled in the art that use of recombinant DNA technologies can improve control of expression of transformed nucleic acid molecules by manipulating, for example, the number of copies of the nucleic acid molecules within the host cell, the efficiency with which those nucleic acid molecules are transcribed, the efficiency with which the resultant transcripts are translated, and the efficiency of post-translational modifications. Additionally, the promoter sequence might be genetically engineered to improve the level of expression as compared to the native promoter. Recombinant techniques useful for controlling the expression of nucleic acid molecules include, but are not limited to, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites), modification of nucleic acid molecules to correspond to the codon usage of the host cell, and deletion of sequences that destabilize transcripts.

The nucleic acids, including parts or all of expression vectors, may be isolated directly from cells, or, alternatively, the polymerase chain reaction (PCR) method can be used to produce the nucleic acids. Primers used for PCR can be synthesized using the sequence information provided herein and can further be designed to introduce appropriate new restriction sites, if desirable, to facilitate incorporation into a given vector for recombinant expression. The nucleic acids can be produced in large quantities by replication in a suitable host cell (e.g., prokaryotic or eukaryotic cells such as bacteria, fungi, yeast, insect or mammalian cells). The production and purification of nucleic acids are described, for example, in Sambrook et al., 1989; F. M. Ausubel et al., 1992, Current Protocols in Molecular Biology, J. Wiley and Sons, New York, N.Y.

The nucleic acids described herein may be used in methods for production of chimeric Cel7A polypeptides through incorporation into cells, tissues, or organisms. In some embodiments, a nucleic acid may be incorporated into a vector for expression in suitable host cells. The vector may then be introduced into one or more host cells by any method known in the art. One method to produce an encoded protein includes transforming a host cell with one or more recombinant nucleic acids (such as expression vectors) to form a recombinant cell. The term "transformation" is generally used herein to refer to any method by which an exogenous nucleic acid molecule (i.e., a recombinant nucleic acid molecule) can be inserted into a cell, but can be used interchangeably with the term "transfection."

In additional embodiments, the activity of a Cel7A polypeptide may be increased by expressing a nucleic acid encoding the Cel7A polypeptide in a heterologous host cell and isolating the Cel7A polypeptide from the cell. For example, the expression of wild-type *P. funiculosum* Cel7A in *T. reesei* may result in a Cel7a polypeptide with higher activity than wild-type *P. funiculosum* Cel7A expressed in or isolated from native wild-type *P. funiculosum* cells. Such increased activity can be seen in the experiments described in Example 7. Without wishing to be bound by any one theory, this observed activity increase may be due to differences in glycosylation patterns with glycans playing some role here in altering enzyme activity. Methods of making these improved Cel7A polypeptides and improved Cel7A polypeptides expressed in heterologous host cells are additional embodiments contemplated herein. In certain embodiments, the Cel7A polypeptide, such as *P. funiculosum* Cel7A, is expressed in *T. reesei*.

Non-limiting examples of suitable host cells include cells from microorganisms such as bacteria, yeast, fungi, and filamentous fungi. Exemplary microorganisms include, but are not limited to, filamentous fungi from the genera *Trichoderma* (e.g., *T. reesei*, *T. viride*, *T. koningii*, or *T. harzianum*), *Penicillium* (e.g., *P. funiculosum*), *Humicola* (e.g., *H. insolens*), *Chrysosporium* (e.g., *C. lucknowense*), *Gliocladium*, *Aspergillus* (e.g., *A. niger*, *A. nidulans*, *A. awamori*, or *A. aculeatus*), *Fusarium*, *Neurospora*, *Hypo-* crea (e.g., *H. jecorina*), and *Emericella*; yeasts from the genera *Saccharomyces* (e.g., *S. cerevisiae*), *Pichia* (e.g., *P. pastoris*), or *Kluyveromyces* (e.g., *K. lactis*). Cells from plants such as *Arabidopsis*, barley, citrus, cotton, maize, poplar, rice, soybean, sugarcane, wheat, switch grass, alfalfa, miscanthus, and trees such as hardwoods and softwoods are also contemplated herein as host cells.

Host cells can be transformed, transfected, or infected as appropriate by any suitable method including electroporation, calcium chloride-, lithium chloride-, lithium acetate/poly ene glycol-, calcium phosphate-, DEAE-dextran-, liposome-mediated DNA uptake, spheroplasting, injection, microinjection, microprojectile bombardment, phage infection, viral infection, or other established methods. Alternatively, vectors containing the nucleic acids of interest can be transcribed in vitro, and the resulting RNA introduced into the host cell by well-known methods, for example, by injection. Exemplary embodiments include a host cell or population of cells expressing one or more nucleic acid molecules or expression vectors described herein (for example, a genetically modified microorganism). The cells into which nucleic acids have been introduced as described above also include the progeny of such cells.

Vectors may be introduced into host cells such as those from filamentous fungi by direct transformation, in which DNA is mixed with the cells and taken up without any additional manipulation, by conjugation, electroporation, or other means known in the art. Expression vectors may be expressed by filamentous fungi or other host cells episomally or the gene of interest may be inserted into the chromosome of the host cell to produce cells that stably express the gene with or without the need for selective pressure. For example, expression cassettes may be targeted to neutral chromosomal sites by recombination.

Host cells carrying an expression vector (i.e., transformants or clones) may be selected using markers depending on the mode of the vector construction. The marker may be on the same or a different DNA molecule. In prokaryotic hosts, the transformant may be selected, for example, by resistance to ampicillin, tetracycline or other antibiotics. Production of a particular product based on temperature sensitivity may also serve as an appropriate marker.

Host cells may be cultured in an appropriate fermentation medium. An appropriate, or effective, fermentation medium refers to any medium in which a host cell, including a genetically modified microorganism, when cultured, is capable of growing or expressing the chimeric polypeptides described herein. Such a medium is typically an aqueous medium comprising assimilable carbon, nitrogen and phosphate sources, but can also include appropriate salts, minerals, metals and other nutrients. Microorganisms and other cells can be cultured in conventional fermentation bioreactors and by any fermentation process, including batch, fed-batch, cell recycle, and continuous fermentation. The pH of the fermentation medium is regulated to a pH suitable for growth of the particular organism. Culture media and conditions for various host cells are known in the art. A wide range of media for culturing filamentous fungi, for example, are available from ATCC. Exemplary culture/fermentation conditions and reagents are provided in the Examples that follow.

The nucleic acid molecules described herein encode chimeric Cel7A polypeptides with amino acid sequences such as those represented by SEQ ID NO:6, 8, 10, 12, 14 and 16. As used herein, the terms "protein" and "polypeptide" are synonymous. "Peptides" are defined as fragments or portions of polypeptides, preferably fragments or portions having at least one functional activity as the complete polypeptide sequence. "Isolated" proteins or polypeptides are proteins or polypeptides purified to a state beyond that in which they exist in cells. In certain embodiments, they may be at least 10% pure; in others, they may be substantially purified to 80% or 90% purity or greater. Isolated proteins or polypeptides include essentially pure proteins or polypeptides, proteins or polypeptides produced by chemical synthesis or by combinations of biological and chemical methods, and recombinant proteins or polypeptides that are isolated. Proteins or polypeptides referred to herein as "recombinant" are proteins or polypeptides produced by the expression of recombinant nucleic acids.

Proteins or polypeptides encoded by nucleic acids as well as functional portions or variants thereof are also described herein. Polypeptide sequences may be identical to the amino acid sequence of SEQ ID NO:6, 8, 10, 12, 14 or 16, or may include up to a certain integer number of amino acid alterations. Such protein or polypeptide variants retain functionality as cellulases, and include mutants differing by the addition, deletion or substitution of one or more amino acid residues, or modified polypeptides and mutants comprising one or more modified residues. The variant may have one or more conservative changes, wherein a substituted amino acid has similar structural or chemical properties (e.g., replacement of leucine with isoleucine). Alterations may occur at the amino- or carboxy-terminal positions of the reference polypeptide sequence or anywhere between those terminal positions, interspersed either individually among the amino acids in the reference sequence or in one or more contiguous groups within the reference sequence.

In certain embodiments, the polypeptides may be at least about 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:6, 8, 10, 12, 14 or 16 and possess cellulase function. Percent sequence identity can be calculated using computer programs (such as the BLASTP and TBLASTN programs publicly available from NCBI and other sources) or direct sequence comparison. Polypeptide variants can be produced using techniques known in the art including direct modifications to isolated polypeptides, direct synthesis, or modifications to the nucleic acid sequence encoding the polypeptide using, for example, recombinant DNA techniques.

Modified polypeptides, including those with post-translational modifications, are also contemplated herein. Isolated polypeptides may be modified by, for example, phosphorylation, methylation, farnesylation, carboxymethylation, geranyl geranylation, glycosylation, acetylation, myristoylation, prenylation, palmitation, amidation, sulfation, acylation, or other protein modifications. They may also be modified with a label capable of providing a detectable signal, either directly or indirectly, including, but not limited to, radioisotopes and fluorescent compounds. The polypeptides may be useful as antigens for preparing antibodies by standard methods. Monoclonal and polyclonal antibodies that specifically recognize the polypeptides disclosed herein are contemplated.

Chimeric polypeptides such as those represented by SEQ ID NO:6, 8, 10, 12, 14 or 16 may be expressed, isolated and used as stand-alone polypeptides. They may also be fused to one or more additional polypeptides (using, for example, recombinant technology) to create a fusion protein with an additional complete polypeptide or a functional domain of a polypeptide. Suitable fusion segments include segments that can enhance a protein's stability, provide other desirable biological activity, or assist with the purification of the protein (e.g., by affinity chromatography). A suitable fusion segment can be a domain of any size that has the desired function (e.g., imparts increased stability, solubility, action or biological activity; or simplifies purification of a protein).

Chimeric polypeptides may be detected by any assay known in the art to detect a protein of interest. Examples include enzymatic activity assays, detection with specific antibodies (immunoblotting, ELISA, etc.), and other suitable detection techniques.

Chimeric polypeptides may also be isolated or recovered from the media used in host cell cultures or cell-free expression systems. The phrase "recovering the protein" refers to collecting the whole culture medium containing the protein and need not imply additional steps of separation or purification. Proteins can be purified using a variety of standard protein purification techniques, such as affinity chromatography, ion exchange chromatography, filtration, electrophoresis, hydrophobic interaction chromatography, gel filtration chromatography, reverse phase chromatography, concanavalin A chromatography, chromatofocusing, differential solubilization, preparative disc-gel electrophoresis, isoelectric focusing, HPLC, reversed-phase HPLC, or countercurrent distribution. The polypeptide may contain an additional protein or epitope tag that facilitates detection or purification, such as c-myc, haemagglutinin (HA), polyhistidine, GLU-GLU, FLAG-tag, glutathione-S-transferase (GST), green fluorescent protein (GFP), or maltose binding protein (MBP). Such tags may be removed following the recovery of the polypeptide.

Polypeptides may be retrieved, obtained, or used in "substantially pure" form, a purity that allows for the effective use of the protein in any method described herein or known in the art. For a protein to be most useful in any of the methods described herein or in any method utilizing enzymes of the types described herein, it is most often substantially free of contaminants, other proteins and/or chemicals that might interfere or that would interfere with its use in the method (e.g., that might interfere with enzyme activity), or that at least would be undesirable for inclusion with a protein.

Methods for degrading cellulose and materials containing cellulose using the chimeric Cel7A polypeptides are also provided herein. For example, the chimeric Cel7A polypeptides may be used in compositions to help degrade (e.g., by liquefaction) a variety of cellulose products (e.g., paper, cotton, etc.) in landfills. The chimeric Cel7A polypeptides may also be used to enhance the cleaning ability of detergents, function as a softening agent or improve the feel of cotton fabrics (e.g., stone washing or biopolishing) or in feed compositions.

Cellulose containing materials may also be degraded to sugars using the chimeric Cel7A polypeptides. Ethanol may be subsequently produced from the fermentation of sugars derived from the cellulosic materials. Exemplary cellulose-containing materials include bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, corn fiber, grasses, wheat, wheat straw, barley, barley straw, hay, rice straw, switchgrass, waste paper, sugar cane bagasse, sorghum, soy, components obtained from milling of grains, trees, branches, roots, leaves, wood (e.g., poplar) chips, sawdust, shrubs and bushes, vegetables, fruits, flowers and animal manure.

Biofuels such as ethanol may be produced by saccharification and fermentation of lignocellulosic biomass such as trees, herbaceous plants, municipal solid waste and agricultural and forestry residues. Typically, saccharification is carried out by contacting the lignocellulosic biomass with an enzyme cocktail that includes one or more Family 7 cellulases such as the chimeric Cel7A polypeptides described herein. Such enzyme cocktails may also contain one or more endoglucanases (such as the Family 5 endoglucanase E1 from *Acidothermus cellulolyticus*) or one or more β-glucosidases (e.g., a β-glucosidase from *A. niger*) to optimize hydrolysis of the lignocelluloses. Additional suitable endoglucanases include EGI, EGII, EGIII, EGIV, EGV or Cel7B (e.g., Cel7B from *T. reesei*). Enzyme cocktails may also include accessory enzymes such as hemicellulases, pectinases, oxidative enzymes, and the like.

Enzymes with the ability to degrade carbohydrate-containing materials, such as cellulases with endoglucanase activity, exoglucanase activity, or β-glucosidase activity, or hemicellulases with endoxylanase activity, exoxylanase activity, or β-xylosidase activity may be included in enzyme cocktails. Examples include enzymes that possess cellobiohydrolase, α-glucosidase, xylanase, β-xylosidase, α-galactosidase, β-galactosidase, α-amylase, glucoamylases, arabinofuranosidase, mannanase, β-mannosidase, pectinase, acetyl xylan esterase, acetyl mannan esterase, ferulic acid esterase, coumaric acid esterase, pectin methyl esterase, laminarinase, xyloglucanase, galactanase, glucoamylase, pectate lyase, chitinase, exo-β-D-glucosaminidase, cellobiose dehydrogenase, ligninase, amylase, glucuronidase, ferulic acid esterase, pectin methyl esterase, arabinase, lipase, glucosidase or glucomannanase activities.

A lignocellulosic biomass or other cellulosic feedstock may be subjected to pretreatment at an elevated temperature in the presence of a dilute acid, concentrated acid or dilute alkali solution for a time sufficient to at least partially hydrolyze the hemicellulose components before adding the enzyme cocktail. Additional suitable pretreatment regimens include ammonia fiber expansion (AFEX), treatment with hot water or steam, or lime pretreatment.

Separate saccharification and fermentation is a process whereby cellulose present in biomass is converted to glucose that is subsequently converted to ethanol by yeast strains. Simultaneous saccharification and fermentation is a process whereby cellulose present in biomass is converted to glucose and, at the same time and in the same reactor, converted into ethanol by yeast strains. Enzyme cocktails may be added to the biomass prior to or at the same time as the addition of a fermentative organism.

The resulting products after cellulase degradation may also be converted to products other than ethanol. Examples include conversion to higher alcohols, hydrocarbons, or other advanced fuels via biological or chemical pathways, or combination thereof.

EXAMPLES

Example 1

Construction of Expression Vectors

An expression vector was designed, designated pTREXP002, which contains the expression cassette for the *A. nidulans* AMDS gene allowing for growth on acetamide as the sole nitrogen source. DNA encoding the chimeric Cel7A proteins were synthesized and subcloned in this plasmid between the CBH1 promoter from *T. reesei* and the trpC terminator from *A. nidulans*. The insertion of target genes in the correct orientation was confirmed by PCR and digestion with restriction enzymes. Plasmid DNAs prepared from E. coli were used for transformation of T. reesei.

Figure 10:
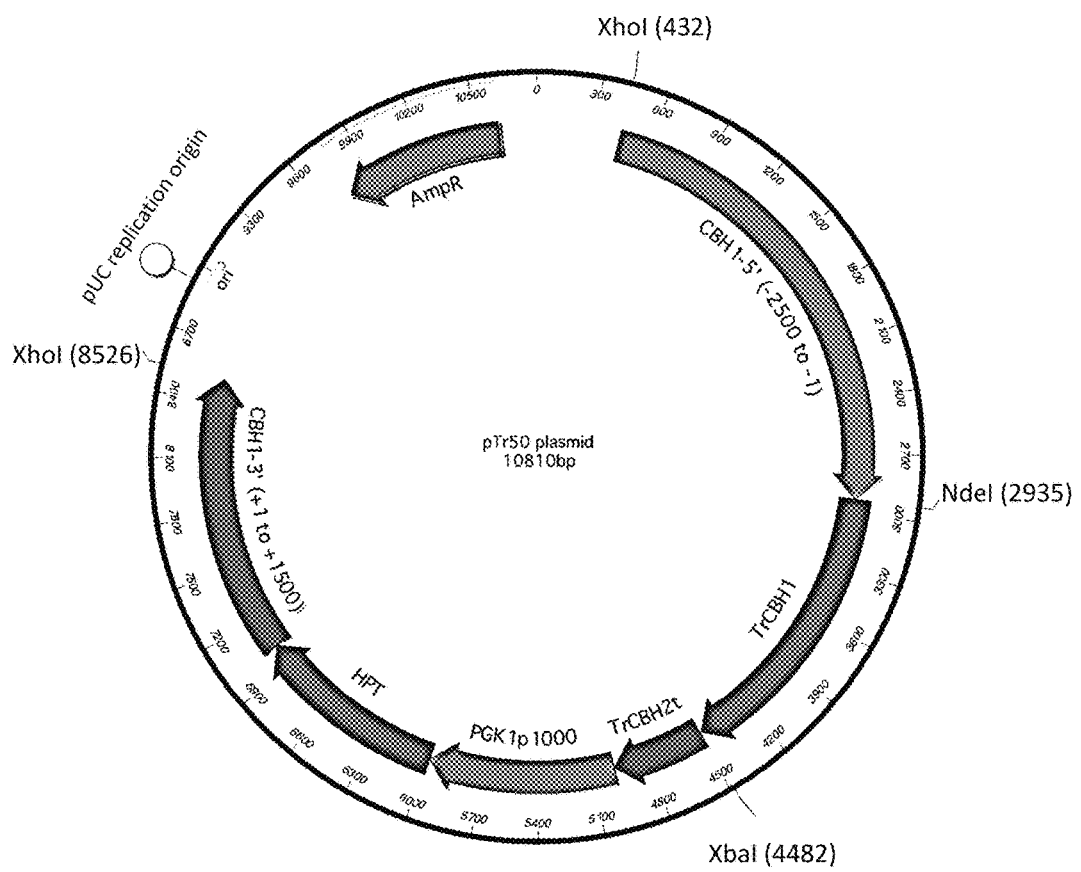
FIG. 10 shows a diagram of plasmid pTr50 for expression of chimeric genes in *T. reesei* strain AST1116. The gene of interest can be added by digesting the plasmid and the insert with NdeI and XbaI. The vector may then linearized by digesting with XhoI.

The expression vector pTr50 was developed for expression of chimeric genes in the cbh1Δ T. reesei strain AST1116. This vector uses hpt gene from E. coli as the selection marker and the expression of desired genes is driven by the T. reesei cbh1 promoter. A diagram of this vector is presented in FIG. 10.

All restriction enzymes, T4 DNA ligase, Taq DNA polymerase and related buffers and chemicals were obtained from New England Biolabs (Beverly, Mass., USA). Plasmid constructions, E. coli transformations, DNA isolation and other DNA manipulation techniques were used as described in standard protocols. The oligonucleotide primers used in this study are listed below in Table 2.

T. reesei spheroplasts were prepared and transformed with slight modifications of published methods (See Penttila et al. (Gene 61:155 (1991)). Spheroplasts were generated from 30-48 hour cultures in PD or CML started with spore stocks. Mycelia were collected by filtration through Mira cloth, washed with water and incubated in 0.6M KCl containing 3 mg/ml Glucanex (Sigma) and 2 mg per ml lysozyme (Sigma) for 3-4 hours at 30° C. with gentle shaking (90 rpm). After 7 hours of recovery period of transformed spheroplasts in rich medium, PD or CML, the hygromycin-B-resistant transformants were selected by mixing the transformed spheroplasts with 10 ml of PD or CML agar media containing 1.0M sorbitol and 100 mg/L hygromycin B and pouring over Petri dishes containing the same medium. The spheroplasts transformed for ability to utilize acetamide as

TABLE 2

| Name | Sequence | Description | SEQ ID NO: |
|---|---|---|---|
| AS096 | TGCTCTTTTGAGCTACAAGAACCTGTG G | 5' primer external to cbh1 deletion cassette for Rut C-30 | 17 |
| AS097 | GAACAAGCTTTTTGGCATCGTGGATCC ATT | 3' primer external to cbh1 deletion cassette for Rut C-30 | 18 |
| AS104 | ACTTACTAGTATGCCTCAATCCTGGGA AGAACTGG | 5' primer to clone Aspergillus nidulans amdS gene | 19 |
| AS105 | ATTGACTAGTCTATGGAGTCACCACAT TTCCCAG | 3' primer to clone Aspergillus nidulans amdS gene | 20 |
| A5113 | CTGGAAAGTGACGCCATTCTGGACAT | 3' primer in cbh1 CD S | 21 |
| A5117 | ATGAAGAAGCCGGAGTTGACTGCAAC | 5' primer inside cbh1 CD S | 22 |
| AS120 | CTCCCAGCTGACTGGCCAATTC | 5' primer inside cbh1 | 23 |
| AS123 | CGGCTTCTTCATACTAGTGGCAGGAA AT | 3' primer spanning PGK1 promoter and E. coli hph CDS in deletion cassette | 24 |
| AS133 | AGCACTCTCTCGCCCAATGATGTC | 5' primer external to cbh1 deletion cassette for QM6a | 25 |
| AS134 | TCCGACTCTTTTAATCATCGCGTATAT CC | 3' primer in PGK1p in deletion cassette for QM6a | 26 |
| A5135 | AAGAGTATGATCCGGAGGCGTACCA | 5' primer in amdS CDS in deletion cassette for QM6a | 27 |
| AS136 | CCAATAATACATTAACAACACAGTTTC AGCCC | 3' primer external to cbh1 deletion cassette for QM6a | 28 |

Example 2

Transformation of T. reesei

Potato dextrose (PD), obtained from Sigma, and Complete Medium with lactose (CML) were used as the routine culture media. PDA (PD with agar) was used for sporulation of various Trichoderma strains. The CML medium contained, per liter: yeast extract (5 g) tryptone (5 g), lactose (10 g) and Clutterbuck's salts. The pH of this medium was adjusted to 7.5 with KOH. The minimal medium (MMA) for growth on acetamide for nitrogen source contained, per liter: glucose (20 g), KH$_2$PO$_4$ (15 g), MgSO$_4$ (0.6 g), CaCl$_2$ (0.6 g), sorbitol (182.2 g), acetamide (0.59 g), CsCl (2.10 g), Agar (20 g), FeSO$_4$.7H$_2$O (0.005 g), MnSO$_4$.H$_2$O (0.0016 g), ZnSO$_4$.7H$_2$O (0.0014 g) and CoCl$_2$ (0.002 g). For solidification, all media contained 2% agar. For spheroplast transformation, CML, PDA and MMA contained 1 M sorbitol. All cultures of T. reesei were grown at 30° C. The liquid cultures were grown in shake flasks with shaking at 225 rpm.

sole nitrogen source were selected on the MMA media containing acetamide as the sole nitrogen following the protocol described by Penttila et al. Transformants were purified by two rounds of sporulation and testing of single spores for resistance to hygromycin B or ability to use acetamide as the sole nitrogen source.

Example 3

Strains and Cultivation for Expression of Proteins

The Trichoderma reesei strains, QM6a and Rut C-30, obtained from the American Type Culture Collection, were used as the base strains from which the expression strains were constructed. The cbh1 CDS and cbh1 promoter were deleted in QM6a to create the cbh1Δ strain, AST1116.

T. reesei Rut C-30 was used both in wild type form as well as genetically altered form for cellulase production. Seed cultures were prepared in triplicate by soaking the spores for 48 hours in tissue culture tubes at 30° C. at 150 rpm in 5 mL containing Vogel minimal media with a 2.5% w/v glucose solution. Subsequently, the seed cultures were used to inoculate 500 mL of Vogel's minimal media with a 2.5% w/v glucose solution for an additional 72 hours. Vogel's 50× salts were used, which consisted of 150 g $Na_3$ citrate. $2 H_2O$, 250 g of $KH_2PO_4$, 100 g of $NH_4NO_3$, 10 g of $MgSO_4$, 5 g of $CaCl_2$, 5 ml of trace element solution and 2.5 mL of a 1% w/v Botin solution dissolved into 750 mL of distilled water. The trace elements consisted of 5 g of citric acid. $1 H_2O$, 5 g $ZnSO_4.7H_2O$, 1 g of $Fe(NH_4)_2(SO_4)_2.6 H_2O$, 0.25 g of $CuSO_4.5 H_2O$, 0.05 g of $MnSO_4.1 H_2O$, 0.05 g of anhydrous $H_3BO_3$, and 0.05 g of $Na_2MoO_4.2 H_2$ dissolved into 95 mL of distilled water. These seed cultures were transferred to a 1 L shake flask (500 mL actual volume) and incubated at 30° C. at 150 rpm. After 72 hours of growth in the shake flasks, the fungal broths were screened for any potential contamination and one of the 1 L shakes flasks was used to inoculate the fermentor. The other shake flasks received 60 mL of 20% w/v lactose resulting in a final lactose concentration of approximately 2% w/v. These shake flasks were then incubated for an additional 96 hours at 30° C. at 150 rpm.

Example 4

Fermentations for Expression of Proteins

The fermentations were performed in both 5 and 3 L New Brunswick scientific Bioflow 3000 fermentors with an operating volume of 4 and 2 L, respectively. Vogel's minimal media was chosen to use in the fermentors due to the low foaming associated with this media. The fermentation temperature was maintained at 30° C. and the pH was maintained between 5.0 and 5.6 depending on the initial pH of the fermentor after inoculation. The pH was maintained using 1 M KOH and 1 M HCl via a computer controlled feedback system. During the initial phase of the fermentation, the acid feedback control was turned off, and turned on again when the system began to run low on nutrients. The amount of foam was controlled with the use of Sigma Aldrich Antifoam 204 and the dissolved oxygen was controlled via a feedback system with the setting of 30% dissolved oxygen relative to air.

The glucose concentration was monitored by taking time points throughout the fermentation and then measuring the glucose concentration via Megazyme GOPOD. The main goal with these fermentations was to obtain a large amount of fungal mass with glucose and as the glucose concentration dwindled, we began feeding lactose to the system to produce a lactose limited batch of proteins. The dissolved oxygen probes were not reliable enough to control the feeding of a 5% w/v lactose solution. Therefore the lactose solution was fed at a constant rate of 1 mL/min once the glucose concentration reached approximately 0.7%. After this, the lactose concentration was monitored using Megazyme Lactose and D-Galactose assay. The goal was to keep the lactose at a concentration between 0.5% and 1% w/v during the rest of the fermentation. During this phase, we monitored the production of the chimeras via measuring the activity on PnPl. Once the activity on PnPl leveled off, the fermentations were stopped, and the fungal broths were filtered and concentrated. The remaining shake flasks were harvested to verify protein production within the chimera in the event the fermentation failed signaling that the lack of protein expression was due to a bad fermentation run and not because the chimera strain failed to express.

For additional fermentations, the transformed cell culture was streaked on a Potato Dextrose Agar plate and allowed to grow 2-3 days until a well lawn plate of spores was achieved. An approximately 0.5 cm plug was extracted from the plate and deposited into 50 ml of liquid growth media in a 250 mL shake flask. The growth media consisted of Mandel's Growth Media with 5% lactose as the carbon source in lieu of glucose, and 0.5% tryptone added. The culture was grown at 28° C. with agitation for 48 hours, whereupon the entire 50 mL was transferred to 1 L of the same media, in a 2.8 L shake flask. The culture was again grown at 28° C. with agitation for 3 days, after which the entire 1 L was transferred to 7 L of the same media, in a bioreactor. The bioreactors were 15 L working volume vessels manufactured by New Brunswick and controlled via New Brunswick's BioFlo3000 system. The total of 8 L was grown with mixing at 200 rpm via rushton style impellers, purged with 1.0 L/min of filtered air, kept at a strict 28° C., and pH controlled at 4.8. The acid and base used for pH control was HCl and KOH, respectively. The cell culture was grown for 4 days, after which the entire culture broth was drained, filtered through nylon to remove all cell mass, and concentrated via tangential flow filtration. The concentrated broth was buffer exchanged into 20 mM Bis-Tris pH 6.5, and brought up to about 200 mL, where it was then subjected to purification.

Example 5

Purification of Proteins

Culture supernatants were collected as follows. Mycelial mass was removed by gravity filtration using Miracloth (EMD Biosciences, Gibbstown, N.J.). The supernatant obtained was passed, under vacuum, through a series of glass fiber filters with descending pore sizes ranging from 2.7 µm to 0.7 µm (Millipore, Billerica, Mass.). This was followed by vacuum filtration through 0.45 µm and 0.2 µm bottle-top filtration devices (Nalgene, Rochester, N.Y.). After filtration, supernatants were concentrated to about $\frac{1}{50}^{th}$ original volume and exchanged into 20 mM Bis-Tris, pH 6.5.

The concentrated supernatants were amended to 2 M $NH_4SO_4$ by addition of an equal volume of 30 mM Bis-Tris pH 5.8, 4 M $NH_4SO_4$, loaded onto a Tricorn 10/100 column (GE Healthcare, Piscataway, N.J.) packed with Source 15Phe Hydrophobic Interaction Chromatography medium (GE Healthcare), and eluted using a 25 column volume linear gradient of 20 mM Bis-Tris, pH 5.8, 2M $NH_4SO_4$. Fractions were assayed for Cel7A activity by adding 25 µL of each fraction to 150 µL of a solution of 2 mM p-nitropheno-β-lactopyranoside (pNPL; Sigma-Aldrich, St Louis, Mont.) in 50 mM Sodium Acetate, pH 5.0 in a microtiter plate. Reactions were incubated 30 min at 45° C. and quenched by addition of 25 µL 1 M sodium carbonate. Absorbance was read at 405 nm with absorbances compared to a standard curve of p-nitrophenol in 50 mM sodium acetate pH 5.0. Fractions with significant pNPL activity were pooled and examined by SDS-PAGE and western blotting using polyclonal antibodies raised against the catalytic domain of T. reesei or P. funiculosum Cel7A, as required. Pooled peaks containing rCel7A were desalted into 20 mM Bis-Tris, pH 6.5 using two Hi Prep 26/10 desalting columns in series. The resultant protein solution was loaded onto a Tricorn 10/100 column packed with Source 15Q anion-exchange medium (GE Healthcare) and eluted with a 20 column volume linear gradient of 20 mM Bis-Tris pH 6.5, 1M NaCl. Fractions were assayed and visualized as above, concentrated to a volume less than 13 mL in 10 kDa MWCO Amicon Centricon Plus-20 centrifugal concentration devices and loaded onto a HiLoad Superdex75 26/60 size exclusion column and eluted at 1 mL/min in 20 mM Sodium Acetate, pH 5.0, 100 mM NaCl. Fractions were assayed and visualized as above, pooling fraction containing a single, western blot positive band. The purified rCel7A solution obtained was quantified using the bicinchoninic acid protein assay (Pierce, Rockford, Ill.).

Example 6

Activity Assays

Cellobiohydrolase activity was measured as the saccharification of the cellulose fraction of a sample of a standard dilute-acid-pretreated corn stover by the cellobiohydrolase when used in conjunction with two other enzymes at standard loadings (1) the endoglucanase *Acidothermus cellulolyticus* E1 (Cel5A, catalytic domain) loaded at 1.894 mg/g of biomass cellulose and (2) the chromatographically-purified beta-glucosidase from *Aspergillus niger*, loaded at 2.0 mg/g biomass cellulose.

The standard biomass substrate used in the activity assays is NREL dilute-acid-pretreated corn-stover P050921, washed first with water and then with 20 mM acetic acid/sodium acetate buffer, pH 5.0, until the pH of the (buffer) decantate is within 0.03 units of 5.00. From a slurry of this washed biomass material (approximately 9 mg biomass per mL of pH 5.0, 20 mM acetate buffer containing 0.02% sodium azide to retard microbial growth), a series of biomass substrate aliquots were prepared in 2.0-mL HPLC vials, in such a way that each vial contains 8.5 mg biomass cellulose (which, given that the "glucan" content of this batch of pretreated stover is 59.1%, requires 14.38 mg of biomass per digestion vial). Biomass dry weights for each batch of assay vials were verified by dry-weight determinations on a group of five samples co-pipetted into pre-tared vials. The acceptable relative standard deviation for a batch of biomass assay aliquots is 1% or less, with a preferred value of 0.8% or less. Adjustment of these biomass assay aliquots to a 1.7-mL final volume results in a cellulose concentration of 5 mg/mL.

Cellobiohydrolase assays were conducted in triplicate vials at 40° C., pH 5.0 in 20 mM azide-containing acetate buffer, with continuous mixing by inversion at 10 rpm while immersed in a water bath. At various times during the digestion, the vials were removed from the rotator, representative 100-µL samples containing both solids and liquid were removed from the well-stirred contents and diluted 18-fold into glass HPLC vials. The primary digestion vials were immediately resealed and returned to the rotator in the assay 40° C. water bath so that the assay digestions may continue. The vials containing the withdrawn and diluted samples of digestion mixture were then crimp-sealed and immersed in a boiling-water bath for 10 minutes to denature the enzymes and terminate the reaction. The contents of the boiled time-sample vials were then syringe-filtered (0.2-micron Acrodisc) into a third set of vials for sugar analysis by HPLC on a BioRad HPX-87 H column operated at 65° C. with 0.01 N $H_2SO_4$ as the eluent at 0.6 mL/min and refractive-index detection. Values for individual sugar concentrations in the digestion vials were back-calculated from the values measured by HPLC, and then used to construct saccharification progress-curves in terms of percent of conversion of biomass cellulose.

The "standard performance" against which cellobiohydrolase performances are measured is that of *T. reesei* Cel7A when loaded at 46.68 mg per g cellulose, along with the two standard adjuvant enzymes described above, acting against the substrate aliquots described above. At this loading, and under these conditions, the *T. reesei* enzyme will catalyze conversion of 80% and 90% of the biomass cellulose in the process-relevant digestion times of slightly over one day and approximately 2.5 days, respectively. Activity comparisons of engineered cellobiohydrolases with that of the standard *T. reesei* Cel7A are conducted in two stages. First, the mutant cellobiohydrolases assayed at the same loading (46.68 mg/g cellulose) as that used to measure the activity of the standard *T. reesei* Cel7A with assays continued until all enzymes have achieved 80% or more saccharification of the biomass cellulose.

From the interpolated times of intersection of the respective progress curves with the "80%-conversion" line, a preliminary estimate was made of the loading of the cellobiohydrolase mutant required to reach 80% conversion in the same digestion time that the standard *T. reesei* enzyme, at its standard loading, requires to reach this extent of conversion. This first estimate was based on the assumption, which is mathematically demonstrated for simple systems involving single enzymes and uniformly available soluble substrates, and which been rather well supported by experiments involving more complicated systems, that the reaction time required for a given enzyme to convert a certain proportion of a given initial quantity of substrate is inversely proportional to the enzyme loading.

Figure 11:
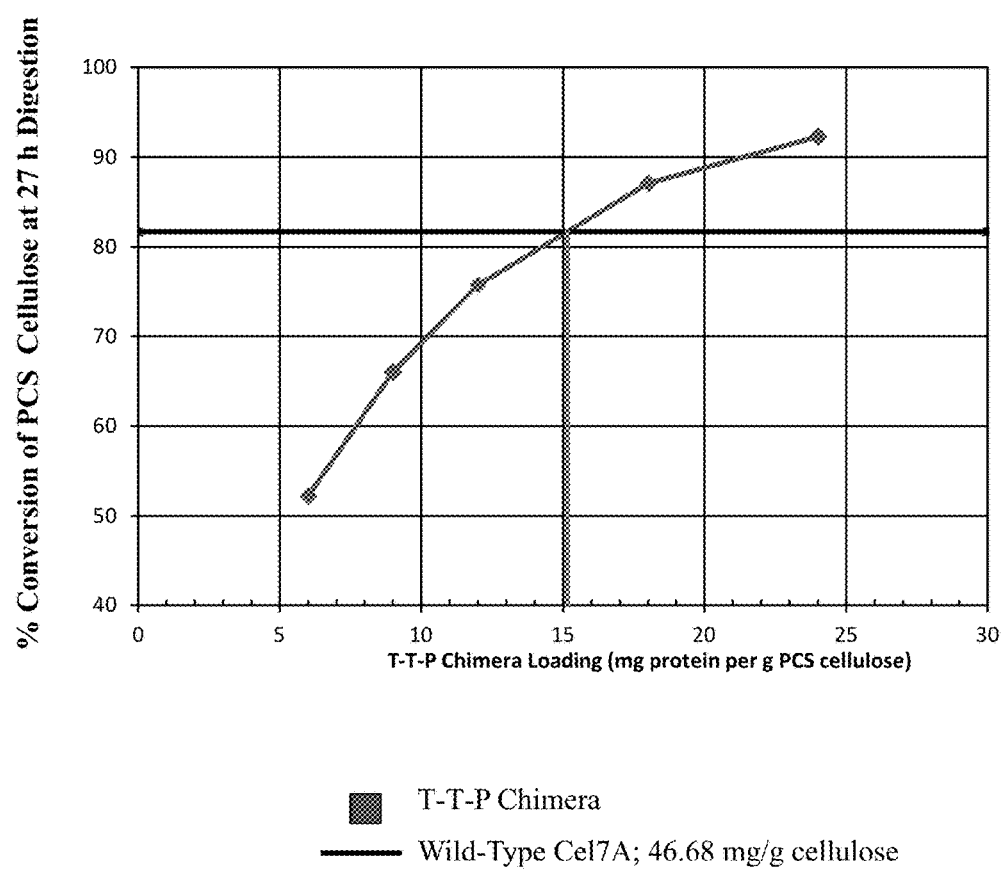
FIG. 11 shows an interpolation to determine equivalence of TTP chimera to 46.68 mg/g cellulose wild-type *T. reesei* Cel7A at about 80% conversion using 27-hour digestion data.

On the basis of the first estimate of Cel7A-equivalence, an additional experimental series was designed to yield a more precise estimate (one not involving the extrapolations involved in the first estimate). A series of loadings (typically four or five) of the cellobiohydrolase mutant was setup to bracket closely the "*T. reesei*-Cel7A-equivalent" loading estimated by the first experimental series, with conversion data being collected for the mutant enzyme and for a standard *T. reesei* control in the time-frame in which the *T. reesei* control would be expected to achieve conversion near 80%. Interpolation in a plot of actual conversion by the mutant enzyme as a function of enzyme loading (FIG. 11), for a given digestion time, was then used to yield a more precise estimate of the loading of the "new" enzyme that would be required to give the same conversion as that delivered by the standard loading of *T. reesei* CBHI. As shown in FIG. 11, approximately 15 mg of the T-T-P chimera per g of cellulose achieved 80% conversion at 27 hours, as compared to 46.68 mg of the wild-type *T. reesei* control per g of cellulose (horizontal line).

Example 7

Activity of Chimeric Enzymes

To engineer enhanced cellobiohydrolases, and to understand the role of the individual sub-domains in processive hydrolysis, the domains of the *T. reesei* Cel7A enzyme were swapped with those from the *P. funiculosum* Cel7A. The *P. funiculosum* enzyme exhibits somewhat higher activity than the *T. reesei* Cel7A enzyme, but the mechanistic basis for the activity differences remains unknown. Table 3 shows the chimeric enzymes screened for activity in this study. These enzymes were expressed in a strain of *T. reesei* lacking the native Cel7A gene, as described above. T=*T. reesei* and P=*P. funiculosum*.

TABLE 3

| CBM | Linker | Catalytic Domain |
|-----|--------|------------------|
| T   | T      | T                |
| P   | P      | P                |

TABLE 3-continued

| CBM | Linker | Catalytic Domain |
|-----|--------|------------------|
| T   | T      | P                |
| P   | P      | T                |
| P   | T      | P                |

Figure 12:
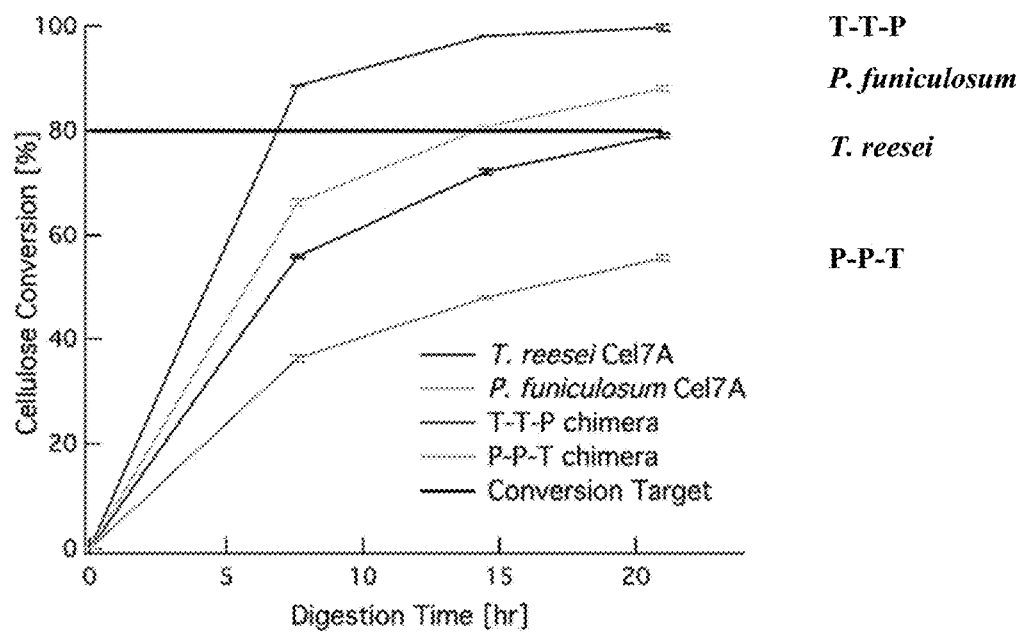
FIG. 12 shows conversion of dilute-acid pretreated corn stover as a function of time. The chimeras are listed as shown in Table 3 in the order of CBM-Linker-Catalytic Domain. T=*T. reesei* and P=*P. funiculosum*.
Figure 13:
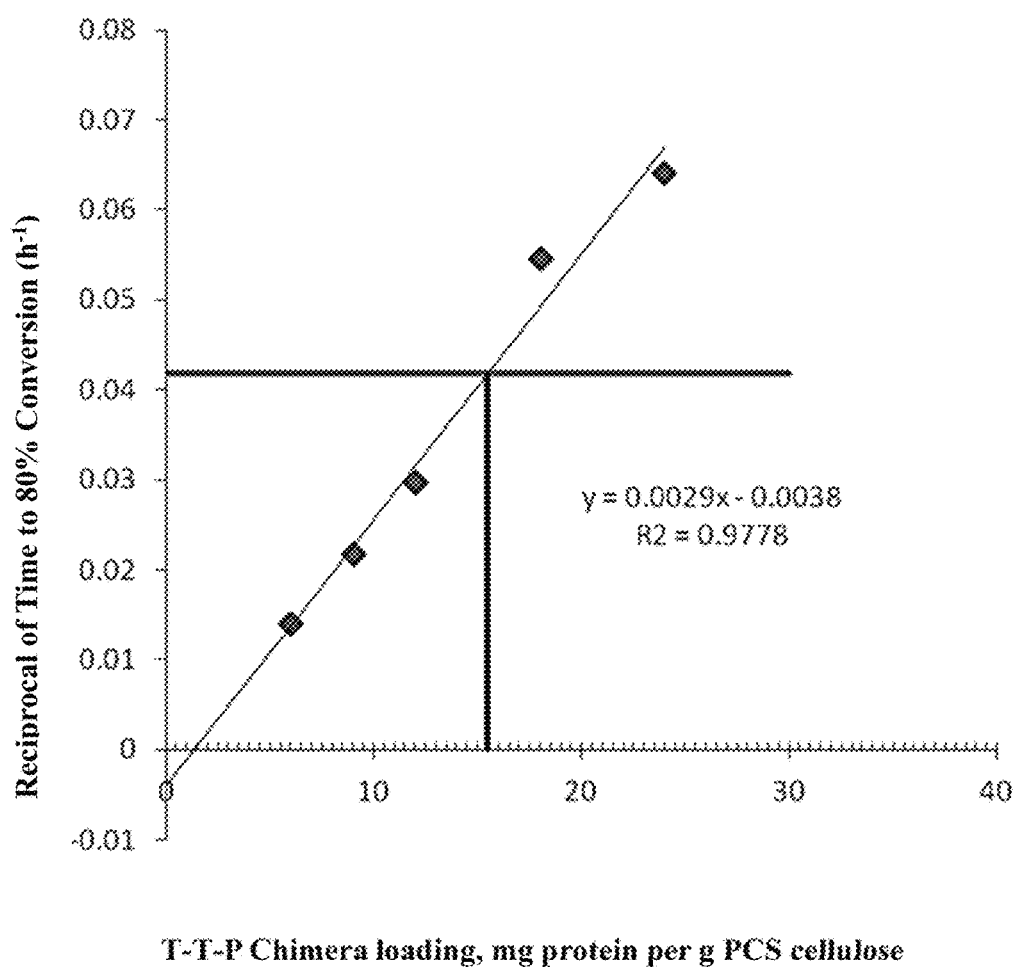
FIG. 13 illustrates additional activity data for the TTP chimera.

Several of the Family 7 cellulases listed in Table 3 were screened on dilute acid pretreated corn stover at a loading of 46 mg of total enzyme per gram of cellulose. For synergy purposes, we added a Family 5 endoglucanase, E1 from *Acidothermus cellulolyticus* and a β-glucosidase from *Aspergillus niger*. The results from the screening are shown in FIG. 12. Cellulase activity is compared as the time to reach 80% conversion, which is the target conversion for industrial-scale biochemical conversion processes. FIG. 12 shows that the T-T-P Cel7A chimera has a substantially higher activity than either the *T. reesei* Cel7A or *P. funiculosum* Cel7A controls. Based on the time to reach 80% conversion, the T-T-P chimera exhibits a 3.1-fold improvement in activity at the same loading over the wild-type *T. reesei* Cel7A. Moreover, domain-swapping of these enzymes produced an enzyme with higher activity than the parent enzymes. This result shows, for the first time, that significant activity improvements can be made to Family 7 cellulases, which are the cornerstone of modern enzyme cocktails for production of sugars from lignocellulosic biomass. Additional chimera activity data are presented in FIGS. 13, 14 and 15.

Figure 14:
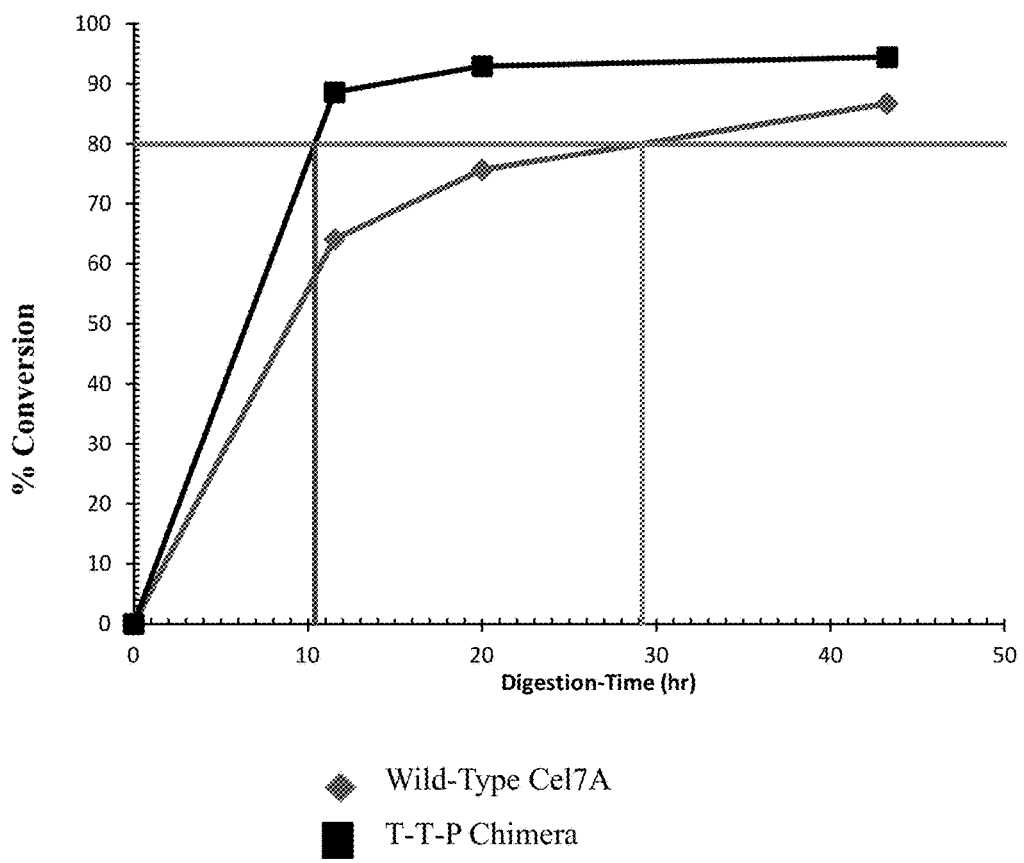
FIG. 14 illustrates a comparison of the time required for the T-T-P chimera and wild-type *T. reesei* Cel7A to reach 80% conversion of pretreated corn stover cellulose at equal enzyme loadings.

FIG. 14 illustrates a comparison of the time required for the T-T-P chimera and wild-type *T. reesei* Cel7A to reach 80% conversion of pretreated corn stover cellulose. Both enzymes were loaded at 8.94 mols/g cellulose (corresponds to 46.7 mg/g cellulose for wild-type *T. reesei* Cel7A) in combination with 1.894 mg *A. cellulolyticus* E1 (CD domain) and 2.0 mg *A. niger* β-glucosidase per g cellulose. The substrate was 5.03 mg/mL cellulose (dilute-acid-pretreated corn stover—59.07% cellulose), pH 5.0 in 20-mM acetate. Assays were carried out at 40° C. with constant mixing by inversion 10 $min^{-1}$ and conversion was monitored by HPLC analysis of released sugars. As depicted in FIG. 14, the T-T-P chimera reaches 80% conversion almost three times faster than the wild-type *T. reesei* Cel7A.

Figure 15:
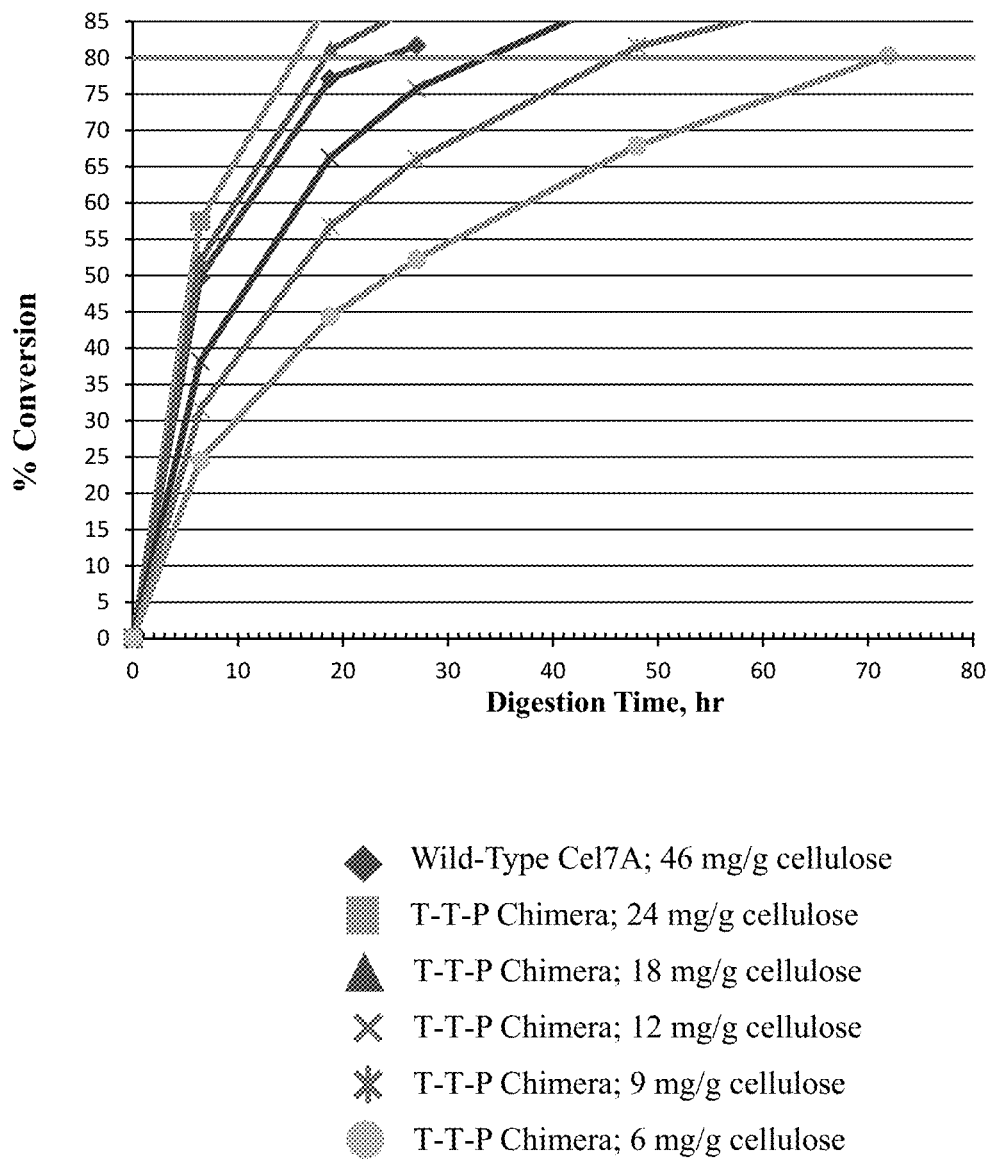
FIG. 15 compares the amount of time to reach 80% conversion of pretreated corn stover cellulose for the wild-type *T. reesei* Cel7A (46 mg/g cellulose) and the T-T-P chimera at various enzyme loadings (24, 18, 12, 9 and 6 mg/g cellulose).

FIG. 15 compares the amount of time to reach 80% conversion of pretreated corn stover cellulose for wild-type *T. reesei* Cel7A (46 mg/g cellulose) and the T-T-P chimera at various enzyme loadings (24, 18, 12, 9 and 6 mg/g cellulose). The data show that significantly less T-T-P chimera enzyme is needed to reach 80% conversion within the same amount of time.

Figure 16:
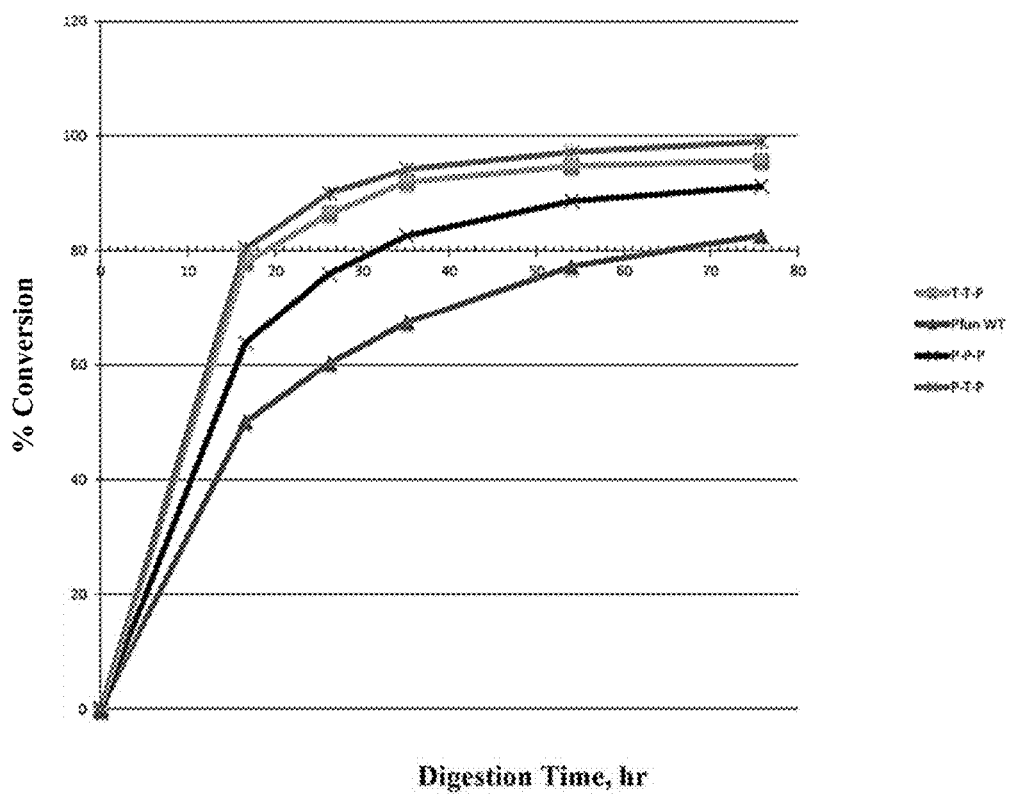
FIG. 16 illustrates a comparison of the time required for the T-T-P chimera (■), P-T-P chimera (*), natively expressed wild-type *P. funiculosum* Cel7A (Pfun WT; ▲) and wild-type *P. funiculosum* Cel7A expressed in *T. reesei* (P-P-P; X) to reach 80% conversion of cellulose at equal enzyme loadings.

As shown in FIG. 16, four enzymes were assayed at a molar loading of 0.45 µmol enzyme per gram of pretreated corn stover cellulose. This corresponds to approximately 23-24 mg of enzyme per gram of cellulose for each assay. In addition to the natively expressed *P. funiculosum* wild type Cel7A enzyme (Pfun WT), the T-T-P chimera, the P-T-P chimera and P-P-P enzyme (*P. funiculosum* wild type Cel7A expressed in *T. reesei*) were tested. As with the above chimeras, each of the two chimeric enzymes in this assay was expressed in *T. reesei*.

The results shown in FIG. 16 demonstrate that T-T-P chimera (about 19 hours) and the P-T-P chimera (about 16.5 hours) require much less time to reach 80% conversion of cellulose than the natively expressed *P. funiculosum* wild type Cel7A enzyme (about 65 hours) or the *P. funiculosum* wild type Cel7A expressed in *T. reesei* (about 31.7 hours) at an equivalent enzyme loading. Further, the *P. funiculosum* wild type Cel7A expressed in *T. reesei* requires less time to reach 80% conversion of cellulose than the natively expressed *P. funiculosum* wild type Cel7A enzyme.

The Examples discussed above are provided for purposes of illustration and are not intended to be limiting. Still other embodiments and modifications are also contemplated.

While a number of exemplary aspects and embodiments have been discussed above, those of skill in the art will recognize certain modifications, permutations, additions and sub combinations thereof. It is therefore intended that the following appended claims and claims hereafter introduced are interpreted to include all such modifications, permutations, additions and sub-combinations as are within their true spirit and scope.

We claim:

1. An isolated chimeric fungal Cel7A polypeptide that has a cellulase activity at least 1.5-fold greater than the wild-type Cel7A polypeptide, comprising a catalytic domain (CD), a carbohydrate-binding molecule (CBM) and a linker domain, wherein at least one of the domains is from a *Penicillium funiculosum* Cel7A polypeptide and at least one of the domains is from a *Trichoderma reesei* Cel7A polypeptide; and wherein each domain is from the *Penicillium funiculosum* or *Trichoderma reesei* Cel7A polypeptides.

2. The isolated chimeric fungal Cel7A polypeptide of claim 1, wherein the chimeric fungal Cel7A polypeptide has a cellulase activity of at least 2-fold greater than the wild-type Cel7A polypeptide.

3. The isolated chimeric fungal Cel7A polypeptide of claim 1, wherein the chimeric fungal Cel7A polypeptide comprises the catalytic domain (CD) from the *Penicillium funiculosum* Cel7A polypeptide.

4. The isolated chimeric fungal Cel7A polypeptide of claim 3, wherein the chimeric fungal Cel7A polypeptide further comprises the carbohydrate-binding molecule (CBM) from the *Trichoderma reesei* Cel7A peptide.

5. The isolated chimeric fungal Cel7A polypeptide of claim 4, wherein the chimeric fungal Cel7A polypeptide further comprises the linker domain from the *Penicillium funiculosum* Cel7A polypeptide.

6. The isolated chimeric fungal Cel7A polypeptide of claim 4, wherein the chimeric fungal Cel7A polypeptide comprises the linker domain from the *Trichoderma reesei* Cel7A polypeptide.

7. The isolated chimeric fungal Cel7A polypeptide of claim 3, wherein the chimeric fungal Cel7A polypeptide further comprises the linker domain from the *Trichoderma reesei* Cel7A polypeptide.

8. The isolated chimeric fungal Cel7A polypeptide of claim 7, wherein the chimeric fungal Cel7A polypeptide further comprises the carbohydrate-binding molecule (CBM) from the *Penicillium funiculosum* Cel7A polypeptide.

9. The isolated chimeric fungal Cel7A polypeptide of claim 1, wherein the chimeric fungal Cel7A polypeptide comprises the catalytic domain (CD) from the *Trichoderma reesei* Cel7A polypeptide.

10. The isolated chimeric fungal Cel7A polypeptide of claim 9, wherein the chimeric fungal Cel7A polypeptide further comprises the linker domain from the *Penicillium funiculosum* Cel7A polypeptide.

11. The isolated chimeric fungal Cel7A polypeptide of claim 10, wherein the chimeric fungal Cel7A polypeptide further comprises the carbohydrate-binding molecule (CBM) form the *Penicillium funiculosum* Cel7A polypeptide.

12. The isolated chimeric fungal Cel7A polypeptide of claim 10, wherein the chimeric fungal Cel7A polypeptide further comprises the carbohydrate-binding molecule (CBM) from the *Trichoderma reesei* Cel7A polypeptide.

13. The isolated chimeric fungal Cel7A polypeptide of claim 9, wherein the chimeric fungal Cel7a polypeptide further comprises the carbohydrate-binding molecule (CBM) from the *Penicillium funiculosum* Cel7A polypeptide.

14. The isolated chimeric fungal Cel7A polypeptide of claim 13, wherein the chimeric fungal Cel7A polypeptide further comprises the linker domain from the *Trichoderma reesei* Cel7A polypeptide.

15. A method for degrading cellulose or lignocellulose biomass, comprising contacting the cellulose or lignocellulosic biomass with the isolated chimeric Cel7A polypeptide according to claim 1.

16. A method for producing a biofuel from lignocellulosic biomass, comprising:
   a) contacting the lignocellulosic biomass with an enzyme cocktail comprising the isolated chimeric fungal Cel7A polypeptide according to claim 1 to generate sugars; and
   b) converting the sugars to a biofuel by fermentation.

17. The method of claim 16, wherein the enzyme cocktail further comprises an endoglucanase, a β-glucosidase, or both.

* * * * *